(12) United States Patent
Prokoski

(10) Patent No.: US 8,811,692 B2
(45) Date of Patent: Aug. 19, 2014

(54) SYSTEM AND METHOD FOR USING THREE DIMENSIONAL INFRARED IMAGING FOR LIBRARIES OF STANDARDIZED MEDICAL IMAGERY

(76) Inventor: Francine J. Prokoski, Fairfax Station, VA (US)

( * ) Notice: Subject to any disclaimer, the term of this patent is extended or adjusted under 35 U.S.C. 154(b) by 496 days.

(21) Appl. No.: 12/596,634

(22) PCT Filed: Apr. 15, 2008

(86) PCT No.: PCT/US2008/060306
§ 371 (c)(1),
(2), (4) Date: Mar. 22, 2010

(87) PCT Pub. No.: WO2008/130903
PCT Pub. Date: Oct. 30, 2008

(65) Prior Publication Data
US 2010/0191541 A1 Jul. 29, 2010

Related U.S. Application Data

(60) Provisional application No. 60/923,764, filed on Apr. 17, 2007.

(51) Int. Cl.
*G06K 9/00* (2006.01)
(52) U.S. Cl.
USPC .................................. 382/128; 705/2; 705/3
(58) Field of Classification Search
USPC ........................................................... 705/2
See application file for complete search history.

(56) References Cited

U.S. PATENT DOCUMENTS

| | | | | |
|---|---|---|---|---|
| 5,163,094 A * | 11/1992 | Prokoski et al. | ............... | 382/118 |
| 5,583,950 A * | 12/1996 | Prokoski | ....................... | 382/212 |
| 5,982,932 A * | 11/1999 | Prokoski | ....................... | 382/224 |
| 6,173,068 B1 * | 1/2001 | Prokoski | ....................... | 382/115 |
| 6,751,340 B2 * | 6/2004 | Prokoski | ....................... | 382/118 |
| 7,027,621 B1 * | 4/2006 | Prokoski | ....................... | 382/118 |
| 7,152,024 B2 * | 12/2006 | Marschner et al. | ............... | 703/2 |
| 7,961,134 B2 * | 6/2011 | Ranney et al. | ............... | 342/25 R |
| 2010/0172567 A1 * | 7/2010 | Prokoski | ....................... | 382/132 |
| 2010/0189313 A1 * | 7/2010 | Prokoski | ....................... | 382/118 |
| 2010/0191124 A1 * | 7/2010 | Prokoski | ....................... | 600/473 |

\* cited by examiner

*Primary Examiner* — Michael Fuelling
(74) *Attorney, Agent, or Firm* — Whitham, Curtis, Christofferson & Cook, P.C.

(57) ABSTRACT

Calibrated infrared and range imaging sensors are used to produce a true-metric three-dimensional (3D) surface model of any body region within the fields of view of both sensors. Curvilinear surface features in both modalities are caused by internal and external anatomical elements. They are extracted to form 3D Feature Maps that are projected onto the skin surface. Skeletonized Feature Maps define subpixel intersections that serve as anatomical landmarks to aggregate multiple images for models of larger regions of the body, and to transform images into precise standard poses. Features are classified by origin, location, and characteristics to produce annotations that are recorded with the images and feature maps in reference image libraries. The system provides an enabling technology for searchable medical image libraries.

9 Claims, 32 Drawing Sheets

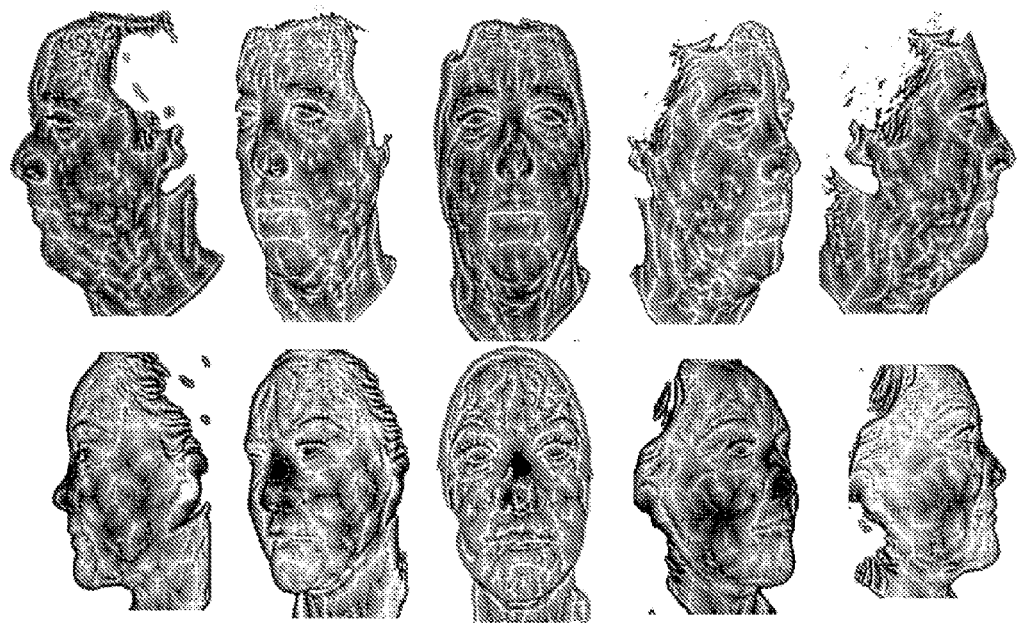
Dense feature content at any angle
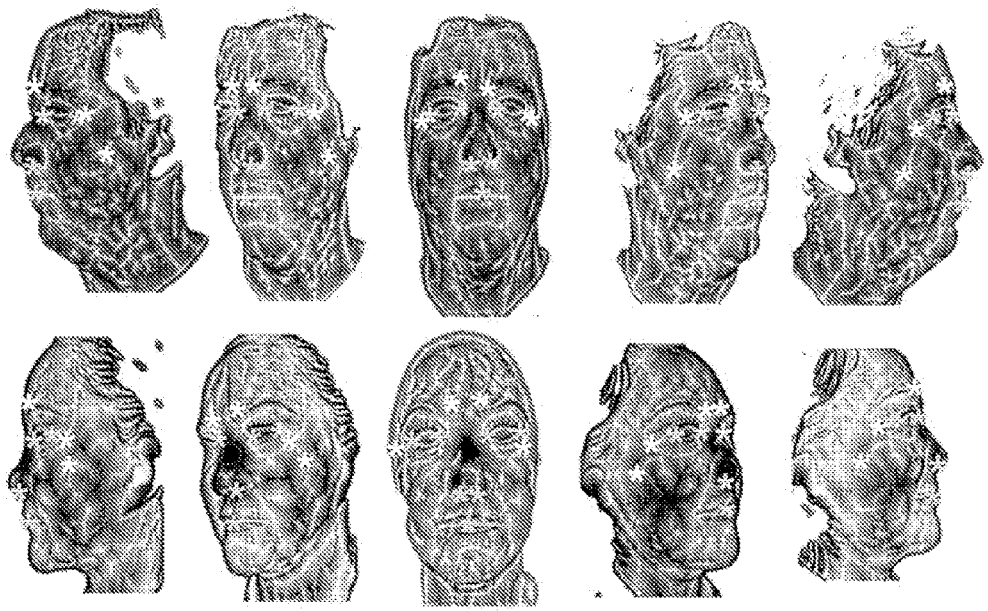
Figure 16

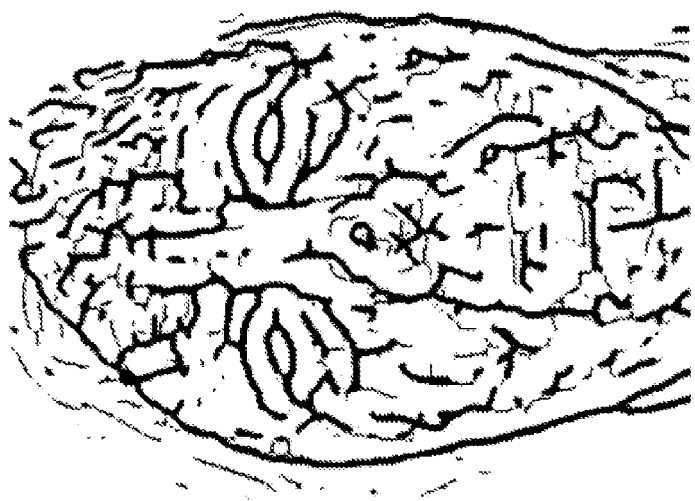
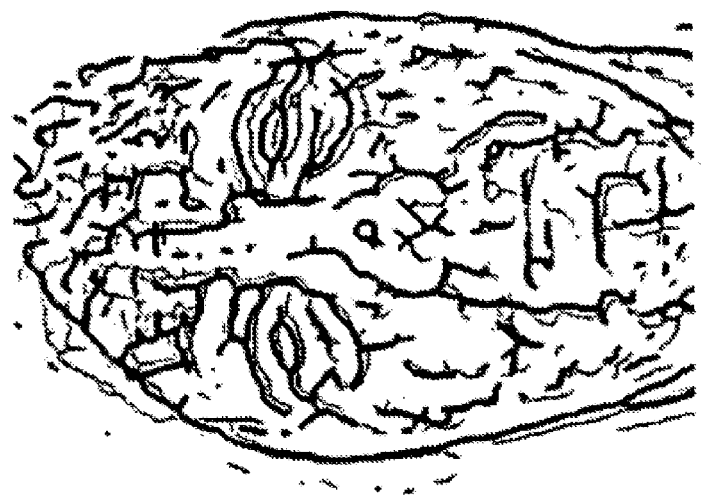
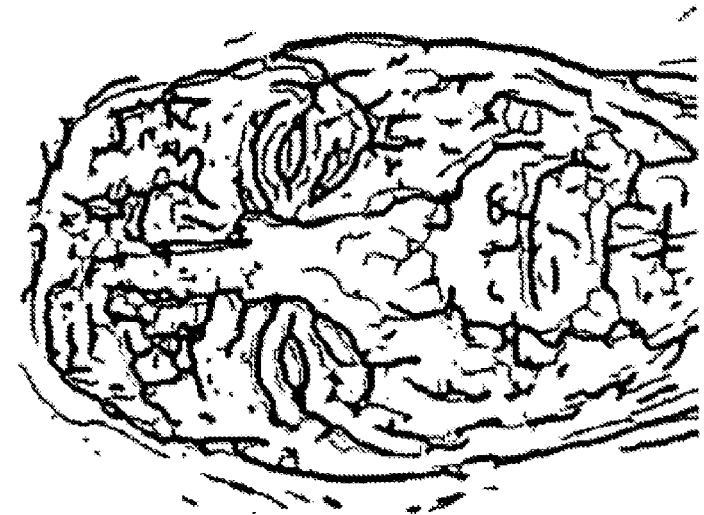
Figure 25B

SYSTEM AND METHOD FOR USING THREE DIMENSIONAL INFRARED IMAGING FOR LIBRARIES OF STANDARDIZED MEDICAL IMAGERY

RELATED APPLICATIONS

This application claims priority from U.S. Provisional Patent Application Ser. No. 60/923,764 titled "System and Method to Standardize Medical Images" filed Apr. 17, 2007, as claimed in PCT Application No. PCT/US2008060306 tiled on Apr. 15, 2008, from which this application is derived.

BACKGROUND OF THE INVENTION

1. Field of the Invention

The present invention generally relates to the use of infrared imaging and, in particular, to the use of three dimensional infrared anatomical imaging for libraries of standardized medical imagery.

2. Background Description

Standardized Medical Imaging

Imaging Sensor Technologies

Several medical imaging technologies are in common use:

X-ray images such as from mammographs and chest X rays are produced from X rays passing through and being attenuated by the patient's body tissues to produce a 2D projection image. The density at a point in the image represents the tissue densities through which the x-rays passed. X-ray imagery shows bone structure and fatty tissue Computed Tomography (CT) or Computed Axial (Computer Assisted) Tomography (CAT) have the same source as conventional X-rays. Multiple X-rays are taken at different angles to the patient and mathematically reconstructed 3D images are produced. Contrast agents supplied to the patient can aid in imaging soft tissue.

Magnetic Resonance Imaging (MRI) is produced through absorption of energy from Radio Frequency (RF) pulses when excited nuclei return to their original state. Images of tissue hydrogen concentration are produced that reflect the different structures imaged. MRI is considered noninvasive, provides high-resolution images, and is much safer than imaging using X rays. However it is expensive and generally requires a longer scanning time than CT. Functional MRI (fMRI) images provide both structural and performance information.

Magnetic Resonance Angiography (MRA) is a specific type of MRI that produces an image of blood flow for the visualization of arteries and veins.

Digital Subtraction Angiography (DSA) produces images of a patient's blood vessels as the difference image between a post- and a pre-contrast injection images. Since the contrast medium injected flows only in the vessels, the image data arising from other structures does not change in the two images and are eliminated by the subtraction.

Ultrasound imaging uses pulsed or continuous high-frequency sound waves to image internal structures by recording the different reflecting signals. Among others, ultrasound imaging is used in echocardiography for studying heart function and in prenatal assessment. Although ultrasonographic images are typically not high-resolution as images obtained through CT or MRI, they are widely adopted because of ultrasound's non-invasiveness, cost effectiveness, acquisition speed, and harmlessness.

Nuclear medicine acquisition methods such as Single Photon Emission Computed Tomography (SPECT), and Positron Emission Tomography (PET) are functional imaging techniques. They use radioactive isotopes to localize the physiological and pathological processes rather than anatomic information.

Digital X-ray systems have recently been developed which take whole body images in less than 15 seconds vs. 45 minutes or more for conventional X-rays that imaged only a portion of the body at a time. The new systems, developed for routine scanning of workers in South African diamond mines, expose persons to 75 percent less radiation than a conventional fullbody X-ray series.

All produce images oriented to body-centric models, but fusion of images from multiple sensor modalities is neither automatic nor precise. Some techniques involve injection of contrast agents or use of potentially harmful radiation. 3D/IR does not. In addition, 3D/IR is much less expensive to purchase, maintain, and operate; is portable for rapid deployment to thermal triage at accident locations; and its images automatically contain features for patient identification.

Medical Image Segmentation

Segmenting an anatomical structure in a medical image amounts to identifying the region or boundary in the image corresponding to the desired structure. Segmentation is beneficial when applied to image data of both patients with pathology and normals used for comparison to define abnormality. Segmentation in IR images shares technical issues with MRI images. In particular, locating blood vessels, determining centerline location and branch point locations, treating hidden segments and apparent discontinuities.

Manually segmenting a structure in three-dimensional data is prone to errors. Experts cannot visualize the entire 3D data collection simultaneously and so resort to outlining the structure of interest manually in a series of consecutive two-dimensional slices out of the original 3D volume. This slice-by-slice approach to manual segmentation is time consuming and generally suffers from poor reproducibility of results for a given analyst, as well as variations among analysts.

Visualization Techniques in Medical Imaging

Radiographic imaging of coronary arterial structure plays a crucial role both in diagnosing and treating patients who are at risk of heart disease. In order to exploit the information generated by current clinical methods in coronary arteriography, it is necessary for the physician to build a mental model of both the three dimensional (3D) arterial structure and of the non-rigid motion that this structure undergoes as it moves with the beating heart. This mental model must be constructed from sequences of two dimensional (2D) images obtained from the x-ray projection process. The image data acquired is noisy and often difficult to interpret.

To facilitate clinical decision-making process, computational algorithms have been developed for the purpose of generating a structural representation that is better suited for understanding and visualization by the physician. The primary focus of these algorithms has been to detect salient image features and then complete a segmentation of the angiographic 2D image. The segmented images can then be used to build and label a 3D model of the vascular system that can be interactively studied by the physician as it undergoes the motion associated with the beating heart's cycle.

Methods for automated blood vessel enhancement and segmentation have been developed for angiographic image sequences to assist surgeons and physicians in visualizing the vascular system. While the methods were developed for x-ray, ultrasound, MRI, and other active sensors, they can be applied to analyzing thermal infrared image frames and sequences.

O'Brien and Ezquerra apply temporal, spatial, and structural constraints to automate segmentation of coronary vessels in angiographic image sequences. Their methods perform automated segmentation from sequences of biplanar x-ray angiograms by imposing an integrated set of constraints based on the anatomical structure of the vascular system, temporal changes in position due to motion, and spatial coherence.

Frangi examines the multiscale second order local structure of an image (Hessian) to develop a vessel enhancement filter. His vesselness measure is obtained on the basis of all eigenvalues of the Hessian. Its clinical utility is shown by the simultaneous noise and background suppression and vessel enhancement in maximum intensity projections and volumetric displays. Accurate visualization and quantification of the human vasculature is an important prerequisite for a number of clinical procedures. Grading of stenoses is important in the diagnosis of the severity of vascular disease since it determines the treatment therapy. Interventional procedures such as the placement of a prosthesis in order to prevent aneurysm rupture or a bypass operation require an accurate insight into the three-dimensional vessel architecture.

Both two-dimensional projection techniques, such as DSA, and three-dimensional modalities such as X-ray rotational angiography, CTA and MRA are employed in clinical practice. Although CTA and MRA provide volumetric data, the common way of interpreting these images is by using a maximum intensity projection. The main drawbacks of maximum intensity projections are the overlap of non-vascular structures and the fact that small vessels with low contrast are barely visible. This has been a main limitation in time-of-flight MRA. In contrast enhanced MRA, the delineation of these vessels is considerably improved, but other organs can be still projected over the arteries.

A vessel enhancement procedure as a preprocessing step for maximum intensity projection display will improve small vessel delineation and reduce organ over-projection. Segmentation of the vascular tree will facilitate volumetric display and will enable quantitative measurements of vascular morphology. There are several approaches to vessel enhancement. Some of them work at a fixed scale and use (nonlinear) combinations of finite difference operators applied in a set of orientations. Orkisz presents a method that applies a median filter in the direction of the vessel. All these methods have shown problems to detect vessels over a large size range since they perform a fixed scale analysis. Multi-scale approaches to vessel enhancement include cores, steerable filters, and assessment of local orientation via eigenvalue analysis of the Hessian matrix.

The multiscale approach was inspired by Sato and Lorenz who use the eigenvalues of the Hessian to determine locally the likelihood that a vessel is present. They modify the approach by considering all eigen-values and giving the vesselness measure an intuitive, geometric interpretation. They regard vessel enhancement as a filtering process that searches for geometrical structures that can be regarded as tubular.

When intra-arterial contrast material is injected, a reference image is first acquired without contrast, and then subtracted from the image with contrast for background suppression. If no motion artifacts are present, the subtracted images are of such good quality, that further processing is not desirable. They therefore only apply their enhancement filter to the contrast images directly, and use the subtracted images to judge the performance of the vessel enhancement filter. In the peripheral vasculature, performance of subtraction is usually quite good. Although contrast is not very high in the contrast images, the method detects most vessels, over a large size range. Since vessels appear in different sizes it is important to introduce a measurement scale that varies within a certain range. By determining the vesselness of the MRA image at multiple scales, separate images are obtained depicting vessels of various widths. Small and large vessels can be distinguished, which is used in artery/vein segmentation.

Image Standardization and Encoding

Computer processing can be used to 'normalize' MRI scans using programmed functions to reorient the angle, position, size, etc of the scan to standard stereotaxic space. Normalized images are much easier to read, because the slices match those available in published atlases. In addition, the majority of modern functional imaging studies normalize their scans to standardized space. Therefore normalized patient scans are easier to interpret relative to each other, to atlases, and to functional imaging studies.

Normalization routines seek to minimize differences between sections of the patient's image and corresponding sections from templates generated from healthy patients. Patient anomalies such as a lesion can distort the results. Non-linear normalization routines may try to minimize the anomaly by compressing that region—distorting the area of the image in the process and causing imprecision in location and size of the lesion in the normalized image. Using only linear normalization results in less risk of significant local distortion, providing better overall coregistration, although not achieving optimal local registrations.

The linear functions of translation, rotation, zoom and shear can be applied in each of the three dimensions. For example, rotation can be applied in the x, y and z coordinates, correcting yaw, pitch and roll of the input image). Any three points that are colinear in the input image will also be colinear in the output image, although two parallel lines in an input image may not be parallel after an affine transformation. Also, all of the 12 linear parameters (translation, zoom, rotation and affine functions each in the x, y and z dimensions) are computed based on information from the entire image—therefore these functions are rarely disrupted by anomalies such as lesions found in MRI scans. Unlike with linear functions, points that are colinear in the input image will not necessarily be colinear after nonlinear normalization. Furthermore, nonlinear functions are more heavily influenced by local image information, and therefore nonlinear normalization of patient scans may lead to distortion due to the unusual appearance of the anomaly. For this reason, it is necessary to mask lesions and clip artifacts when estimating a nonlinear normalization from MRI.

MRI systems commonly provide that two or more images can be yoked together to compare coregistration with each other or with a template, or to compare the effects of different normalization techniques. Displays automatically present corresponding slices of yoked images even if the images are sliced to different thicknesses or are cropped to show overlapping but different areas. The user must make the necessary adjustments manually.

Most MRI systems export scans in DICOM or a proprietary format. Most fMRI studies will generate a vast number of two dimensional images that are stacked to create three dimensional volumes. Not all scanners use the same axial slices, and different scanners use different methods for saving images.

DICOM and Health Level (HL7) standards and integration standard (IHE) Integrating the Healthcare Enterprise address aspects of the technology development needed for searchable databases and automated comparison of imagery. DICOM's hanging protocols (HP) arrange sets of images by group guided by preferences of the site, section, or user. The protocol can be specific for anatomic region, laterality, procedure code, and reason for the procedure. They can be environment specific in terms of number of displays. Processing treatment can be specified also.

For a facility to develop a consistent HP display, it must establish a protocol for how that examination is performed. There can be significant variability among radiologists in a subspecialized section where different radiologists perform different MR sequences to image the same anatomy. Many institutions use the same name for examinations of multiple anatomic regions—for example an MR of the ankle is called MR lower extremity, as is an MR of the knee or the tibia/tibula. Different system vendors often have different naming conventions for the same series.

Biometric Identification

Role of Biometrics

Increased reliance on digital patient records, including imagery, requires techniques for insuring that records are correctly associated with the correct patient. At the same time, patient privacy must be insured against identity theft and access control procedures must restrict viewing and modifying patient records to only authorized persons. The integrity of data and images within a searchable library must be maintained.

Biometric identification answers the question "Who are You?" by extracting physiological parameters unique to each person. Current biometric systems are primarily deployed to recognize persons who want to be recognized and who actively cooperate in their enrollment and subsequent recognition. Controlled tests of automated realtime systems have used subject populations under 100,000, required active cooperation, and achieved performance figures that justify using the systems to augment human guards. However, even when used in a verification mode (one-to-one matching) resulting error rates are too high to justify unattended access control into secure areas. When used to screen for persons on a Watch List (one-to-many matching) the resulting false alarm rates create unacceptable delays if the Watch List contains more than a few dozen people. Integrating multiple biometrics (in particular combining face recognition and fingerprint matching) and upgrading visual face recognition to 3D can improve system accuracy, but may degrade system speed and reliability to unacceptable levels.

Limitation of Current Biometric Technologies

Current biometric technologies are not secure against sophisticated adversaries intent on forging another person's biometric identity. Visual Facial Recognition Systems used with a human attendant can be defeated by makeup and disguise. Automated, unattended systems may be defeated through "before the lens tampering", by presenting to the system camera a photograph or hand-held video display of an authorized person—avoiding the need to wear makeup or disguise.

Livescan Fingerprint Systems can be defeated with or without the cooperation of an authorized person. Unattended systems may be defeated by reactivation of a residual print. Because fingers leave residual oils on a fingerprint sensor, blowing hot breath on the sensor, placing a water-filled balloon on top, or illuminating with a halogen flashlight may reactivate a previously-left authorized print. Another approach is to obtain a latent fingerprint from an authorized person and place it on the sensor. A synthetic peel-off finger covering can be molded from a stolen print. Yokohama University reported a method for producing silicon or Gummi-Bear synthetic fingers from latent prints or directly from the authorized person's finger. Use of synthetic finger coverings would likely not be detected unless a human guard visually inspected each person's fingers at the time the sensor was used.

Photographs of an authorized person's iris can be collected without his knowledge by using high-resolution digital video imagery to capture from a distance an image of the eye. Only a single frame is required. The iris pattern is then printed on a mask or imprinted on a contact lens to impersonate the authorized person.

A trusted biometric system must be able to distinguish real and forged biometric features. Ideally, it would be able to identify a person in spite of his attempts at forging another identity. At a minimum, it must detect all forgery attempts. Various techniques for improving the ability of biometric systems to detect attempts at forgery will continue to be made as the value associated with successful biometric identity theft continues to increase. Any biometric system relying on features that can be covertly collected and forged cannot guarantee security against future forgery methods. In order to trust biometric identification systems for applications involving national security, the features used must be impervious to forgery even through sophisticated means such as radical surgery. For positive identification within very large populations, the underlying physiology must insure that the features are unique for each person.

Biometric identification based on the use of subsurface anatomical features provides security against biometric identity theft because the features are not readily observable to would-be forgers. If the sensor is unknown or difficult to obtain, that provides additional security for the system. Even if the sensor or the anatomical information from an authorized person is easy to obtain, it should be impossible for one person to surgically alter his anatomical features to mimic those of another person without leaving evidence that he has done so. Facial surgery that was sufficiently extensive to fool a 3D/IR system would necessarily pose a significant risk of death.

To meet requirements for cost, speed, convenience, and automation, biometric systems often use a reduced feature set and use procedures and sensors that might not distinguish between actual features and forged features. This is the case with fingerprint sensors. Acceptance of the uniqueness of fingerprints was based upon rolled inked prints taken by a trained technician who would repeat the collection procedure if the quality of the prints obtained was inadequate. The transition to automated livescan sensors in theory offers the same or better potential image quality; however, the self-imaging procedure does not provide consistent quality images and the users may not be trained or motivated to assure maximum quality.

Accuracy, speed, reliability, and system cost are not the only parameters important in rating biometric systems; population coverage, scalability, security, user convenience, and life cycle cost must also be addressed. Current biometric systems give unacceptable performance when large populations are enrolled; even when lighting conditions are ideal and even when there is no attempt at sophisticated disguises or forged identities. When biometric technology is reduced to practice, care must be taken to maintain as much as possible of the inherent uniqueness, persistence, scalability, and quality of the characterizing features for that biometric. This is best accomplished when the sensors do not require contact with the subject and are self-regulating with respect to focus, contrast, and other imaging parameters.

Face Recognition

Visual face recognition techniques require controlled lighting, are vulnerable to normal daily changes in appearance as well as to intentional disguise, and do not have sufficient feature complexity or density for scalability to a billion people. Other biometrics such as iris scanning or fingerprints require close or contact distances and cannot be performed in realtime with non-cooperating subjects. 3D/IR-ID offers faster throughput, greater security against identity theft, greater potential for covert use under darkness, and ability to match against legacy databases including mug shots, driver licenses, and passport photos.

Depending on the number of persons to be identified, use of highly precise IR and range imagers, together with precise standardization, can reduce the numbers of features required for positive unique ID. Using some number of large features over a large area of the face can yield the same performance as using a greater number of smaller features over a smaller area. Requirements for distance, system cost, level of cooperation, expected pose variations, population size, accuracy requirements, speed of processing, file sizes, Face Code size, and exportability of the technology influence the size threshold of features considered.

Pentland utilized eigenanalysis of visual faces to develop a set of characteristic features. Faces are then described in terms of weightings on those features. The approach claims to accommodate head position changes and the wearing of glasses, as well as changes in facial expressions. Pentland remarks that pre-processing to produce a canonical form of the face including only the area from just above the eyebrows to just below the mouth and with width equal to that height is essential to eigenvector recognition systems. Processing to automate that task and establish the eigenvector set is extensive, especially for large databases.

There is increasing need for automated face recognition systems that are scalable to very large populations and accurate under a broad range of ambient conditions. Two-dimensional visual face recognition cannot provide the required performance when lighting varies, an extended period of time intervenes, or there is a change in appearance caused by aging, illness, cosmetics, disguise, or surgery. Three-dimensional visual face recognition, using structured light or coherent laser radar, provides a partial solution to reducing errors associated with variations in lighting and head pose. ID can be based on the visible or range data rotated into a standard pose.

Visible metrics require ground truth distance measurements unless they rely strictly upon ratios of measurements. In that case, they are dependent upon precise designation of landmark positions within visible feature areas. For example, designation of eye corners, nose tip, nostrils, and ear-head locations entail surface areas that encompass many pixels in the visual image. Variations in landmark selection points create significant differences in scaling and can be seriously affected by intentional disguises, facial expressions, makeup, sunburns, shadows and similar unintentional disguises. Detecting the wearing of disguises and distinguishing between identical twins can generally not be done from visible imagery (2D or 3D) or range imagery from a distance.

Biometric identity theft may be prevented by technology that performs identification using internal anatomical features that cannot be forged by one person attempting to be identified as someone else without significant risk of death. Prior patents of Prokoski relied upon the complexity of the subsurface anatomical features extractable from infrared imagery to assure uniqueness for each person's pattern of features. Identification based on infrared imagery was offered as a robust biometric approach that is not vulnerable to biometric identity theft.

Infrared Face and Body Parts Biometrics

The identification of persons from infrared images is known in the art as evidenced by Prokoski U.S. Pat. No. 5,163,094 to the present inventor, which discloses a method and apparatus for analyzing closed thermal contours, called "elemental shapes" which are created by the vascular system interacting with the anatomical structure. Fifty or more elemental shapes can be identified for example in a human face imaged with an IR camera that has an NETD (noise equivalent thermal difference) of 0.07° C. and a spatial resolution of 256×256 pixels. Characteristics of those shapes, such as the centroid location and ratio of area to perimeter, remain relatively constant regardless of the absolute temperature of the face, which varies with ambient and physiological conditions. Two infrared images are compared by comparing the characteristics of corresponding shapes. A distance metric is defined and calculated for each pair of images. If the value is within a threshold, the two images are considered to be from the same person. Claims cover use of thermal contours for identification of faces and body parts. Preferred embodiment includes use of template matching from areas of the face that have little variation due to facial expression changes.

Thermal Infrared identification based on thermal contour analysis of subjects who are not wearing eyeglasses, or who always wear the same eyeglasses, has been shown to be useful for identification against medium size databases, defined as 100,000 to 1,000,000 images, when the subject actively cooperates or is induced to cooperate such as by the need to look at a red/green light in order to proceed through a metal detector arch. However, thermal contour analysis of IR facial images is not sufficiently accurate or fast when used against very large databases or when imagery to be compared has different positions of the subject's head, or different temperature distributions, since those produce significant changes to the thermal contours used for identification. In order to reduce errors associated with changes to the edges of thermal contours, using smaller characterizing features increases the likelihood that a sufficient number of features will remain unaffected by changes in head position, eyeglasses, hairstyle, and temperature.

Prokoski's 1992 publication of research utilized a principal components analysis of thermal shapes found in facial thermograms. The resulting accuracy of 97% equals or surpasses the results reported by Pentland with visible facial images. Prokoski's training database, furthermore, included identical twins and involved non-cooperative imaging of about 200 persons. Thus, the head sizes and orientations were not predetermined as they were in the Pentland study. As a result, the use of eigenanalysis of thermal shapes is concluded to be more robust than the use of eigenanalysis of visual facial features. However, the basic requirements of eigenanalysis still pertain of course to their use in matching of thermal images by consideration of inherent elemental shapes. That is, the approach is computationally intensive, requires a preformed database, and requires standardization of the images through pre-processing.

Prokoski U.S. Pat. No. 6,173,068 discloses a method and apparatus for extracting and comparing thermal minutiae corresponding to specific vascular and other subsurface anatomical locations from two images. Minutiae may be derived from thermal contours, or may be absolutely associated with specific anatomical locations that can be seen in the thermal image, such as the branching of blood vessels. Each minutia is then associated with a relative position in the image and with characteristics such as apparent temperature, the type of branching or other anatomical feature, vector directions of the branching, and its relation to other minutiae.

The comparison of thermal minutiae from two facial images is analogous to the comparison of sets of fingerprint minutiae, in that two images are said to identify the same person if a significant subset of the two sets are found to correspond sufficiently in relative positions and characteristics. Classification of the facial thermograms can be performed to partition a database and reduce the search for matching facial patterns. Alternately, encoding of the minutiae patterns offers a unique FaceCode that may be repeatably derived from each person, minimizing the need for searching an image database.

Effective biometrics must be fast, accurate, foolproof, easy to use, provide full population coverage, be free of racial or ethnic bias, and work even on non-cooperating subjects. Current biometric techniques including: hand geometry, fingerprints, retina and iris scanning, voice recognition, and visual facial recognition each has inherent technical limitations that prevent satisfying all those requirements.

Both eyewitness and automated face recognition suffer from vulnerability to lighting changes. In very dim light, or darkness, neither can identify faces. Many automated face recognition system use an IR illuminator to bounce invisible light off the skin. The resulting image provides some feature measurements, but little detail. This is IR-illuminated visual face recognition, not Infrared Face Recognition. The term "IR image" refers to the output from focal plane array or scanning sensors sensitive to emissions within the 3-14 micron range. The IR camera is totally passive, emitting no energy or other radiation of its own, but merely collecting and focusing the thermal radiation spontaneously and continuously emitted from the surface of the human body.

Infrared cameras with low enough MRTD (minimum resolvable temperature difference) are able to directly sense the difference between skin immediately overlaying the superficial blood vessels, and adjacent skin. An MRTD of 0.04° C. is sufficient for locating large vessels. Different people in the same environment may have average face temperatures differing by six degrees or more; and an individual's face may display a 10 degree variation in temperature, producing saturated areas in the imagery, with resulting loss of data, if the camera has insufficient bandwidth. Variations in depth and width along a blood vessel, coupled with large local changes in surface temperature, and the blurring effect of thermal conduction create a blotchy surface thermal pattern containing few if any curvilinear structures, and no apparent minutiae. Novel processing steps are required to extract consistent curvilinear features and to extract characterizing minutiae.

In addition to the novel processing steps, the camera optics, array size, instantaneous field of view of the detectors and fill factor must combine to produce clear definition of vascular features on the order of 2 mm wide, with consistent skeletonization and minutiae extraction. Biometric identification based on comparison of thermal vascular segments or thermal minutiae is akin to fingerprint ridge or minutiae matching, and compares favorably to the computationally intensive approaches involving Eigenfaces or Hidden Markov Method comparisons by other biometric approaches using visual or infrared images.

Development of the body's highly complex vascular structure has been modeled from embryo angiogenesis and tissue repair angiogenesis. Using any of the various models, the number of branches and nodes, and randomness of the growth patterns of branches, yields estimates for the uniqueness of vascular patterns for each person over any sizable area of his body. Comparison with the quantitative uniqueness of fingerprints as determined by Pankati indicates that vascular patterns of portions of the body are more unique than fingerprints.

All current biometrics have serious inherent limitations in non-cooperative identification against very large databases. In particular, iris and retinal scanning, hand and fingerprints require active cooperation by the subject at close distance and are therefore relatively slow, require training, and cannot be used for covert or non-cooperative identification. Face recognition based on visual images can be performed from long distances without cooperation, but is prone to changes in illumination, intentional disguises, and similarity in appearance of many people. Two-dimensional face recognition based on infrared imaging as invented by Prokoski improved upon the limitations of visual face recognition, but use against very large populations required scaling based upon 2D projection estimates of three-dimensional landmarks.

Prokoski's previous patents for infrared identification used analysis of thermal contours, thermal minutiae, autowaves, IR-visual correlation, and direct comparison of infrared images standardized as to scale, orientation and histogram. Given suitable IR camera optics, array size, instantaneous field of view of the detectors, fill factor, and bandwidth, the patented processing methods provide clear definition of vascular features on the order of 1 mm wide. Comparison of thermal vascular segments or thermal minutiae is computationally akin to fingerprint ridge or minutiae matching, and compares favorably to computationally intensive approaches involving Eigenfaces or Hidden Markov Method comparisons of facial images.

Prokoski U.S. Pat. No. 6,173,068 teaches the use of thermal minutiae for identification. Encoding uses location relative to standard axes and landmarks, and may also include type, connectedness, vectors, and other parameters. The resulting template that identifies an individual is not compact. A compressed binarized 2D image of the vasculature offers greater compaction with less processing and is more forgiving of variances in the sensor data. Claims cover use of structural data obtained from infrared and other medical imaging sensors for identification of patients and other subjects. Preferred embodiment defines as minutiae the branch points and apparent end points of blood vessels in the face as seen in passive infrared images, and uses these minutiae to identify the person. Fingerprint minutiae-matching techniques can be used for the matching step.

The number of minutiae and area of distribution is much greater for facial thermal minutiae than for a fingerprint. Also, there is a larger variance in width of facial vessels compared to little variance in fingerprint ridge spacing. Furthermore, fingerprint ridge lines are constrained by the boundaries of the fingers to be concentric, whereas no such restriction applies to interior facial vessels. The degrees of freedom relating to facial thermal minutiae are therefore significantly greater than the degrees of freedom for fingerprint minutiae. Following the Supreme Court Decision in Daubert vs Merrell Dow Pharmaceuticals (92-102), 509 U.S. 579 (1993), a number of court cases have raised the issue that no scientific basis has been established for the claim that fingerprints are unique other than statistical analysis of observations. Therefore, there has been no scientific basis for claiming that two partial fingerprints are from the same person if they contain a specific number of similar minutiae characteristics. Concerted efforts are underway at various universities to derive those scientific bases for fingerprints. We expect that some number of those efforts will succeed and will lay a foundation for analyzing the uniqueness and scalability of infrared facial minutiae.

Prokoski U.S. Pat. No. 6,920,236 teaches overlay and combination of visual and infrared imagery for identification to reduce the limitations of each sensor.

Prokoski U.S. Pat. No. 6,850,147 teaches encoding of a biometric template for seamless access and transmission of identification.

Prokoski U.S. Pat. No. 6,529,617 teaches the use of thermal minutiae to stabilize positioning of a patient.

Prior art includes developments made by this inventor to use curvilinear features from infrared images to identify persons by template matching of the feature maps; by minutiae matching of minutiae derived from intersections, branchings, and apparent endings of the treelike feature maps; and by FaceCodes which are standardized representations of the feature maps and/or minutiae. Those developments utilized two-dimensional imagery for identification based on template matching and extracted codes. The IR FaceCode production of the present inventor's prior art included classification of all curvilinear features extracted from the thermal image into vascular, skin folds, facial hair, and other.

SUMMARY OF THE INVENTION

A first aspect of the invention is a method for establishing a searchable library of human images, comprising: standardizing images for automated comparison, including images generated by a plurality of imagers having different types of sensors, ranges of sensitivity, and resolution; specifying standards for acceptable image quality from said plurality of imagers; specifying standards for metadata accompanying transmission or storage of said images; providing access control provisions for transmission and storage of the images; establishing procedures for detecting and correcting errors in the images; and storing standardized images in the library. A second aspect of the invention is a method according to the first aspect wherein the standardizing standardizing step further comprises: specifying a body-centric coordinate system; identifying a defined axis for each anatomical division of the body, the anatomical divisions including regions, sub-regions, and body segments within a region; determining three specified landmark points in each division used for standardization, the three landmark points for each segment defining a facet; combining facets to form a faceted 3D model; and replacing facet edges by transition curves to form a three dimensional (3D) model.

A third aspect of the invention is a method according to the first aspect, wherein storing standardized images in the library further comprises processing the images in accordance with the standards for acceptable quality and for metadata. A fourth aspect of the invention is a method in accordance with the second aspect, further comprising automatic standardization through contemporaneous use of three dimensional infrared imaging (3D/IR). A fifth aspect of the invention is a method in accordance with the fourth aspect, further comprising: extracting feature maps from the 3D/IR images; establishing a directory of reference points for each division of the body; using three designated reference points to standardize a pose for each image; and storing standardized images in a database along with the metadata for each.

A sixth aspect of the invention is a method for standardizing medical images such that the subject appears in a standard pose. This is accomplished by simultaneously capturing images of the subject from thermal infrared, range, and a medical imaging sensor; producing a 3D/IR image through intrinsic and extrinsic calibration of the range and infrared sensors; extracting anatomical curvilinear line segment features from the three dimensional thermal images by performing locally adaptive filtering to enhance visualization of internal and external anatomical structures including blood vessels and skin folds; selecting three or more landmark points either manually or automatically where the anatomical landmark points to be selected are specified for the body part being imaged; transforming the 3D/IR image into a standard pose specified for the area of the body imaged by transforming the plane determined by the three selected points into an orientation and position specified for that standard pose; and transforming the medical sensor image into standard pose by overlaying the medical sensor image on the 3D/IR image through intrinsic and extrinsic calibration of the IR and medical sensors. In a further aspect of the invention the medical image sensor in the sixth aspect is an IR sensor.

Another aspect of the invention is a method in accordance with the sixth aspect, further comprising differentiating internal and external features in infrared images by extracting curvilinear line segment features from range and thermal image layers in a body map; determining which features appear in both layers; designating features that appear in both thermal and range images as external features; and designating features that appear in the thermal but not in the range images as internal features.

Calibrated infrared and range imaging sensors are used to produce a true-metric three-dimensional (3D) surface model of any body region within the fields of view of both sensors. Curvilinear surface features in both modalities are caused by internal and external anatomical elements. They are extracted to form 3D Feature Maps that are projected onto the skin surface. Skeletonized Feature Maps define subpixel intersections that serve as anatomical landmarks to aggregate multiple images for models of larger regions of the body, and to transform images into precise standard poses. Features are classified by origin, location, and characteristics to produce annotations that are recorded with the images and feature maps in reference image libraries. The system provides an enabling technology for searchable medical image libraries.

Other imagers, such as X-ray and ultrasound scanners, can be calibrated with the 3D/IR sensors to apply the same feature mapping, annotation, segmentation, standardization, and search methods to their images. Encoding of standardized feature maps provides a robust biometric identification technique for faces or other body regions. Automated comparison of standardized images from a specific patient at different times provides fast, precise change detection to aid prognosis. Automated comparison of standardized imagery from a specific patient against a library of standardized images from previous patients facilitates faster diagnosis at lower cost.

3D/IR: Standardization, Identification, Comparison

It is a primary embodiment of the present invention to standardize images of the human body by using subsurface anatomical landmarks derived from three-dimensional infrared imaging. Simultaneous imaging of all or some portion of the body with calibrated infrared and range sensors yields a true metric 3D surface thermal model of any body area within the fields of view of both sensors. Variations in apparent temperature, emissivity, and elevation along the 3D surface are due to both internal and external anatomical elements. Anomalous regions, including local min, max, and saddle-point locations, are located and their connectedness considered. Apparent edge, ridge, and groove features are classified by origin and characteristics, then processed to produce a 3D curvilinear line features. Adaptive local equalization enhances contrast and assists in maintaining continuity of vascular and other internal features in spite of depth and width variations beneath the skin. Similar processing of range data produces range feature patterns containing external edge contours. Skeletonization of feature patterns produces 3D/IR feature maps with single pixel or subpixel intersections that serve as anatomical landmarks projected onto the skin surface, which are used to aggregate maps from multiple images to form three-dimensional whole body models, transform images into precise standard poses and segment them by body area. Other imagers, such as X-ray and CAT scanners, can be calibrated to the 3D/IR sensor to apply the same annotation, segmentation and standardization to their images.

Reference anatomical landmarks are designated for each body area to transform images into standardized poses. This method produces consistent standardized infrared and surface topographic images for any portion of the body or the whole body for any person. It thereby enables automated change detection from images of the same subject taken at different times, with different imagers, in different poses, under different ambient conditions, by different medical staff using different protocols. The initial application is for wound care management; in particular for early detection of incipient pressure ulcers to enable preventive measures for avoiding the occurrence of Stage I pressure ulcers, and for documentation of a patient's status relative to the presence or absence of pressure ulcers at a particular time.

The 3D/IR imaging and standardization system also provides an enabling technology for searchable medical image database libraries. Automated comparison of standardized imagery from a specific patient against a library of standardized images from many previous patients facilitates faster diagnosis at lower cost. Automated comparison of image sequences from a specific patient over a span of time can be compared against sequences from previous patients who had the same medical need and received the same treatment or other treatment. Comparison results are used to aid prognosis or suggest changes in treatment.

Classification of thermal, elevation, and color features by origin [skin fold, vascular structure, lymphatic structure, hair, scar, wound, mole] and characteristics [shape, size, position, orientation] relative to a standard model, leads to an encoding of the imaged area of the body unique to the subject. Encoding of the standardized feature maps provides a robust biometric identification technique for faces or other body parts. A portion of the encoding is further processed through: landmarks designation, standardization, and compression, to generate templates representing selected areas of the face or other body part for biometric identification in digital patient records and for general use in biometrics.

Time-varying extraction and analysis of 3D/IR curvilinear and minutiae features before, during, and after a stimulus provides comparative evidence of physiological condition and psychological state of the subject. Changes in microexpressions, pulse and respiration rates, head and arm motions, posture and gait are monitored by changes in local 3D/IR features, and compared to the reaction of specific profiled groups to determine the subject's inclusion in profiled groups.

Sensor Calibration

Two-dimensional arrays of data values are captured from: infrared, range, and (optionally) visual (color or monochrome) imaging sensors. Each sensor's image may be of a different size and form factor, and each sensor may have a different field of view and different aspect angle to a subject's body. Intrinsic calibration of each sensor is performed to compensate for radial distortion in optics, bad pixels in arrays, and other anomalies created by imperfect focus, non-homogeneous detectors in the arrays, noise from various sources, and other imperfections in that sensor's imagery.

Commercial IR cameras generally have either an automatic or simple manual push-button thermal calibration provision by which users can correct the thermal response of the camera, and re-correct it periodically as ambient temperature changes, the camera temperature changes, internal gaskets and black body references warm. However, they do not have similar provisions for geometric calibration of the output imagery. The combined geometric variations introduced by mechanical assembly of the detector array and optics, changes to focus setting, and signal processing by the electronics can be determined for specific camera position and settings by using the camera to image a calibration target. For 3D/IR calibration it is necessary to image the calibration target at several orientations in three-dimensional space.

For infrared cameras the imaged pattern is determined by the temperature and emissivity of each surface point. Range, visual, and near-IR sensors do not see the same surface pattern as a thermal IR sensor. This provides a challenge for calibrating an IR camera to accomplish 3D-IR imaging. Special measurement procedures, and calibration target materials were developed to permit rapid 3D spatial calibration of IR cameras. The success of these procedures is verified by comparing extracted features of a 3D-IR image rotated into a selected pose through modeling and computation with those of the same subject viewed directly at that selected pose.

System Considerations

System design issues include the requirement to synchronize imaging from thermal imagers that can collect hundreds of frames per second and range imagers that are significantly slower. Both imager types currently produce data arrays on the order of 640×480 with larger arrays being developed. Array sizes are a limiting factor in achieving precise metrics and standardization, and in the potential scalability of a given identification methodology. Range sensors have utility only within certain distance bands determined by the ranging technology. For example, when the target is the size of a human face, structured light is limited to about 0.5 to 2.5 meters; coherent laser radar is effective from about 4 to 50 meters.

Range sensors may be adversely affected by dust, fog, smoke while the thermal sensor is less affected. Uncooled thermal sensor have poor depth of focus, requiring use at fixed distances or use of an autofocus capability. However, changing focal length changes the calibration of the thermal sensor, resulting in mis-registration of the thermal and range images, and incorrect standardization of the layered composite image unless calibrations are performed at a sufficient number of focal lengths so that a calibration exists for a focal length very nearly equal to the focal distance produced by the autofocus.

Other system considerations include the use of very bright visible light or lasers for many structured light systems, and the use of high intensity lasers for coherent laser radar at long distances. Eye safety can be assured by the selection of the laser used, and quality visual images can be obtained by using very short duration flash illumination to minimize obnoxious visual after effects for the subject. When the identification is to be performed without the subject's cooperation, visible illumination is to be avoided.

IR cameras with higher thermal sensitivity and greater spatial resolution produce a higher density of IR features, and longer feature lengths. Features produced by cameras with lower sensitivity or resolution are a subset of the features from higher performance cameras. This is a very important aspect of 3D/IR imaging since it enables a mixture of 3D/IR cameras to be used against the same database and allows for future improvement in camera performance.

Currently a sequence of thermal images can be obtained in the time taken to produce a single range image. In the future, range imaging techniques will produce faster frames, offering the possibility of multiple range images within a time interval during which the subject makes negligible movement. In all three sensor types thermal, range, and visual, image sequences can be used to reduce image noise, select the best frames for further processing, classify the subject, provide multiple sample images to enhance the probability of a database match, and to pinpoint landmark areas in the image such as blinking eyes in thermal sequences.

Once calibration is completed the IR camera coordinates may be related to the 3D-visual camera coordinates and 3D coordinates assigned to each jointly visible point of the IR scene. Using this "point cloud" information, 3D graphics software may be used to rotate objects such as a face in the IR scene. If multiple calibrated cameras are viewing the same scene, an object at any rotation angle may have its surface fade from that seen by one camera to another, thus allowing a direct comparison of the surface features provided by each camera. Similarly, IR face identification processing and decision logic may be applied to the same subject at the same time at the same viewing angle to get a direct comparison of the performance of the different cameras.

The relative geometry between any two cameras must be known in order to achieve precise, automated registration of their imagery, and must be fixed to maintain calibration. Cameras requiring manual focus adjustment are vulnerable to errors created by slight movements during focusing. Change in focus requires re-calibration.

Active IR can enhance visualization of thermal features. Lockin Thermography techniques have been developed to use modulated radiation to excite defects in structures, creating time-varying thermal changes that can be imaged with IR cameras for detection of very small defects. The technology of lockin thermography imposes a low-frequency wave on the whole surface of the object under test and images the resulting thermal patterns several times per modulation cycle. Image analysis on the resulting sequence is used to enhance detectability of defects. Absorption of intensity modulated radiation generates a thermal wave on the whole surface. It propagates into the interior where it is reflected at boundaries or defects and moves back to the surface, where it is superposed on the initial wave. Defects can be revealed by the local change in phase angle.

Imposing a modulated thermal variation on the skin surface provides a lower computational approach to extracting vascular structures from an IR image. Arterial blood vessels evince the heart's pulse rate; venous vessels, however, do not show such behavior. Imposing a cyclic thermal variation in surface temperature in sync with pulse rate enhances effective filtering out of the superficial arterial pattern of the face. A single point laser radar can obtain instantaneous heart rate off the face surface. Imposing a modulated thermal source in sync with the heart rate could enhance the effect to provide stronger signal to noise ratio and better continuity of the filter output. Rather than using a continuously-varying thermal source, there may be advantages to a double-pulse approach using hot and cold sources alternately to further amplify the filter output.

Image Capture and 3D Model Construction

The fields of view of the three sensors may be different, only the portion of the field of view seen by all three sensors is used. Ideally imagery will be collected simultaneously by all sensors, although differences in cycle times and difficulties with synchronization may introduce time delays which translate into blurred curvilinear features with less precise standardization, comparison, and identification. In general, there is not correspondence between the instantaneous fields of view represented by pixels in different sensor images. Differences in array sizes, image form factors, detector array fill factors, distortions in array layout and in optics are among the reasons why the raw data from the three sensors cannot simply be stacked. Achieving pixel-to-pixel registration requires calibration of each sensor and each combination of sensors, for each distance and focus setting.

Any 2D camera, analog or digital, visual or IR, single frame or video, views the scene in front of it as a projection of the surface points of the scene through a point in the center of the lens system on the optical axis onto the film or imaging chip behind the lens. If the 3D geometry of the surface in front of the camera is known, the exact position and orientation of the camera is known, and the geometric and optical parameters of the camera are known, then we can compute for each camera pixel the three dimensional coordinates of the surface point projected onto that pixel. The camera optical and geometric parameters are determined through a procedure called "camera calibration" in which multiple images of patterns of known geometry are acquired and analyzed to determine what camera geometry must exist to yield such images.

The intrinsically-calibrated range sensor provides the actual true size of the area imaged and the distance from the range imager to each pixel in the range sensor imagery. The digital visual imager is intrinsically calibrated to remove radial lens distortion and other aberrations from its images. The infrared imager is likewise intrinsically calibrated for spatial precision.

Extrinsic calibration procedures are then performed which create correspondence between elements of the three intrinsically-calibrated image arrays. Extrinsic calibration involves correcting for the differences in imager position, fields of view and detector array sizes, and instantaneous detector element fields of view of the corrected images from the three sensors. Extrinsic system calibration involves imaging a scene in front of the camera containing known 3D control points that can be located precisely in each sensor's data. The true positional relationship of each control point to the other points, as well as their relative elevation, emissivity, and temperature are known or estimated to within the desired precision of the 3D/IR imagery. Therefore, given selected reference origin and axes, 3D coordinates can be assigned to each control point on the actual calibration target, and to the representation of each control point in the infrared, visual, and range images.

From the pixel position of the control points on the image the relative positions and aspect angles of each imaging sensor are determined. Since the instantaneous fields of view of each detector element in the three arrays is generally different, without loss of generality we can create a fourth array called Standardized Composite which represents the true actual dimensions of the subject area imaged, with layers formed by the visual, infrared, and range data registered through calibrations and pose standardized relative to anatomical landmarks. The result of the extrinsic calibration is to create layers of the Standardized Composite array; one layer per sensor. Techniques well known to the art of image registration are used. For example, reference locations in each array are forced to correspond by re-gridding each corrected array to conform to the resolution of the Standardized Composite array, and to force all control point locations to overlay using minimal distortion at non-control point locations.

Each pixel in the Composite Array has values for (R, G, B, X, Y, Z, T). In the case of monochrome visual sensor R, G, and B are all equal to a Greyscale value. Digital visual imagers currently offer the largest sensor arrays of the three sensors in current commercial devices. Therefore, setting the size of the Standardized Composite array to be the same as the digital visual array may be useful to visualizing the output from the processing engine. The IR imager may have the smallest array size; typically 640×512, and is interpolated to match the visual image dimensions or selected reduced size. The range imager will produce a coarser data array than the visual imager and may produce a coarser array than the IR imager if fast imaging is required. Range data is similarly interpolated to achieve the desired array size. If parameters of the individual sensors don't change, and their relative positions and focus settings don't move, the calibration need not be repeated.

Modulated air flow with heating or cooling increases detectability of thermal features. Various medications and food products cause vasoactive stimulation that increases feature contrast at the skin surface. Other stimuli including odors, sounds, flickering lights, and irritants such as smoke can cause physiological changes affecting detectability of thermal features in certain individuals.

Feature Extraction of Curvilinear Structures & Minutiae

Key aspects of feature extractions to produce feature maps and skeletonized feature maps are the use of adaptive equalization to preserve continuity of the surface projection of blood vessels that vary in depth and width, allocating topographic variations to the surface projections of vascular features, and filling-in discontinuities smaller than a set size.

IR and range images must have no area in saturation. Since human skin temperature has generally a 10 degree Celsius or smaller variation, an infrared camera with temperature difference sensitivity of 0.01 degrees will require 1000 differentials or gray levels to encode the body without saturation, given the gain and level are adjusted correctly. For medical imaging, radiometric temperature measurement is recommended without gain and level variation, and different persons' skin temperature may vary over a 35 degree range. Therefore, 12-bit digital output is required to avoid saturation.

1. Capture IR and range (plus optional visual) images. Standardize the resultant 3D/IR image by designating the three anatomical locations for the region of the body imaged.
2. Perform adaptive local variance equalization of the standardized IR image to emphasize the structure of the curvilinear features and compensate for the nonlinearity in thermal response of the skin surface.
3. Reduce noise and threshold the resulting IR image to produce the feature map
4. Skeletonize the IR feature map
5. Perform edge selection from the standardized range image
6. Reduce noise and dilate resulting range image to produce topographic edges map
7. Label IR feature map features coincident with topographic edges "external"
8. Perform edge selection from the standardized visual image
9. Reduce noise and dilate resulting visual image to produce visual edges map
10. Label IR feature map features coincident with visual edges map "external"
11. Label remaining IR feature map features "internal"
12. Label each feature segment with its width
13. Designate apparent branch, intersection, and end points in the skeletonized feature map
14. Label features and minutiae points with their anatomical designations which link to a model for the full range of positions for each landmark. In the case of facial imaging, the link is to a library of expressions and speech-related elements.
15. Movement during capture of a frame of IR imagery may create motion blur from certain cameras. Processing can reduce the blur effect to some degree. Movement during capture of a frame of range imagery may be removed through processing as the frame scan progresses. Large movements from frame to frame of the whole body or of the region being imaged are processed out during standardization of both IR and range imagery. Local movements frame to frame within the field of view or those that do not affect the landmarks used for standardization are not removed in processing and provide useful indicators for condition assessment.

Localized Adaptive Contrast Enhancement

A healthy human body may evince a range of skin temperatures on the order of 15° C. Skin immediately over a blood vessel may be only 0.05° C. warmer than adjacent skin. Thermal infrared cameras having 1° C. sensitivity will likely not be useful in distinguishing the location of blood vessels unless the cameras have high spatial resolution and extensive processing is done, including multi-frame integration. Extraction of highly-defined vascular structure in general requires high thermal sensitivity and high spatial resolution.

Cameras are commercially available with sensitivity of 0.015° C., meaning 1000 colors or grey levels, or ten bits, would be required to represent one person's thermal pattern at a particular instant. The skin temperature of live human can have 70° C. variation, requiring twelve bits per pixel.

The method of the present invention extracts a binary representation of curvilinear features, both internal and external, from infrared images. This requires processing methods that consider localized temperatures in order to minimize the impact of the 15° C. variation across the body, and which consider only the temperatures of a particular body, in order to minimize the impact of the 70° C. spread on file size and bandwidth requirements. Internal features, including the vasculature, therefore, are to be located based upon local increased temperature along a curvilinear path on the skin created by underlying blood vessels. Two-dimensional filtering operations are implemented as digital convolution with kernels of limited numbers of pixels. High pass filtering can emphasize details small compared to the size of the convolution kernel, but the technique has limited effectiveness when constrained to small kernels, for which noise may be the primary component enhanced. Larger convolution kernels—on the order of several percent of the image width—have less noise-enhancing results, but require intensive computation time and bandwidth.

Wallis and Peli/Lim developed enhancement algorithms which can be summarized as;

$$Y = c(X - X \sim (d)) + (1-b)X \sim (d) + bM$$

Where the output image Y is obtained from the original input image S, the 2D low-pass filtered version of the input image $X \sim (d)$, and the uniform desired mean brightness M which is usually chosen to represent a mid level intensity. In its simplest form, d, c, and b are user controlled constants, d (detail) specifies the 2D low-pass frequency cutoff, and c (contrast) and b (background) are numeric factors in the equation. Considered as a convolution operation, d is the effective kernel size.

The low-pass kernel should be gaussian and radially symmetrical to avoid visible artifacts. Convolving the original image with the low-pass kernel produces an unsharp version. Subtracting it from the original produces a difference image which can be amplified without saturation, with the contrast factor c and the offset M added. The result contains an amplified version of only the high spatial frequency information as determined by detail.

For ease in interpretation, the resulting amplified image can be combined with the original image by adding a weighted percentage of the value from each at each pixel. In the current application, this gives the appearance of curvilinear features being superimposed on the original image.

Feature Characteristics

Systematic analysis of imagery from 3D/IR sensors produces curvilinear features created by thermal sources internal to the body and by texture variations external to the body. Some of the features are universal to all persons and form the basis for detecting the presence of a human in the imagery. Measurements of the features present can be used to characterize the person. Characterizations that are sufficiently similar within subpopulations but distinct among subpopulations form the basis for classification of a person into one or more partitions of a database. Defining a collection of features that is unique for each person in the database and a method for comparing two collections provides recognition capability. Producing one or more templates that correspond to a particular person's unique collection of features and a method for comparing templates provides an identification capability. Transforming the templates into an encoded form that preserves uniqueness while reducing the computational complexity of comparison provides personal ID codes.

Each feature is extracted from the infrared image by analyzing temperature variations over local areas of the image, where the size of the areas investigated is smaller than the spatial extent of the expected features. Localized adaptive filters are used to determine the position, extent, and shape of the features. Depending on their size and shape, features are represented as standardized lines or spots using erosion, curve fitting, and pattern recognition techniques. Spots are considered to be short segments. Reference features are used to scale and orient the collection of lines segments to a standard format depending on the area of the face imaged. The standardized line segment collection represents a binary encoding of the infrared face image. The encoding can be compressed by reducing the scale, by run length encoding, by representing line segments by end points, angles, and lengths, or by other techniques. The encoding provides the identity of the person.

Standardized Pose

In the most general case, analyzing images from a portion of the body will not involve areas having natural symmetry. In order to standardize such images, 3 landmark points in an image are selected to define the standard plane for the portion of the body imaged. That plane is then transformed through three-dimensional space into the two-dimensional image plane of the standardized image to be displayed, recorded, or printed. Definitions for the center position and angular rotation are also established for each portion of the body. Unless otherwise detailed, the centroid of the symmetry plane definition trianguloid will be the center of the standardized image. Angular orientation of the standardized image will mimic the orientation of that body portion when the subject is standing upright with arms above his head palms facing forward. An alternative standard will have arms extended to either side with elbows straight and palms facing forward. Other conventions may be used if established to form composite whole body models such as orienting major arteries to be vertical. The process of orienting images of part of the body to fit either of those whole body positions will be called body-centric standardization in this document. If the size of areas imaged is small relative to the whole body model, images can be rearranged to fit other conventions than the primary one described.

Combining the collection of elevation and infrared images provides true metrics, allowing volumetric and distance measurements to be made directly and compared over time. The precision with which measurements can be made depends on the precision with which reference points can be specified. Landmarks referenced in elevation, visual, or thermal images of the human body commonly are multi-pixel clusters associated with easily defined locations such as the outer corner of the eye, or the nostril. The range measurement associated with eyes or nostrils may be indeterminate when the range sensor is structured light or a laser radar; absorption of the range illuminator provides no return of elevation measurement within those landmark areas. Interpolating an elevation value from surrounding pixels creates a synthetic value that varies with aspect angle.

True metrics and standardization of pose based on anatomical structures results in facilitated ability to perform change detection in IR imagery as well as other modalities of imagery taken simultaneously to the IR with sensors calibrated to the 3D-IR. Advantages of using IR for standardization of any medical image modality include that IR is passive, non intrusive, does not require the use of dyes or special lighting, is cheap, universal, portable, simple to use, and safe. In addition, the microfeatures that can be extracted from 3D/IR provide precise and repeatable landmarks for registration and repositioning. To obtain landmarks on the skin surface, either a lower sensitivity thermal imager is used, or the thermal image is thresholded as to size, location and intensity of features such that those resulting from deep features are eliminated. To obtain landmarks below the skin surface, triangulation is used by taking multiple 3D/IR images from different aspect angles. The shift in position of a thermal feature pixel relative to points on the skin surface indicates the apparent depth of that pixel.

The method of the present invention uses skeletonized vascular features derived from thermal infrared images to define subpixel landmarks located at specific major anastamoses of blood vessels. Although blood vessels may subtend several pixels in width, and their diameters may vary with drugs, medical condition, exercise and other influences, the skeletonized representation is significantly more constant. By defining specific blood vessel branchings common to every person, vascular-centric standardization of any area of the body may be performed. Prior patents of the same inventor deal with the use of minutiae defined in this way for standard positioning and registration of patient images, and for sensor fusion. The improvement of this current invention is the use of three-dimensional thermal imaging to define landmarks, and use of three landmarks to define a standardization plane and rotate into standard pose in three dimensional space.

As in the cited prior patent of Prokoski, a set of landmarks common to all persons can be used to morph portions of one person's image to allow direct comparison with another person's image. However, in the present invention the use of an elevation sensor provides true 3D positions for each landmark, allowing direct determination of the 3D vector required to overlay each of the corresponding landmarks in the two images.

Prior to skeletonization, the thermal infrared image is processed to remove bad pixels and spurious noise. Adaptive local equalization is performed to emphasize areas of the skin overlaying blood vessels. Because blood vessels vary in depth, sometimes going beneath muscle, bone, or other vessels, simple edge detection or contrast enhancement does not provide continuous features. Adaptive local equalization improves the continuity of features while enhancing their visualization. Thresholding the results creates a binarized network of features that are then skeletonized to produce the one pixel wide features used to establish landmarks for standardization and used to construct an identifying code based on 3D minutiae Nomenclature A body-centric coordinate system is used for the standardized image model. For the whole-body model, the subject is assumed to be horizontal laying on back or chest with arms straight and extended above the head. The (0,0,0) origin is on the skin surface overlaying the node at the branching of the aortic arch and subclavian vein. Vertical axis runs through the branch point into right and left common iliac. Horizontal axis is oriented perpendicular to the vertical axis.

Major regions of the body each have their own defined axes, as do subregions and segments. Each division also has three specified landmarks used for standardization, plus multiple aggregation nodes for combining divisions into larger standardized divisions.

Major body regions include: head, upper trunk, lower trunk, L/R arm, L/R leg, L/R hand, L/R foot. Subregions include: ear, heart, groin muscle, shoulder, finger, knee, face. Segments include: finger tip and nose. The size of the subregion imaged is determined by optics and detector specifications. If the entire body were to be imaged at the finest level of detail, the three landmark points for each segment would define a facet and the totality of all facets would form a 3D segment mesh whole body model. Subregional and regional whole body mesh models are composed using the larger facets. Smoothed models are also defined at each level by replacing edge discontinuities by smooth transition curves.

In addition to anatomical regions, analysis regions may be of any size and location on the body. They take the axes and landmarks of the overlaid regions including aggregation of regions to produce a size equal to or greater than the analysis region. Examples of analysis regions are the outer limits of: pressure ulcers, burns, and surgical wounds.

Production of 3D/IR Feature Maps

3D/IR Feature Maps are produced through the process of:
1. Obtaining simultaneous infrared, range, and visual images of a portion of the human body
2. Performing intrinsic calibration of each imager to compute its intrinsic correction transform for lens aberrations, radial distortion, detector array nonregularities, and other biases in its output image
3. Performing extrinsic calibrations of the two imagers with lowest (x,y) sample density against the third imager to obtain each's extrinsic overlay transform
4. Combining the corrected and overlaid infrared and range images to produce a 3D infrared model
5. Processing the range image to extract curvilinear feature map of external anatomy
6. Processing the infrared image to extract curvilinear feature map of internal anatomy
7. Processing the infrared image to extract curvilinear feature map of external anatomy
8. Skeletonizing the curvilinear feature maps
9. Designating skeleton node maps by anatomical origins of branches
10. Labeling each node according to a standard node map
11. Forming a layered composite image of the infrared, range, and visual images, plus their feature maps, plus their skeletonized feature maps, plus their node maps
12. Selecting nodes corresponding to three reference points designated for that body segment
13. Transposing the composite image such that the three reference points define the 2D image plane that is defined as the standard pose for this body segment
14. Storing the resulting standardized composite image as a labeled facet of a total 3D body map
15. Repeat steps 1-14 for additional body regions, subregions, and segments Localized adaptive filters are applied to images of the human body obtained from 2D and 3D imaging sensors to enhance visualization of the vascular structure and other curvilinear anatomical features, including both external and internal features. Standard reference axes are established and images are transformed into standard positions based upon the relative positions of anatomical landmarks. An initial set of enhanced features is selected. Corresponding images from a second sensor may be similarly processed to determine the anatomical source of each feature and establish a reduced set of enhanced features to be further utilized.

Various stimuli can be used to verify the designation of veins vs. arteries, and to enhance the visualization of features and nodes. These include: warm and cool air flow; contrast dyes; vasoactive medications; hot and caffeinated beverages; induced exercise; massage to stimulate lymph flow.

Refined BodyMapping is process of:
1. Performing BodyMapping of one or more body segments
2. Changing parameters of the imagers to obtain higher spatial resolution over smaller fields of view (subsegments and elements)
3. Obtaining simultaneous images of subsegments or images at the same point in cardiac/respiratory cycles
4. Performing Body Mapping steps 2-14 above to create labeled subfacets
5. Repeat Refinement steps 3&4 for additional body subsegments where refinement is desired
6. Repeat Refinement steps 1-5 until the desired level of refinement has been reached for each area of the body Standardized Faceted Body Models are used for comparisons with 2D imagery such as x-rays. Facets are aggregated until a single facet represents the area to be compared and the pose is matched to the comparison imagery. Standardized Smooth Body Models are used for comparing with 3D imagery such as MRI, CT, and previous 3D/IR models.

Identification: Classification, Template Matching, Encoding

The second object of the present invention to provide a method and apparatus for identifying individuals from biosensor data. A 3D thermal image of a portion of the individual's body is generated and is processed to produce a set of line and point features, together with characteristics that describe each such feature and its relation to other features. That combination of features and annotations is considered unique to the individual and essentially persistent in spite of ambient, physiological, emotional, and other variations that can be modeled as temporary distortions to the mesh formed by the interconnected features and the surface thermal map.

Any portion of the body can be utilized for ID, but the face is generally preferred due to its availability. Since parts of the face may be blocked by glasses, facial hair, or orientation to the sensor (camera), a useful system and method must allow for identification based on partial faces. The face may be partitioned into areas, where corresponding areas of known faces are matched. This will accommodate matching of partial faces when faces are partially disguised or hidden behind other faces in a crowd.

A major technical challenge to successful scaling of IR-ID technology for very large populations is determining which temperature variations represent unique identifying information and which reflect inherent variabilities in the temperature of the human skin surface due to physiological cycles (heart, respiration, metabolic), changing ambient conditions, and sensor noise. Because the array sizes of commercial IR cameras are relatively small compared to visual sensors and certain range sensors, the impact of variabilities in IR sensor data caused by bad pixels, loss of calibration, noise, ambient thermal currents, etc. is magnified.

Three approaches to 3D/IR-ID are offered; namely curvilinear feature maps, minutiae, and encodings. ID from feature maps considers classification by total lengths of horizontal and vertical features, angular distribution of the features, distribution of lengths and angles across some number of areas of the face. ID is then performed based on the total length of overlaying feature structure between the two standardized images. A string of values is computed corresponding to the total overlaid length when different tolerances are allowed in the position of "overlaid" areas. Tolerance value is selected based upon quality of the imaging sensors used.

ID from minutiae uses classification by distribution of minutiae across the areas of the face. ID Is then performed based on the percent of minutiae in the unknown image that lie within a tolerance radius of minutiae in the known image. Only minutiae from internal features are used. Type of minutiae can also be matched but the additional processing time is generally not warranted.

ID from encoding does classification using the cell code of the three standardization landmark points used to standardize the image, and the ratio of distances among the three points. ID is based on the number of face cells having the same code as a candidate matching image. The current code distinguishes 7 types of vascular branching and seven topographic gradients within a cell represented in an alphabet of 49 symbols. An additional symbol can be used to distinguish between veins, arteries, and other features.

ID matching against a database of visual images performs classification based on metric ratios of the distances between external skeletonized feature map nodes in the 3D/IR feature map and corresponding points in the visual image. The 3D/IR image is transformed into the same pose as the visual image prior to metric extraction. Allowance is made for the imprecision in selecting landmarks in the visual image, and for possible cosmetic and worn disguises in the visual image database. Cross-spectral identification cannot distinguish identical twins. Matching is not one-to-one but rather is a process of eliminating impossible matches based on anatomical rules as in Prokoski U.S. Pat. No. 6,751,340; a systematic process for eliminating individual visual images classified the same as the IR image. The process involves exclusion of all impossible matches and estimation of the probability that each remaining Visual image is from the same person seen in the IR image. An unknown IR-image must be in the same partition (classification) as a Visual image, the percent of external line feature lengths from the IR image that overlay the corresponding features in the visual image must be above a threshold, no IR vascular feature can cross a Visual feature edge, and anatomical rules relating to thermal contours must not be violated. If all that holds true, the IR and Visual images may be a match. A measure for the degree of confidence in that match is developed taking account of: quality of the images, difference in aspect angle, percent of overlaid features, and possibly other factors.

Various perturbations, such as facial expression changes, can distort the relative locations of features and line segments to an extent. This is analogous to the deformations that occur in fingerprints due to movement between the fingers and the print surface. The line segment matching algorithms must allow for variations in the position and characteristics of the segments, as well as in the subset of segments in the overall patterns which are seen due to the field of view of the camera and to possible obstruction of certain areas of the face in the image.

In the 3D/IR-ID embodiment, facial feature map is referenced to specific subsurface anatomical elements. Although many different approaches may be used to obtain repeatable features from 3D facial thermograms, the preferred approach uses a number of extraction routines to produce a plurality of features sufficient for an intended purpose. Thus, for a relatively low order of required security, fewer coarser features may be extracted using very simple computations. For a very high security requirement, more detailed features may be extracted using additional computations. The method for 3D/IR ID based on classification and pattern matching involves the following steps:

1. Collect calibrated IR, range, and (optional) visual images
2. Extract Curvilinear Features from each image
3. Skeletonize Curvilinear Features and Extract Minutiae
4. Construct 3D/IR model of Imagery, Features, Skeletonized Features, and Minutiae
5. Transform the model into Standard Pose
6. Classify the model and characterize the features
7. Select partition of Reference Database
8. Perform 3D Template Match of Curvilinear Features or their Skeletons
9. Compute percentage of Overlapping Pixels
10. Assign Probability of Match Alternately, the method for 3D/IR ID based on Face Encoding substitutes the steps:

7. Produce the FaceCode for the Standardized Model
   8. Aggregate portions of the FaceCode from a sequence of images if available
   9. Assign a confidence measure to each element of the FaceCode
   10. Compare against an ordered list of FaceCodes of interest
   11. Tag the image files with the FaceCode and link to the FaceCodes of others in the same image sequence Where the Pose Standardization transform of step 7 utilizes bilateral symmetry, landmark selection, or a combination of the two; and is applied to the calibrated images, their curvilinear features, or their skeletons depending on the ID method chosen.

Where the Classification of step 6 can consider any or all of the following aspects:

1. After 3D/IR image standardization and feature extraction, classification, matching, and FaceCoding can be performed based on a combination of IR features, Range features, and Visual features.
2. Skin pixels in the IR image are distinguished from hair, clothing, and background pixels by range gating to eliminate background pixels, visual color and/or IR temperature to eliminate clothing pixels, and IR temperature and/or range data to eliminate hair pixels or, alternately, to paint them as hidden points.
3. Internal vs. External Features are determined by comparing features from IR images with those from Range and Visual images. External Features will appear in Range imagery and possibly Visual imagery whereas Internal Features will appear only in Infrared imagery. This distinguishes Vascular Features from Skin Folds in the IR imagery.
4. Encoding can utilize horizontal and vertical filtering to aid fast standardization by separate consideration of bilateral symmetry of external features in the IR imagery and Range imagery such as the eyes, nose base, and mouth which are primarily horizontal, and external features in the IR and Range imagery such as labial skin folds along the nose and mouth which are primarily vertical. Computing symmetry axes from those features, or from their binary skeletonized form, is much faster than computations involving grayscale values of the total images.

5. Comparison of elevation and visual images is used to determine differences in external features as seen by the two sensors to automatically detect possible disguise through cosmetics or appliqués.

6. Feature widths can be maintained rather than skeletonized to retain information on condition or changes in condition of specific vessels. Alternately, feature width can be used to encode the possible range in position of the feature as a function of body movements or imprecision in the extraction process.

7. Feature Template stored as the ID can include standardized features, skeletonized features, filtered feature segments with widths as stated in 6, compressed version of feature map from downsampled, compressed version using techniques known to the art such as run length encoding, or encoded version that uses an alphabet of characters representing various vascular branching patterns that could occur within subareas of the feature pattern.

8. Images and Templates and Encodings can have the actual dimensions of the body area imaged and can be put into standard orientations in three dimensional space as defined by anatomical landmarks common to all persons. Alternately, for use in reference libraries or for comparison to imagery for which true metrics are not available, they can be scaled to a standard and annotated with standard reference points or landmarks. When the face is the area being used for identification, scaling to a constant distance between outer eye corners or between pupils in the front-facing face is preferred when only frontal images are to be recognized. Scaling to a constant distance between eyeline and mouthline is preferred when faces at any rotation angle are to be recognized. Centering the frontal images at the midpoint between the eye features is preferred by most current face recognition systems. However, that has utility limited only to images in which both eyes can be seen. Instead, centering should be done for the face as for other body areas: with the centroid of the standardization trianguloid being the face center.

9. Thermal features can be considered to be imprinted on the skin surface which is represented by the three-dimensional elevation data. Or, thermal features can be considered true 3D elements beneath the skin whose mage representation varies with aspect angle.

Blum's Medial Axis Transform (MAT) has been used for more than 30 years for analyzing shapes in spite of its difficulties achieving consistent results with even very small changes to an object's boundary. Katz proposed consideration of both substance and connection when decomposing an object into a hierarchy of parts that appears natural to human observers. He presented a method for separating the substance and connection information of an object. This provides a natural parts-hierarchy while eliminating instabilities due to small boundary changes. The method also allows for graded, fuzzy classifications of object parts to match the ambiguity in human perception of many objects.

Blum's Medial Axis Transform (MAT) represents the skeleton of an object as well as the width of the object at every point on the skeleton (Blum, 1967). Research has followed into the use of the Blum MAT and other skeleton representations (Blum and Nagel, 1978; Brady and Asada, 1984; Bruce et al., 1985; Ogniewicz and Ilg, 1992; Pizer et al., 1987; Pizer et al., 1998; Szekely, 1996). Many of these projects have been directed towards producing a natural decomposition of an object into a set of basic parts with full shape information about each part as well as the whole object.

For purposes of identification, the changes to skeleton segments that occur with 3D/IR image analysis include slight translation or variation in segment angle due to: body pose or activity, change in blood pressure, significant weight change, drugs such as steroids, and water retention. The methods used for comparing skeletonized images must allow for expected deviations while disallowing changes that could not occur in the same person. One approach is to determine a reachable range of locations for each skeleton node based on the area of the body. For example, nodes in the facial skeleton that are in the area of the mouth would have greater allowed variability in position than nodes in the forehead since the mouth has greater degree of change with expressions, speech, and other movements than does the forehead.

For template matching of skeletonized thermal features, the size of nodes can be increased commensurate with the variability expected at each node site. Segment width can be likewise increased to accommodate the variability at each node connected by that segment. Alternately, color or grey levels can be used to encode the actual feature width prior to skeletonization, and/or the expected variability in position at each node or segment pixel. Rather than template matching, elastic graph matching techniques can be used as described in earlier patents of Prokoski.

It is a goal of each embodiment of this invention that higher performance imaging sensors can be implemented while still matching against feature maps derived from lower performance sensors. In the case of skeletonized features, higher performance sensors may yield additional finer details producing sub-branchings not seen in the feature sets from the lower performance sensors. Pruning of the higher performance skeleton trees may produce better matching results against lower performance sensors. When the higher performance sensor has higher spatial resolution and greater thermal sensitivity, its skeletonized feature map will in general display greater connectivity, more skeleton pixels, more segments and more nodes. Matching against lower performance sensor maps may be enhanced by directed pruning or sequential segment matching. This approach selects the widest features in each image and compares those first. Then the first order branches off those features are compared, followed by successive rounds of segments further and further from the originally considered widest features. Progressing from widest to finest segments is equivalent to progressing from hottest to least hot segments because both veins and arteries decrease in diameter through successive branchings. Vessel segments can appear to increase in temperature or size when the vessel proceeds closer to the skin surface, even though the temperature and size are in face decreasing. Lower spatial resolution sensors are less capable of distinguishing between depth and size variations.

Current 3D/IR systems perform positive identification of persons at distances of 2' to 60' with variation in head pose. Analogous to partial latent fingerprint matching, 3D/IR feature map comparisons can identify based on a partial face image. Frame sequences of moving-head subjects can be aggregated into a more complete 3D model. Automatic reconstruction into standard poses aids recognition against existing file images of 2D or 3D visual or IR images.

Identification by matching against large databases in realtime may require the intermediate step of classification. By using classification to partition the reference database into 100 or more divisions, unknown images may be classified and matched against images in the selected partition in less than a second. Classification of a database of faces is done based on statistics of feature lengths globally or in terms of distribution over the face, where the standardized infrared facial image is divided into local areas overlapping or not.

Various classification schemes are based on: (a) statistical distribution of IR and topographic feature metrics across the face, (b) level of IR and topographic bilateral asymmetry in regions of the face, (c) statistical distribution of feature types across the face. For structural segments: metrics include lengths and angles of unbroken segments; types include external, internal, and artificial. For minutiae: metrics include number of minutiae and angles of the structures defining each minutiae; types include end point and branch point. To be effective in an automated system, classification must be immune from variables such as head rotation and ambient temperature.

A 3D/IR face map put into standard pose can be divided into a matrix of cells, overlapping or not, such that within each cell there is at most one vascular branching and one predominate topographic orientation. The cells need not all be the same size, but processing is simplified when they are. Three standardization landmarks are defined for each of 0, +/−45, and +/−90 degrees of head rotation. The total face encoding represents a 2D projection of the cell structure from a 360 degree wraparound image after standardization into each of the five poses. In general, only a portion of the encoding will be obtained from an image sequence that will be standardized into the nearest of the five poses.

Encoding of feature maps provides for highly efficient ID against very large databases. Various schemes can be used to produce an ordered code based on thermal and topographic feature maps. Examples are: (1) binary codes which divide the standardized IR face into a matrix of cells and set a bit in each cell based upon whether or not a minutia is present (2) alphabetic codes which set a character in each cell based upon the number and type of minutiae present. (3) symbol codes which set one symbol in each cell representing the IR feature map branching pattern in each cell and the topographic orientation of the skin surface in that cell. (4) interpolation of the standardized IR feature map to a smaller array size. (5) run length encoding of the skeletonized standardized feature map with or without size reduction. These examples rely upon precise standardization and cell division of the facial images. To the extent the standardization and/or cell division is imprecise, fuzzy logic matching can improve identification accuracy.

Comparison of Images from Same Person

The third object of the present invention to provide a method and apparatus for detecting and assessing changes between medical images; including images of different people from different imaging modalities.

Medical Images

3D/IR feature maps and minutiae extracted from a sequence of images of a person are individually pose standardized using three minutiae designated for the particular region, subregion, or local area imaged. Rhythmic expansion and contraction of the three minutiae relative to their center point reflects respiratory and cardiac cyclic motion which may also be accompanied by cyclic thermal and color variation. The movements and thermal variations can be analyzed to provide pulse and respiration rates. The related movements can be filtered out to produce images that are not only pose-standardized but also standardized as to cardiac and respiratory motion. This double standardization permits more precise extraction of episodic movements and changes in local temperature, color, and elevation. Such changes accompany tics, tremors, shivering, microfacial expressions, blushing, goose bumps, pore dynamics, muscle spasm, hairs standing on end, and sweating. When controlled stimuli are used to produce these effects, the magnitude and timing of the effects are then compared against reference profiles to assess physiological condition and psychological state.

Images taken periodically of the same person are standardized and compared to track changes automatically. In the example of wounds, particularly pressure ulcers, certain areas of the skin are highly susceptible to developing such sores which can rapidly advance to pose fatal risk. Routine 3D/IR-Visual imaging of those areas at least daily can provide automated early detection of incipient pressure ulcers prior to visible color changes occurring at what is deemed Stage 1. The automated pressure ulcer management system automatically standardizes images of the areas considered susceptible, detects local anomalies in color, elevation, and thermal properties; detects bilateral asymmetries in those properties within one or more images; and tracks changes larger than specified dimensions to calculate quantified values including: perimeter, surface area, elevation, volume, color, temperature, texture, level of hydration, motility.

Early detection of incipient pressure ulcers is a key factor in reducing the time, cost, and discomfort of wound healing. Indications of a Stage I ulcer may include: nonblanchable erythema of intact skin, local variation in skin temperature, edema, induration, or hardness. The combination of infrared and laser radar imaging can provide a realtime three-dimensional topographic model of the skin surface indicating surface variations as small as 0.01 mm and thermal variations of 0.02° C. with current sensors. Bilateral asymmetries and local anomalies of the thermal-topo map may be indications of underlying damaged tissue. Rapid image sequencing and frame-to-frame variations during respiration, heart, and lymphatic cycles may further enhance detection of unhealthy tissue. Analysis of 3D/IR time sequences during and after use of a calibrated weight to depress a specific area of the skin provides quantitative measurement related to edema, induration, and hardness to improve early detection of incipient pressure ulcers prior to Stage I.

Previous studies have considered the use of thermography for detection of pressure ulcers. The skin temperature of incipient ulcer sites detected by appearance of redness near load-bearing bony prominences (Stage I ulcer) has been found to differ from nearby healthy tissue and from the contralateral site by of 0.5° F. or more in 88% of patients tested in small studies. But the ulcer site may be either warmer or cooler than the reference areas. Temperature may increase due to inflammation response of a pressure ulcer to increased circulation to the tissue—or temperature may decrease as a result of damage to the microvasculature. Studies by Newman and Davis found localized warming in only 57% of patients, with 26% showing cooling and the remaining 12% showing no temperature difference at the 0.5° F. level of sensitivity. Temperature mapping of the skin surface has therefore been shown to have some utility in detecting possible locations of Stage I pressure ulcers, especially in people with darkly pigmented skin where redness might be less noticeable. However, temperature mapping alone has not been shown to be an effective primary method for consistent, automatic, accurate early detection.

Four conditions contribute to the development of a pressure sore: pressure, friction, shear and moisture. Pressure sores can usually be attributed to a combination of these conditions. Each of the four causes localized thermal differences that may be small and temporary, but can be detected by current radiometric thermal imagers. In addition, friction and shear produce local changes in skin texture that may be small and temporary, but can be detected from a precise topographic image. Moisture changes the emissivity of the skin, which is detected in the IR image. Prolonged exposure to moisture causes localized change in skin hydration that increases the risk of shear damage. It can be detected and localized using other optical sensors calibrated to the 3D/IR.

Previous studies have considered the use of thermography for detection of pressure ulcers. The skin temperature of incipient ulcer sites detected by appearance of redness near load-bearing bony prominences (Stage I ulcer) has been found to differ from nearby healthy tissue and from the contralateral site by of 0.5° F. or more in 88% of patients tested in small studies. But the ulcer site may be either warmer or cooler than the reference areas. Temperature may increase due to inflammation response of a pressure ulcer to increased circulation to the tissue—or temperature may decrease as a result of damage to the microvasculature. Studies by Newman and Davis found localized warming in only 57% of patients, with 26% showing cooling and the remaining 12% showing no temperature difference at the 0.5° F. level of sensitivity. Temperature mapping of the skin surface has therefore been shown to have some utility in detecting possible locations of Stage I pressure ulcers, especially in people with darkly pigmented skin where redness might be less noticeable. However, temperature mapping has not been shown to be an effective primary method for consistent, automatic, accurate early detection.

Four conditions contribute to the development of a pressure sore: pressure, friction, shear and moisture. Pressure sores can usually be attributed to a combination of these conditions. Each of the four causes localized thermal differences that may be small and temporary, but could be detected by current radiometric thermal imagers. In addition, friction and shear produce local changes in skin texture that may be small and temporary, but could be detected from a precise laser radar image. Moisture changes the emissivity of the skin, which is detected in the IR image. Prolonged exposure to moisture causes localized absorption, which could be detected from the laser radar image, and increases the risk of shear damage. The progress of wound healing and the effect of clinical treatments can be monitored by measuring the volume and area of the wound. Measurements taken via manually based methods, such as using a computer pointing device to delineate the wound boundary in a digitized image, suffer from variations due to manual dexterity and differences of opinion between observers. 3D/IR provides a consistent, automated set of true measurements of perimeter, area, and volume.

3D/IR produces surface information from subsurface anatomical structures and processes, primarily vascular and lymphatic networks and their rhythmic changes resulting from respiration, heart, and lymphatic cycles. Both temperature and elevation (relative to a static anatomical reference) at a given location on the body vary minutely during these cycles. For early detection of pressure ulcers, processing of the imagery must factor out those changes. However, other important applications exist in which those variations provide significant information.

3D/IR standardized imaging with change detection provides automated quantitative measurement of lymphedema, and is used to generate 3D maps for customized pressure garments—especially useful for areas such as the chest and groin that are difficult to measure precisely using current techniques. The non-contact, rapid nature of the 3D/IR imaging provides precise quantitative measurements, throughout the breathing cycle, and in various positions. It precisely determines the extent of bilateral asymmetries and tracks changes following radiation treatments, surgery, PT, and use of compression garments.

Other diagnoses and treatments that rely on visual observation of redness, rash, swelling or other changes in texture of size of anomalous areas might also benefit from IR/LR imaging. Among these are:

Burns assessment and debridement

Detecting growth or irregularity of moles

Detecting ticks, bee stings, flea bites, rodent bites on infants and elderly patients Early indications of infectious diseases, including monitoring of people in quarantine Early indications of adverse reactions to smallpox vaccine or other allergic reactions Monitoring wound healing for signs of infection Detecting and documenting physical abuse to those incapable of self-reporting.

The noncontact, risk-free nature of 3D/IR imaging offers particular utility in telehealth applications, reduces health care workers exposure to infected persons, and reduces the creation of biohazardous waste associated with contact procedures. Portable 3D/IR systems carried by health care providers or installed in a home and linked to a service bureau reduce the need for routine doctors' visits to check vital signs, monitor wound healing, control of diabetes, circulatory system functioning, skin disorders, and other chronic conditions. The combination of more frequent routine scanning, plus automated detection of significant changes from prior imagings, plus avoidance of the stress and hardships associated with getting to the doctors' office provides earlier and more accurate detection of serious conditions that require visiting a medical facility. This approach is especially valuable in rural and other areas underserved by health care providers, reducing the disparity in quality of care provided to certain subpopulations.

Biometric Images

Automated patient ID is an important issue currently addressed mainly by wristbands and ID photos for patients within a facility. At admission, ID photos and insurance cards are primarily used although they provide weak protection against fraud. Other biometric techniques such as fingerprint and iris scans are difficult and error-prone for elderly or infirm patients. 3D/IR is a convenient, foolproof, universal identification method that uses any undamaged area of the skin surface for positive ID.

3D-IR imagery derived from (RGBXYZT) calculations provides consistent and precise feature maps of any area of the body. The complexity and density of the features assures uniqueness of each person's patterns. Although any sizeable area of the skin surface provides positive identification, the face is used when a sufficient portion is free of obscuration and recent injury. The 3D/IR image is standardized to frontal, three-quarter, or profile pose using the three-point standardization landmarks defined for the available subregion of the face. Feature and skeletonized feature maps are extracted. IR features are determined to be external or internal depending on whether they do or do not overlay topographic edge features. Internal features are further characterized as: vein, artery, or other based on whether they exhibit monotonically varying temperature along their length, and whether the decrease is away from or towards the heart. Monotonically decreasing temperature from the heart is characteristic of an artery. Monotonically decreasing or constant temperature towards the heart characterizes a vein. Arteries exhibit slight thermal changes synchronized with cardiac pulse, which veins do not. Arteries are most routinely detected via ultrasound. Once feature maps have been annotated for a given patient, the annotations can be applied to future image collections.

Feature extraction and classification provide intermediate step towards identification. A Face Classification Code may contain sufficient information to eliminate the need for further processing of a particular image. Or it may partition the total database such that only a sub-portion needs to be compared against the full Face Identification Code. Classification of arterial and venous patterns, and their symmetries, can significantly increase the speed of 3D/IR identification for many applications.

A person's levels and planes of visual symmetry, thermal symmetry, and topographic symmetry are different. Given the region of interest can be defined specifically and repeatedly, the three symmetry waveforms, or a combination of them, can be used for classification against large databases or for identification against smaller databases.

Current face recognition methods that utilize range imaging generally determine the closest area of the face to be the nose tip or chin, depending on the distance and relative aspect angle of the face to the imager. The size of the nose tip defined by range data is on the order of a circle with diameter ¾". The chin area is somewhat larger.

Range imagers that provide measurements of range with precision to 0.08 mm may provide 640×480 samples across the image plane. Possible landmarks in range images include the pupils which absorb laser illumination used for structured light sensors—producing "black hole" effects in the resulting point cloud data. Depending on imaging distance the pupil area may be 5 pixels or larger. Similar effects may occur for nostrils if the imager is looking upwards at the nose. The nostril area may be 12 pixels or larger. The aspect angle of the camera relative to the nostrils, and the shape of the particular subject's nostrils, determines the size and what structures within the nostril area will be observed.

Changes to a person's range image, due to a cold sore, swollen toothache, drug side effects, water retention, facial expression, speech etc. are in general not symmetrical and may be a few millimeters in magnitude. The effect on symmetry axis calculation and the local effect on the range map itself may lead to a mis-identification. To mitigate those effects, areas showing local thermal anomalies may be omitted from range symmetry waveform analysis, and vice versa. In particular, thermal anomalies showing time variations can be considered transitory regions.

Human faces are generally more bilaterally symmetrical in elevation than in infrared, and more symmetrical in infrared than in visual images. Each of the three sensor modes has vulnerabilities: Elevation is affected by local swelling, facial hair, stubble, water retention, muscle fatigue, facial expressions, weight changes, and other conditions. Thermal infrared and visual images are affected by those same changes projected to two-dimensions. In addition, thermal infrared images are changed by local and overall temperature changes that can be caused by internal or external influences. Visual images are affected by changes in lighting analogous to the effects of external temperature on infrared images. In both cases, the effect can be a change in the symmetry of the face as measured by the sensor. When imaging other areas with inherent symmetry, such as the upper chest, a greater degree of repeatability may be obtained for the symmetry axes.

Other face recognition methods using visual, infrared, range, or a combination of those sensors rely upon finding the eyes or pupils, then orienting the face image to make the eye line horizontal. However, an estimated 8% of people have eyelines that are not horizontal; one eye is higher than the other relative to a symmetry plane computed without eye data. In most of those methods, it is assumed that the face symmetry plane is perpendicular to the eyeline, and bisects the nose. However, an estimated 11% of people have a nose that is not parallel to the face symmetry plane computed without nose data. And an estimated 12% of people have face axes that are not perpendicular.

Many face recognition methods designate the center of the eyeline as the center of the face. Transforms which de-skew the face in 2D images, or standardize roll, pitch, and yaw in 3D images by centering on the mid-eyeline position, forcing eyelines to be horizontal, and assuming perpendicular face axes do not truly represent all members of a population. The result of performing those transformations is increased risk of error in identification when matching against databases that perform normalization differently. Furthermore, when the match is performed by human observers, there is an unknown influence on the perception of the observer. This can include human screeners such as customs agents who select persons from crowds for additional security inspection. Also it can include eyewitnesses selecting suspects from digital lineups.

When composing digital lineups, many states make use of driver license photographs to fill the required number of candidates. When eyewitness reports mention characteristics such as hooked nose, pointed chin, crossed eyes, the filler photographs may be digitally manipulated to have those characteristics. Eyewitnesses have selected manipulated filler images and in a number of cases the selected individual has been convicted based on the eyewitness testimony in spite of the fact his photo was chosen as a filler and the eyewitness selected a digitally manipulated version of that photo. Many studies over many years have quantified the poor reliability of eyewitness testimony; yet it remains a mainstay of our jury system of justice. Eyewitnesses who have selected a manipulated image of a filler candidate suspect when faced with the actual candidate will often maintain their testimony that that candidate committed the crime. If the eyewitness appears truthful and forceful, the jury may convict the filler candidate. Therefore care must be taken when human decision makers rely upon images that have been manipulated using techniques designed for computer processing.

Many studies have linked facial symmetry to the perception of beauty, and beauty to perceived exceptional goodness. Other studies have correlated the range of facial attractiveness from gross deformities to simple ordinariness to expected behavior ranging from deviant to good. Therefore, the risk induced by arbitrary use of standardization processes is not just the mis-identification of persons. While that alone is a significant problem, perhaps the greater risk lies in the mis-classification of persons based upon human perception biases as embodied in profiling techniques that screen persons for scrutiny based upon physical characteristics. The methods of the present invention provide classification and identification of persons without reliance on outward physical characteristics associated with attractiveness, skin color, age, ethnicity, or gender.

Furthermore, current face recognition methods that rely upon symmetry for standardization do not take into account faces that are asymmetrical inherently or episodically as a result of illness, disease, disguise, or injury. This limits their accuracy against very large databases of reference images, and also limits the utility of such standardization methods serving as universal standards for reference libraries of images for medical applications, where asymmetry and anomaly locations are of greatest interest.

Most biometric identification applications capture a current identifying template and then search for its match in a database. Doubly-standardized IR feature maps and minutiae provide the ability to match facial expressions as well as identity, separately from cardiac and respiratory motions.

Facial movements associated with respiration, pulse, blinking, swallowing, expressions and microexpressions, and speech may produce variations in feature maps extracted and classified. Although the movements may not introduce errors for verification tasks or for identification against small database populations, they could create errors in feature map encodings or identification against very large database populations especially when only a small area of the face was available for imaging.

Using a high performance IR camera with fast frame rate reduces the amount of movement during an imaging interval. Frame-to-frame thermal differences combined with node displacements indicate regions of the face involved in recent facial movements. Heat generated by muscle actions is sufficient to be detected in thermal IR imagery, but quickly dissipates once the movement ends. The rapid dissipation distinguishes thermal changes caused by facial muscle movements from thermal changes induced by systemic changes caused by drugs, alcohol, illness, and whole-body exercise. Rather than analyzing the reachable set of locations for each feature map node, identification matching can ignore recently moved nodes or weight their importance less than static nodes.

After pose standardization, 3D/IR feature maps and minutiae extracted from a sequence of images of one or more person's faces can be filtered to yield pulse and respiration measurements, which are indicators of stress in the subject. When more than one person is imaged and the subjects are interacting, increase or decrease in synchronization of those rhythms can indicate change in the level of harmony or disagreement among the group.

After double standardization, residual movements, thermal, elevation, and color changes provide clearer analysis of facial expressions, microexpressions, and speech-related motions. This facilitates speech therapy, training of actors, lip reading, and psychoanalysis. Controlled stimuli can be used to induce the changes, and analysis can separate cardiac and respiratory reaction from changes in facial expression, color, and temperature. The pattern of thermal changes associated with facial muscle activity serve as an expression template for assessing an individual's stimulus response, and for training persons to evince specific expressions with selected strength. The areas of the face warmed by a facial muscle activity are correlated with the particular expression in the same way that Eckman's facial action coding system (FACS) associates specific expressions with specific visible movements of the skin surface overlaying specific muscles.

Comparison Against Image Library

Medical Libraries

To assist in diagnosing a particular patient or for directed research, only a portion of a medical image library is considered at a time. While searches can be constructed using only textual information associated with each image, the intent of the 3D/IR feature mapper is to facilitate rapid image search and compare independent of related textual content, as well as combined image/text searches. A hierarchy is used to direct image searches from general to specific imagery, and from low resolution to high.

A query starts with a generalized description such as: "thorax of healthy middle aged American male of European heritage with no chronic disorder"; or "pressure ulcers on 85 year old African-American woman without diabetes". That query is compared against text associated with each image. Images of the cited areas of the body from persons having conforming text are copied to a query response buffer. An integrated query model is formed by integrating the conforming standardized images. If a comparison to a current patient is sought, each conforming library image is matched against the same modality as the current image. The resulting difference images are saved for display upon request and are combined into an integrated query difference model.

Subpopulation models are formed at the regional or subregional level and are based on imagery associated with a specific query. Head modeling utilizes visual, IR, X-rays and MRI's to determine the extent of variation in the skull, head, vascular and lymphatic structures, soft tissue and exterior skin surface of the face. Digital standardized models are designed to mimic statistical distributions of those features in an actual subpopulation of interest. Associated standardized history includes percent of component subjects with listed traumas, surgeries, on-going medications, chronic conditions, and genetic markers.

In addition to comparing imagery of a specific subarea of a patient's body to corresponding subpopulation images, all available images of the current patient can be compared to all images from the subpopulation. The level and extent of differences between current patient and his selected subpopulation are used to assign a quantitative ranking to the current wellness and risks of a given individual relative to that subpopulation. Since members of the same subpopulation can be expected to share similar medical conditions and histories, continuing comparisons against other members provides a basis for on-going risk assessment and prognosis related to selection of surgical and treatment modalities.

Reference wellness standards for men and women can be developed to represent specially selected actual library entries from subpopulation such as "healthy middle aged American male of European heritage with no chronic disorder"; or "85 year old American woman without diabetes".

Subpopulation reference wellness standard models are then used to assign a quantitative ranking to the wellness and other characteristics of a given individual within that subpopulation. Since members of the same subpopulation can be expected to share similar medical conditions, continuing comparisons against other members provides a basis for risk assessment and prognosis related to selection of surgical and treatment modalities. Subpopulation reference wellness models aid in specific impact assessments of the results of specific diseases, surgeries, and treatments on overall wellness.

Biometric Libraries

A major source of error in facial identification is variability in the designation of landmark reference points in the images. That variability is compounded by subsequent preprocessing to scale, center, de-skew and otherwise standardize the images, which impacts feature extraction and matching accuracy. Small variations in designating the location of landmarks commonly used for face recognition, (such as center of pupil, eye corner, and center of nostril) can cause significant errors in identification particularly when very large databases are involved. If traditional face recognition techniques are applied to infrared images, landmark variability may have significantly greater impact on identification accuracy because the detector arrays used in infrared cameras are small (normally only 320×240 or 640×480) relative to common digital video cameras. Even a one-pixel variation in designating reference landmarks in the IR image can create 2-3% scaling error, variations of 2° or more in defining face axes, and multiple-pixel error in designating the face center. Subsequent processing to compare images having even slightly different poses would introduce additional error.

Those considerations are important when developing infrared ID methods based on comparing structures. They are of greater importance to minutiae-matching methods, and of even greater importance to 'FaceCode' methods as that progression in methodology places increased emphasis on localized feature characteristics. Adding 3D topographic imaging, with pixel-to-pixel overlay on the IR image, provides (1) True absolute measurements eliminating the need to scale images. (2) Automatically designated anatomical landmark locations. (3) Transformation of infrared image into a standard pose with sufficient precision and repeatability to support accurate ID against very large databases.

Identifying a person in real time against a very large database of hundreds of millions of people requires an analysis method which grows at most linearly with the population size. Current fingerprint and visual face identification systems perform classification followed by comparisons between an unknown person's biometric and those of all known database entries. The closest match in the database, if it is considered close enough, is the identification. In the case of iris scanning, wavelet decomposition is used to derive a 244-bit code from the iris pattern. That code is the identification.

Visual face images are classified but not encoded due to the large amount of variability in the visual facial image. In order to differently encode two identical twins, the analysis might need to contain micro-level features. Fingerprints are classified but not encoded due at least in part to the problems of repeatably defining centers in arched prints and specifying axes in latent prints. Encoding of standardized 3D/IR feature maps offers a compact, unique ID such as is provided by iris scanning. The resulting 3D/IR FaceCode can be covertly obtained from long distances, with no light, as the subject moves, without requiring he cooperate.

Face identification can covertly collect facial images from uncooperative subjects and match them against a wide array of existing image databases, including drivers license, passport, school yearbooks, and mug shots. Variations in lighting, aspect angle, age of the image, clothing, hairstyle, and other parameters can create errors in identification matches using visual images against existing databases of visual images. Those variations do not affect 3D/IR to 3D/IR matching.

As taught in Prokoski U.S. Pat. No. 6,920,236 and Prokoski U.S. Pat. No. 6,751,340, IR images can be matched against visual image databases through a process of elimination. First, feature metrics which are coincident (the same in both visual and IR spectra) are extracted from the IR image and used to partition both image databases. Only visual subjects with similar feature metrics are possible matches. For the possibly matching visual images, the coincident features are overlaid by morphing to a standard or to the particular IR image. A series of anatomical rules is then imposed to eliminate further visual images. The first exclusion rule is that the vasculature of the IR image cannot extend into the nostrils, eyes, mouth, or outside the head outline of the visual face. Other rules relate to the relative locations of vascular elements and gross visual features. For example, the ophthalmic artery branches must lie beneath the eyebrows. Folds of skin along the nose, wrinkles in the forehead, moles and scars, may produce features in the IR image which can be matched to visual features seen under certain lighting conditions. In the present invention, the use of 3D/IR imaging allows transposition of the collected image to match the pose of each database image—resulting in greater precision of cross-spectral comparison.

Analogous to the identification of partial latent fingerprints, feature maps of the face provide positive identification even when only a portion of the face is seen. IR images of a partial face may be sufficient for unique identification if enough features or minutiae are seen. Minutiae extraction from 2D-IR images is extended to 3D/IR images. Minutiae associated with vascular branch locations had greater repeatability than end point minutiae when camera, spectral band, facial expression, or ambient temperatures changes occur. When initial head pose is significantly deviated from the standard pose, location of branch minutiae in the pose standardized face may vary due to residual errors in the automated standardization routines. Manual selection of standardization reference points and/or controlled blurring of feature maps and minutiae can improve the percentage of overlap consistently enough to yield 100% identification based on partial facemap comparisons.

Characteristic behaviors of a person can be used to identify him even when insufficient data is available for ID based on 3D/IR feature map. For example, mouth movements during speaking his name may be sufficient for identification of a person, with or without the corresponding audio. While the mouth area alone may not provide a sufficiently unique partial facemap for positive identification, a sequence of local facemaps may be sufficiently unique.

3D/IR Medical Image Visualization

Three-dimensional infrared imaging of a human body produces a time-varying topographic map of the skin surface on which is overlaid a complex time-varying thermal pattern derived primarily from thermal effects of the superficial vascular network. Processing according to the methods of the present invention yields a time-varying 3D/IR curvilinear feature map and its skeletonized version containing centerlines of feature segments. Branching and overlaid curvilinear segments of the skeletonized feature map define precise nodes which together with the skeletonized feature map represents a whole body registration mesh.

The mesh is projected onto the body of the patient to provide realtime visualization of the vascular network and other subsurface anatomical features, permit direct observation of the effect of respiration and cardiac induced motion, and provide references to assist in repeatedly picking precise measurement and treatment locations in spite of patient movement. Additional processing of the 3D/IR imagery separates veins, arteries, skin creases, other external features such as moles and scars, and other internal features such as cysts. Different colors are assigned to each type of feature, with the resultant projected image including the color information.

Quantitative values of temperature, elevation, motility, color and oxygen level of the skin, and level of hydration can be obtained from the 3D/IR imagery for each pixel location. A monitor displays the realtime 3D/IR image overlaid with selected feature types displayed in selected colors. Also shown on the monitor is a running timeline of quantitative value signals at a particular location selected by placing a cursor on the monitor display. Cursor position is also projected onto the patient's skin surface in a selected color which may be invisible. The time sequence of imagery, projected feature maps, cursor position and quantitative data is recorded.

Realtime 3D/IR visualization and recording can be performed during chemo or radiation therapy, during other imaging such as X-ray, as part of sleep research, for training purposes, and other uses such as monitoring wound healing via telemedicine. Positioning of surgical instruments, radiation sources, and other sensors can be guided by reference to the standardized locations.

3D/IR bodymaps can be processed in realtime and projected onto a patient without risk during surgical, diagnostic, and treatment procedures to assist medical personnel in visualizing internal organs. Fast processing and display maintains fidelity of the projection in spite of cardiac, respiratory, and other movements by the patient. 3D/IR feature mapping does not utilize vessel widths. However, feature maps produced during the process leading to bodymaps include variable feature widths and that information could be retained for diagnostic use as well as for projection onto the patient.

3D/IR Medical Image Standardization

The skeletonized feature mesh is used for medical image processing including to: standardize 3D/IR imagery and other imagery taken concurrently; lock onto a precise anatomical reference location to cancel the effect of involuntary or voluntary motions; register and combine 3D/IR imagery with imagery from other sensor modalities; compare images taken of the same person at different times; and compare images of different persons. The 3D-IR model is rotated to transform it into one or more standard orientations. Different images taken at different times, from different distances, with different cameras, of a subject whose positions vary relative to the cameras—can all be processed to transform them into the same standard poses. This greatly simplifies image comparisons and automation of image assessment, and provides an enabling technology to establish searchable databases of medical images from all imaging sensor modalities.

Various techniques can be used to generate 3D/IR images without loss of generality for embodiments of the present invention. Techniques include: Triangulation schemes such as those using structured light; Interferometric schemes using Phase-shifting; Time-of-flight schemes; Depth from defocus, Moiré, and Sequentially coded light; and Stereo vision using two or more cameras.

Calibration processes relate a range measurement to each IR image pixel. The resulting "point cloud" of data forms the 3D model which can be rotated in three-dimensional space along axes defined by anatomical landmarks. Rotation into standard poses is accomplished by orientation of specific anatomical landmarks, orientation of calculated virtual features such as planes of symmetry, or optimized correlation against pose-standardized reference images. IR and range sensors generally have different imaging rates; time synchronization is required during calibration and subsequent imaging due to thermal and topographic variations that occur across the entire skin surface throughout respiration and cardiac cycles.

3D/IR Physiological Condition and Psychological State Assessment

Specific nodes and feature segments are linked to specific anatomical structures and related regions, such as the temporal artery, external carotid artery, or branches of the trigeminal nerve. Thermal and elevation changes at those locations frame-to-frame provide quantitative data on systemic physiological condition such as vital signs, and provide standardized reference positions for localized conditions such as swelling and infection.

Systemic and local physiological changes in response to controlled stimuli also provides indicators to assess psychological state. Transitory reactions, to subliminal or overt stimuli, such as sweating, blushing, microexpressions, tics, muscle tightening, and asymmetrical thermal distribution become more detectable when movements due to respiration and cardiac cycles are removed through lock onto pixel-level landmarks in the registration mesh.

3D/IR Combined with Other Image Modalities

The non-invasive, risk-free nature of 3D/IR imagery allows 3D/IR feature maps to offer a universal approach to medical image standardization, comparison, and exploitation for identification and assessment.

Additional imaging sensors such as color visual cameras can be similarly calibrated to achieve pixel-to-pixel registration and form a composite (R,G,B,X,Y,Z,T) image. The composite is configured as a multi-layered 3D true size surface model in which features from multiple layers can be blended for visualization. The various imagers will generally have different array sizes and formats, different fields of view and depth of focus which must be considered during calibration. Using skeletonized IR features provides the most precise feature localization and standardization; however it requires simultaneous imaging by all sensors used and exact recreation of the sensors, optics, relative positions, and focus settings used during calibration. Any significant change to any of those parameters requires a new calibration. The visual layer is not used to construct the feature map. It is not necessary to incorporate a visual camera for the primary embodiments of the present invention, but it adds utility in certain applications. Use of the term "3D/IR model" should in all cases be interpreted to include models that may have additional layers from visual imagers and other sensors.

For efficiency, IR imagery is used to scan an area and locate warm blobs. Range measurements of each blob are taken and used to determine their size and apparent temperature, allowing for distance attenuation. Range data is also used to separate subject-related areas such as hair and clothing from same temperature backgrounds. Blobs that may be persons are then determined by their size, shape, and thermal characteristics. IR features are extracted and used to find faces, determine the area of face seen, and track movement of the face while aggregating the 3D model. Range images are processed to extract topographic features which are used to establish standard poses for the face. Symmetry in both IR and Range images is evaluated. Encoding of the face incorporates both IR and Range data. Visual imagery is collected when lighting conditions permit. IR data is used to determine which areas, if any, of the visual image are disguised; external landmark areas that appear to have been cosmetically or surgically altered; presence of contact lenses and appearance of eyes behind eyeglasses.

Encoding of 3D/IR Standardized Images, Features, and Characteristics

Encodings of standardized images, curvilinear anatomical features and their characteristics are used for identification templates, processed image headers, and classification sorting Codes includes the location, shape, size, orientation, and other characteristics of each feature, plus the location of specific anatomical landmarks within a standardized template derived from that image, plus statistical and other summary information regarding the template for use in assessing the quality of the template and its utility for specific tasks. The encoding can be embedded as header information within the image, or can itself be used for classification and identification applications with linkage back to the original image when required. Portions of the header can be visibly printed onto hardcopy imagery and reports to assure they are related to the correct patient.

Encoded feature and header information directs organization of medical image libraries. It is used to characterize the subject in the image, characterize the quality and parameters of the original image, predict the quality and parameters of certain processing to indicate whether it is sufficient to get the desired result with high enough confidence, determine the aspect angle from which the image was taken, partition the reference databases to select candidate matching images with similar enough imaging conditions, aspect angles, subject characteristics, and sensors used to provide accurate comparison.

Biometric Identification from 3D/IR Standardized Images, Features, and Characteristics The complexity and density of anatomical structures generating the feature map assures that each person's feature map is unique. Analogously to fingerprint identification, a person can be identified from a partial feature map if it contains sufficient common feature segments and nodes corresponding to a reference image. An encoding of node and segment locations and other characteristics from 3D/IR imagery of a portion of the body, such as the face, can provide an identifying code without the need to match a reference image.

Standardized images and their extracted feature maps can also be used to identify persons including those for whom only visual images are known to exist in a database. Processing of range and visual images can be used to designate those line segment features which correspond to external anatomical curvilinear features in the thermal infrared image, such as nose, eyes, mouth, and ears, moles, facial hair, burns, cuts, and scars. Although thermal infrared images provide extensive additional curvilinear features over visual and range images, comparisons can be performed between infrared and visual images by using external features derived from the infrared image to match against the visual features. While the utility of such cross-spectral matching for identification is highly dependent upon the quality of both images, in particular with regard to the illumination of the visual image, the technique is quite useful for partitioning databases in each spectral band such that they are conveniently related to each other in terms of overlap between partitions. If disguises, worn or surgical, may be present, care must be taken in considering the true position and characteristics of the visual features.

Automated biometric identification based on comparison of standardized images and feature maps have important applications both within and beyond medical requirements for: patient and staff identification, integrated surveillance/access control systems, single sign-on computer network access controls, and medical insurance ID cards.

Overlay and comparison of visual and IR layers detects visual disguises as taught in Prokoski U.S. Pat. Nos. 6,751,340 and 6,920,236. Overlay and comparison of range and IR layers distinguishes internal from external IR features; skin folds and wrinkles create both thermal and topographic depression features whereas blood vessels cause thermal features and may cause surface elevation but do not cause surface depression. Changes in skin surface texture due to level of hydration cause emissivity differences that affect local apparent skin temperature; variations in range measurements can associate apparent temperature variations with texture effects.

Role of 3D/IR

Three primary roles for 3D/IR feature mapping in imaging of human bodies are:

Enabling technology for searchable databases of medical images: Extensive manual interaction is currently required in exploiting the combined diagnostic value of different medical imagers due to variations in scanning orientations, resolution, fields of view, patient position, use of reference templates, and imaging protocols. Creating digital medical image libraries for automated cross-modal image fusion and image comparison requires the development of common standard formats. 3D/IR feature mapping is designed to provide a universal standard surface model for all imaging sensor modalities.

New medical imaging modality to replace or augment current diagnostic imaging modalities: Other medical scanning techniques such as x-ray, MRI, and CT are relatively slow, may require injection of contrast agents or use of harmful radiation. 3D/IR does not. In addition, 3D/IR is much less expensive to purchase, maintain, and operate; is portable for rapid deployment to thermal triage at accident locations; and automatically provides identifying features in every image. 3D/IR can replace other imaging sensors for certain applications.

Risk-free high performance visualization to replace manual observation: 3D/IR provides enhanced realtime whole body surface modeling with detailed overlaid mapping of internal vascular structures that can be projected onto the patient or viewed on a display. Advantages over manual observation include visualization of specific anatomical landmarks, constant quality regardless of lighting, and highlighting of minute thermal and topographic anomalies that may be early indicators of serious conditions such as adverse reaction to vaccination or incipient pressure ulcers.

3D/IR provides both a whole body surface 3D model and a detailed mapping of internal vascular structures that can be used for precise correlation of range or infrared image feature to anatomical location and for registration of multiple images. Images taken at various times can be automatically compared. The high thermal sensitivity of the system provides earlier indication of incipient infectious conditions than current technology. Routine automated scans of all nursing home residents at least once a day can detect incipient pressure ulcers (bed sores) pre-Stage One, reducing the multi-billion dollar annual treatment costs and reducing the racial disparity created by current reliance on visual observation of slight color changes for detection at Stage One. 3D/IR provides rapid, risk-free detection of thermal, volumetric, and textural characteristics correlated with infection and contagious diseases. The assessment process does not require a health care professional be in contact with the subject and does not generate any contaminated medical waste.

Earlier patents by Prokoski including U.S. Pat. Nos. 6,173,068, 6,496,594, and 6,529,617 used minutiae derived from 2D/IR for identification, registration, image fusion, stabilizing instruments relative to patients; and used IR/Visual dual band imaging to improve identification accuracy. Each embodiment of those prior methods required scaling and calculated projections of features from images taken with different poses, distances, and camera angles. While producing satisfactory uniqueness and repeatability for small surface areas of persons in small databases, the prior techniques are not sufficiently precise for whole body mapping and standardization.

3D/IR feature mapping removes the requirement for scaling to eliminate distance variations by providing ground truth metrics. It eliminates the mis-classification of skin folds as vascular elements. It eliminates distortion in 2D/IR features caused by projection geometry and thereby improves the consistency of feature shape and location. It enables standardization of pose, detailed segmentation and reconstruction of a whole body surface model, and volumetric measurements of body segments. The modeling precision provided by 3D/IR feature mapping enables precise localization, early detection, and monitoring of thermal, textural, volumetric, and color changes on the skin surface of a person based on images taken at different times.

Resulting 3D/IR/Visual models and extracted feature maps for each person are unique and persistent in spite of orientation, body temperature and ambient temperature changes. They have been shown to be unique for identical twins and persistent across different infrared cameras in the 3-14□ spectral band.

Segmentation and edge detection issues in analysis of IR or Range imagery include confusion in IR between thick hair vs clothing or background, and between thin/whispy hair vs skin. Range data can confuse skin surface and clothing, disguises, and articles between the subject and the sensor. Visual data confuses clothing, hair, other objects or persons contiguous to the subject. Combination of all three sensor modalities generally solves segmentation issues.

Visual face recognition techniques require controlled lighting, are vulnerable to normal daily changes in appearance as well as to intentional disguise, and do not have sufficient feature complexity or density for scalability to a billion people. Other biometrics such as iris scanning or fingerprints require close or contact distances and cannot be performed in realtime with non-cooperating subjects. 3D/IR-ID offers faster throughput, greater security against identity theft, greater potential for covert use, and ability to match against legacy databases including mug shots, driver licenses, and passport photos.

People leave trails of biometric debris while moving through life: fingerprints on objects touched; DNA in the forms of slough cells, shed hairs, saliva on eating utensils; handwriting samples; facial images, iris patterns, and voice samples collected by surveillance systems. Identity thieves will take increasing advantage of that debris as biometric identification achieves broader use in everyday life. Easier methods will likely be developed for creating forged fingerprints and iris patterns, increasing the challenges for unattended biometric identification.

Uniqueness of a biometric is determined by the complexity of the underlying physiology, and degree of randomness in its development. Distribution of biometric characteristics across general populations, identical twins, and siblings can be used to develop classification schemes and determine the theoretical accuracy of identification based on selected biometric characteristics.

Scalability of a biometric is determined by the complexity and randomness of the physiological mechanisms that produce the templates used for identification; it can be reduced but not increased by the design of the sensor and system. The ability of a biometric to uniquely represent individuals in any size population depends on the possible permutations of the physiological mechanism that creates the biometric's patterns. Merely stating that the underlying mechanism is "random" does not necessarily mean that it creates unique patterns in sufficient numbers to identify billions of people. Encoding biometric patterns into a large number of bits through wavelet decomposition, as is done for iris patterns, produces a very large number of theoretically possible codes. However, there is no basis for assuming that every code is equally likely to occur, or that the set of possible codes truly represents the set of possible outputs from the physiological mechanism that generates iris patterns.

Thermal facial identification is preferable over identification from visual images since the former is more secure. It is impossible to counterfeit or forge one face to look like another in infrared, whereas it is often possible to disguise one person to look like another in visible light. In the extreme example, most visual ID systems cannot distinguish between identical twins; an IR comparison system can. IR imaging offers the advantage of providing a surface-level, non-invasive, passive view of the interior structure of veins and arteries in the face. Although the IR signature can be blocked, it cannot be changed by surface or surgical variations, without those processes being detectable. 3D/IR virtually eliminates the two primary sources of errors in current face recognition systems; namely lighting and pose variations. 2D/IR eliminated lighting variations but still suffered from pose and scale variations and from errors in hair/skin/background segmentation.

BRIEF DESCRIPTION OF THE DRAWINGS

The foregoing and other objects, aspects and advantages will be better understood from the following detailed description of a preferred embodiment of the invention with reference to the drawings, in which:

FIGS. 16a and 16b are displays of facial images in a range of poses showing dense feature content at any angle, with FIG. 16b being annotated by the dots developed as shown in FIG. 17d.

FIG. 25b shows the corresponding extracted skeletonized featuremaps for comparison.

DETAILED DESCRIPTION OF A PREFERRED EMBODIMENT OF THE INVENTION

Conditions Required for Accurate IR-ID

Figure 1:
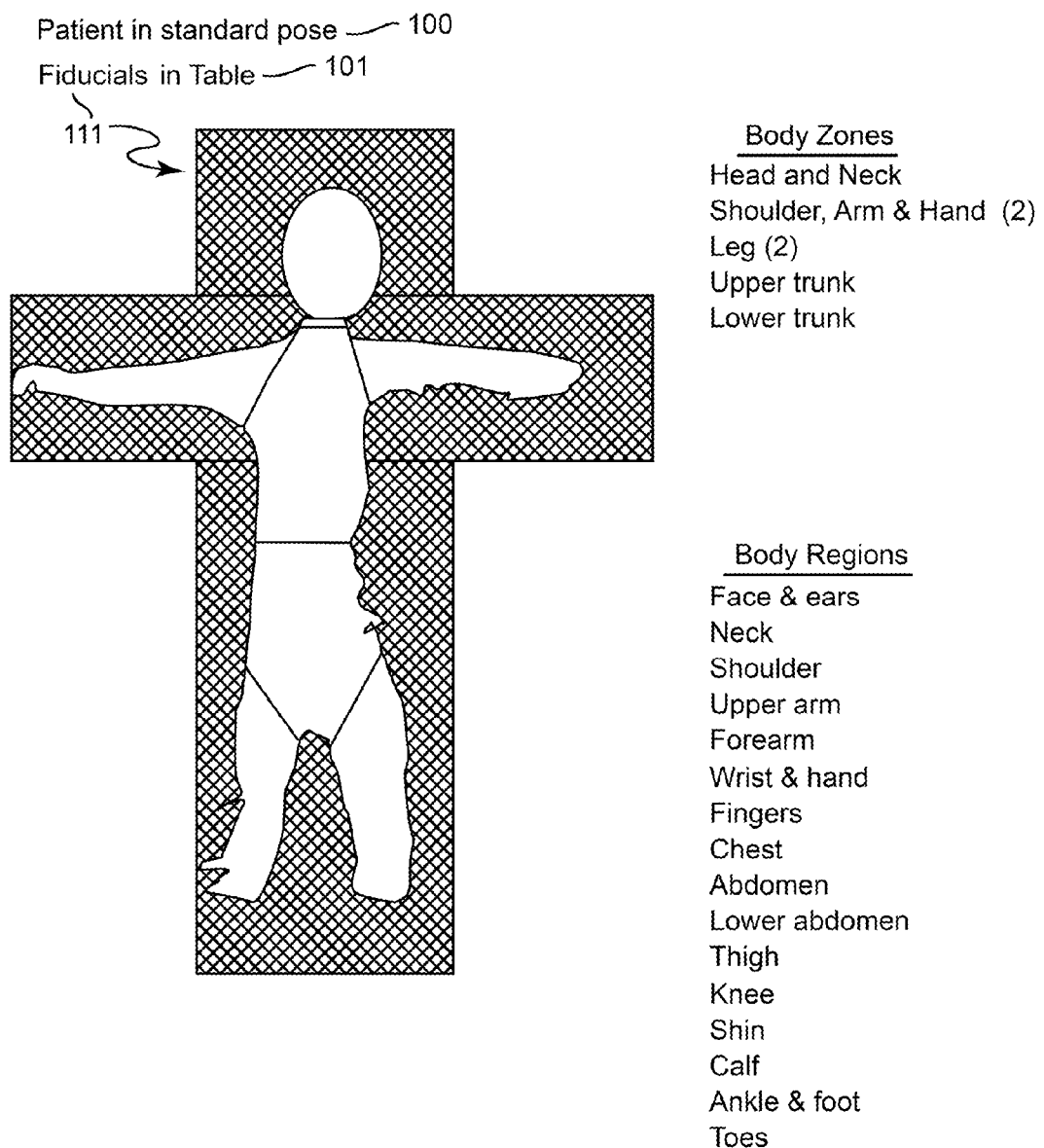
FIG. 1 is a schematic diagram of a front view of a patient showing body zones and regions.

Matches between different prints taken from the same finger are never perfect, since the fingers are deformable three-dimensional jointed structures which leave two-dimensional prints on surfaces they encounter through pressure. The exact angles between the fingers and the surfaces, the amount and direction of pressure, and the effect of movement between the fingers and the surfaces all cause variations in the exact prints produced. Even when prints are produced by a live scan technique, variations in the lighting, hand position, pressure applied, oil or dust on the fingers, use of lotions, and scratches or paper cuts will produce variations in the prints produced.

Therefore, the exact number, position, and characteristics of minutiae extracted from two prints may be different even though they are produced by the same finger. The challenge for an automated fingerprint matching system (commonly called AFIS for Automated Fingerprint Identification System) is to recognize allowable minor variations in actual matching prints while not allowing variations so wide that mismatches occur. Several AFIS systems are now commercially offered which provide acceptable accuracy.

The ridgelines of fingertips can be seen with the eye, as can fingerprint patterns produced by contact between fingertips and an object. Minutiae locations are apparent on both the fingertips and fingerprints, although various algorithms may be used to select a specific pixel or subpixel within the obvious branch, island, or end point area. Analogous techniques and systems are applied to the extraction and matching of minutiae points from infrared images of human faces for identification of individuals in earlier patents. Persons previously identified and logged-into a facial recognition system are later automatically identified from live or recorded images, by comparing the facial minutiae of the unknown image with that of all known images in the database. To reduce search requirements, the database may be partitioned by first classifying the faces either based on minutiae-related characteristics or on other characteristics such as feature metrics.

Since it is of interest to identify faces seen in crowds, or faces turned at any angle, a sufficient number of features must be extractable so that a partial face can be used for ID. This is again analogous to the situation with fingerprints, where a partial latent print may be matched against a rolled print or another partial if enough common minutiae are found. The particular technique used to extract thermal minutiae from facial images, and the number extracted, depend on the sensitivity of the IR camera used; just as the number of fingerprint minutiae found depends on the resolution of the fingerprint image scanner.

Just as raw fingerprint images may contain time-varying features caused by scars, paper cuts and debris, raw thermal images may contain features cased by wrinkles, sagging skin, and razor cuts. In both modalities, these anomalous features may be filtered out with suitable processing, may be useful features in matching, or may be ignored as spurious noise which does not interfere with identification. Facial deformations associated with facial expressions can be modeled as with pressure-related deformations in fingerprints.

The temperature of the face changes with metabolic effects, including ingestion of food, alcohol, and drugs, and with physical exertion and ambient temperature changes, among many other causes. The underlying pattern of blood vessels does not change, but for a given infrared camera, additional details of the vascular pattern may become apparent when they warm to above the detectable threshold. The identification procedure should rely primarily on large vessels which are more consistently apparent under all conditions. Matching and encoding engines must allow for some degree of variation in total density of apparent features, and individual feature location to accommodate distortions caused by the subject's movements and temperature changes, and by the limits of the sensor, scanning and analysis subsystems.

Thermal Infrared identification based on thermal minutiae points considers the smallest possible spatial features and has been shown to have fewer errors induced by head position changes, faster processing, and scalability up to larger databases. Processing algorithms and systems developed for fingerprint minutiae-based identification can be adapted for use with thermal minutiae identification. However, the need for precise and repeatable location of thermal minutiae points requires the use of expensive high performance thermal infrared cameras. Also, in order to provide for partial face matching based on images taken at different aspect angles and showing different areas of the face, it may be necessary to determine and store characteristics of each minutiae in addition to its location relative to face axes. Characteristics can include: type of minutiae [branch, apparent end, island, vein, artery, etc.], vector angles of the vasculature leading to and away from the point, and connectedness between minutiae. Encoding that data into compact form, and matching an unknown encoding against a very large database of encodings has been shown to be highly computationally intensive in the case of matching latent fingerprints. The greater degrees of freedom involved in head movements would be expected to make the identification of non-cooperating persons from thermal minutiae even more complex and time consuming than the identification of partial latent fingerprints.

Prokoski's prior art used the pattern of curvilinear line segments derived from the vascular pathways and from other anatomical features as the identifying characteristics. These spatially derived features are smaller than thermal contours but larger than minutiae. However, they may be derived from lower performance IR cameras than the ones required for minutiae extraction, and offer more compact templates than can be obtained from either thermal contour or minutiae encoding. That provides for increased scalability and speed of identification against very large databases, and requires less computationally intensive processing than is required for contour or minutiae comparisons. Prior art did not utilize topographic data or range image measurements and so could not achieve the standardization precision required for unique face coding with scalability to billions of people. 3D/IR of the present invention can achieve that level of scalability.

Sets of features having characteristics unique to each person and sufficiently persistent can be used as a biometric identifier. Sets of features having characteristics common to all persons and sufficiently persistent can be used to standardize images for alignment and comparison. Features in the thermal image result from internal thermal variations and external thermal and emissivity variations. Facial hair, scars, surface cuts, and other impinging external elements could be confused with internal anatomical elements; especially in skeletonized format. The present invention expands upon the prior art use of curvilinear features by using three dimensional surface imagery. The 3D surface model is generated by combining a range imaging sensor with an infrared imager. Features in the range image are all caused by external elevation changes. Comparing the feature sets from the two sensors separates the thermal features into internal and external origins. In particular, wrinkles and skin folds, which produce thermal patterns than may resemble blood vessels, also create range features and so may be discarded from use for identification because they can be produced by disguise.

Cooperative Subjects:

In applications with cooperative subjects, the primary sources of error in current face recognition systems are variations in lighting, head pose, and appearance. 3D/IR minimizes or eliminates all three error sources by using subsurface anatomical features that are unaffected by those variations.

Noncooperative Subjects:

When the application involves noncooperative subjects, automatically detecting the presence of a subject, then finding the subject's face and facial landmarks is difficult and slow for current face recognition systems—especially in a cluttered environment. 3D/IR more readily locates faces and anatomical landmarks quickly and automatically regardless of environment.

Adversarial Subjects:

Persons who don't want to be recognized can fool current face recognition systems without creating suspicion through use of quick tricks with cheap materials, or through extensive facial surgery that may involve re-sculpting bones and adding plastic implants to make one person look more like another person, or just look less like himself. 3D/IR is far less likely to have false negative errors due to worn or cosmetic disguises and has essentially 0% chance of false positive errors due to surgical disguise.

Covert Surveillance:

Most Watch Lists contain only visual images, taken from various camera angles and distances, in which the subjects may be disguised. 3D/IR can utilize those databases to ID people captured in covert 3D/IR images taken in total darkness. The technique uses anatomical modeling to eliminate Watch List entries that are impossible matches and then assigns correlation values to any remaining.

Tagging Unknown Persons:

3D/IR produces a unique FaceCode for each person, with specific portions of the code corresponding to specific sections of the 3D face. The technique can be used to tag and track multiple unknown persons moving through a complex scene. Additional portions of a FaceCode are aggregated from sequences of frames as the unknown person moves past one or more cameras that view additional areas of his face. The ability to determine that the same unknown person is visiting certain sites, or that he appears on-site immediately following an incident, or that he meets with persons on a Watch List may provide important intelligence and linkage data for predicting criminal and terrorist activity, or correctly assigning responsibility after it occurs. FaceCode provides a method to initiate a file on an unknown person and combine multiple files initiated on the same person—without needing to establish the person's true identity.

Feature Extraction and Template Matching in 3D vs. 2D Infrared

Infrared identification uses passive infrared cameras plus processing techniques to extract subsurface patterns associated with vascular and lymphatic structures unique to each person. Analysis of those patterns is analogous to fingerprint ridge and minutiae processing. On the order of 400 minutiae are produced across the entire facial surface. Positive identification even against very large databases requires matching less than 20% of the total minutiae. The process of ID based on a partial face image is analogous to the process of identification based on a partial latent fingerprint.

Methods for minutiae extraction and matching from 2D-IR images is applicable to 3D-IR images. Minutiae associated with vascular branch locations has greater repeatability than overlay minutiae and apparent end point minutiae when camera, spectral band, facial expression, or ambient temperatures changes occur. When skeletonized features are subjected to sufficient Gaussian blur, branch minutiae locations overlay consistently. However, imagery from more sensitive IR cameras can change the apparent end point minutiae locations enough that they do not overlay corresponding minutiae from less sensitive cameras. Therefore, only branch minutiae should be used for identification and alignment when various IR and range imagers are used.

Branch minutiae extraction was automatically performed under prior art. The same extraction techniques support 3D/IR by providing a powerful aid in automated improvement of manually-selected landmarks for three-point standardization, or for locking-on to a point for monitoring of thermal and elevation data over time. Automated improvement substitutes the closest vascular branch point to the manually-designated point. It thereby provides a highly repeatable, fast, and precise landmark demarcation at the pixel or subpixel level. Whereas manually-selected points from a radiograph or raw IR image average 5-10 pixels deviation, automated improved designations from skeletonized IR images average less than 1 pixel deviation. Prokoski U.S. Pat. No. 7,027,621 monitors the condition of subjects by tracking thermal changes over time. Minutiae tracking through sequences of images aids in physiological and psychological assessment by removing motion artifacts including those caused by respiration and cardiac cycles. Use of 3D/IR provides more precise tracking.

Studies of fingerprint databases have calculated that the arrangement of fingerprint minutiae offers sufficient degrees of freedom to allow for those patterns to be unique for each person ever born. Facial vascular patterns lend themselves to a similar analysis of scalability. Considering the major superficial blood vessels in a frontal image of the face viewed with a thermal infrared camera, there are approximately 400 major vessel branches, points of overlay, and apparent end points in the superficial vascular structure of the total face vs. less than 100 minutiae in most fingers. Prokoski defines as thermal minutiae branch, overlay, and apparent end points, and compares minutiae from two images by comparing the relative locations of corresponding minutia, each minutia's type, and the vector orientation of the vessel segments attached to each minutiae. Two facial infrared images that produce essentially identical sets of minutiae in terms of these characteristics are said to be from the same person. The actual number of minutiae seen in an IR image depends on the camera sensitivity and resolution. Matching a sufficient subset of minutiae virtually assures positive identification, as with matching a number of fingerprint minutiae (typically 16 or fewer) from a latent fingerprint to a rolled file print. This allow for positive identification from infrared images of a partial face The number of minutiae and area of distribution is much greater for facial thermal minutiae than for a fingerprint. There is a much larger variance in separation between facial vessels than in fingerprint ridge spacing. Furthermore, fingerprint ridges are constrained by the boundaries of the fingers to be essentially concentric, whereas no such restriction applies to interior facial vessels. The degrees of freedom relating to facial thermal minutiae are therefore significantly greater than the degrees of freedom for fingerprint minutiae.

Various curvilinear and minutiae extraction algorithms are used by fingerprint identification systems, some of which merely utilize the location of the ridge lines and minutiae and others that also utilize additional information about the line vectors and type of minutia each point represents. IR-ID based on curvilinear and minutiae features can similarly consider only the location of the features, or can also consider the type and vectors of the branching blood vessels. Vessel diameter is not used as a matching characteristic because it may change for particular vessels in response to several variables including blood pressure and age. Unlike with fingerprints, every person's facial thermogram produces well-defined facial landmarks that remain essentially invariant in the absence of surgery or trauma-induced changes. Coarse axes can be specified based on symmetry and refined axes based on landmarks.

In 2D/IR-ID, a line connecting the outer eye corners can define the horizontal axis. The centerpoint between the corners can serve as the face center. The vertical axis can be drawn through the face center either perpendicular to the horizontal axis or so as to bisect the eyeline or a line connecting centerpoints of the nostrils. Using non-perpendicular axes complicates location geometry, but the resulting angle between axes is a strong classifier for partitioning the database to reduce search times. A mouthline can be defined to be parallel to the eyeline and go through the midpoint of the mouth in a normal resting position. The distance between the eyeline and mouthline can be used to scale all images to a standard size prior to matching. This distance is chosen because it applies also to profile views. In addition, it creates more distinction among thermal faces than would result from the use of eye spacing. Rather than using visually-defined external landmarks, use of major vascular branch points in the neighborhood of the external landmarks provides more precise and repeatable references.

3D/IR-ID adds calibrated, registered elevation data to provide true metrics. That removes the need for scaling which is a major source of error in identification against very large databases. It also provides the ability to transform 3D/IR images into a standard pose for precise quantitative characterization and comparison. 3D/IR-ID based on anatomical structures depends upon: (1) the complexity of the superficial vascular pattern of the body; (2) ability to extract curvilinear features from 3D thermal IR images; (3) ability to standardize resulting feature maps; (4) large differences between standardized features maps from any two people; and (5) relatively small differences between standardized feature maps from any two images of the same person.

Structural curvilinear line features in an IR facial image include: (a) External anatomical features that can also be seen in a topographic image or in a well-lighted visual image (edges of the head and ears, cranial and facial hairlines, eyes, nose, eyebrows, mouth, moles, scars). Their total aggregate length is on the order of 64" for a frontal image. (b) Internal anatomical features that are not seen in visual images (primarily vascular system elements). Total length of large superficial blood vessels is on the order of 110" aggregate length. (c) Edges of worn or applied articles (eyeglasses, jewelry, bandages) which would generally not be used by an automated IR-ID system but may be useful for ID or classification in certain cases.

Each area of the 3D/IR face contains anatomical references that can be used to correct, to some extent, for variations in rotation, tip, and tilt of the face as well as for expression changes. If precise IR and range images are collected, calibration is accurate, and standardization is precise, then the roughly 170" of line features from each of two different standardized 3D/IR images of the same person should overlay—with the exception of variations from facial expression or speech-related movement. The reachable set of locations for each minutiae point can be determined or predicted based upon its location on the face. Non-overlaying segments whose both ends are within the reachable sets of the corresponding minutiae in the comparison image are considered a tentative match. Images from different persons show little overlay even with allowance for reachable sets. Therefore percent of overlay of curvilinear features is an effective method of comparison. There is significant variation in vascular patterns of identical twins, and between the right and left sides of any person's face. Unique ID can be established based on a percent of the total line length of extractable IR features. The actual percentage required to ID a person against all other persons is primarily a function of the amount of anatomical structure seen in the IR image, and the consistency of the 3D/IR sensor data.

In advance of considering overlaying the line features, two standardized images can be compared with respect to metrics such as: total length of internal and external linear features, distribution of feature lengths across the face area, number of apparent linear features, and angular distribution of linear features of each type as a first step in discarding obvious non-matching comparisons. IR/Visual matching considers the percent of overlay of external IR features with corresponding Visual features. Overlay % translates into a quantitative measure of the confidence that two images were taken from the same person. Overlay % is a primary measure of reliability for the system.

Guaranteed improvements that IR-ID offers over current biometrics are: security against sophisticated forgery and inherent proof the subject is alive at the time of imaging, continuous verification of presence and identity during extended periods, no need for lighting, no need for physical contact with the subject, no interference with the subject's activities, simple and convenient use with little or no training required, universal application to all faces without racial or ethnic bias, Potential other improvements, depending on how IR-ID is incorporated into a system, could include increased accuracy, speed, scalability, use with non cooperative subjects, covert use, and determination of subject's physical condition and psychological state in addition to identity.

Issues in Standardization and Encoding

The normal body is grossly bilaterally symmetric visually and in both elevation and temperature. Although symmetry is never perfect in any modality for which the sensor provides 8 bit or greater range of variation quantized at the pore level, the assumption of symmetry provides a basis for assigning personal axes and defining standardized poses. Side to side thermal variations are typically less than 0.25 degrees Celsius in a healthy person. Where the skin surface is unbroken, there is a gradual variation of temperatures across blood vessels, with the highest temperatures across the body surface being directly on top of major blood vessels. There is monotonically increasing temperature at the skin surface along the path of vascular segments; increasing toward or away from the heart depending on whether the segment is artery or vein. Non-monotonic thermal variation generally indicates a skin fold or other surface feature, although it can indicate depth variation in a vascular element. Extracted curvilinear features, segments, and minutiae can be classified by sensor (IR, elevation, visual), source (vein, artery, skin fold, external facial feature, hair, worn article, or other surface anomaly), shape/location/size in three dimensional space, and conditions prevailing. A subset of such classified features is sufficient to uniquely identify a person.

Major thermal discontinuities occur at entrances to body cavities such as the eye sockets, nostrils, or mouth. Local and relatively minor discontinuities in the skin surface occur at scars, moles, burns, and areas of infection. These provide reference landmarks for automatic orientation of the 3D thermal image instead of, or in addition to, symmetry axes. The thermal surface can be distorted through pressures and activities such as eating, exercising, wearing tight hats and other clothing, sinus inflammation, infection, weight gain and loss, and the effects of gravity and body position. Such influences must be considered in classifying features and extracting metrics.

Both systemic illness and local injury can affect measurement of vital signs and produce or enhance thermal and topographic asymmetry. Controlled stimulation can produce transitory changes in vital signs and asymmetries characteristic to a person and/or a condition. For example, a person who suffered a stroke might display exaggerated asymmetrical facial expressions due to nerve damage or muscle weakness. Transitory facial expressions include micro-expressions which are considered to be cross-cultural involuntary emotional responses to a stimulus. Responses such as surprise and sadness may cause symmetrical changes while others such as contempt and disgust generally produce transitory gross asymmetry especially in the lower face. Encoding the changes caused by controlled stimuli provides a method for assessing physiological condition and psychological state.

External features such as hair, moles, scars, wrinkles, and skin folds produce disruptions in the range images as well as in the thermal image. Overlapping features occurring in both IR and range images, or IR and visual images, or in all three modalities are necessarily external.

Images can be rotated into frontal or other standard poses defined by symmetry or landmark references. Skeletonization of extracted curvilinear features produces a pattern of binary line segments, branch and apparent end point minutiae. By defining an origin and path, the pattern can be transformed into an order 1D, 2D, or 3D binary FaceCode for simple compaction and comparison.

Sensors having high enough sensitivity to produce unique features for each person may not produce consistent features because they respond to the many factors influencing the skin surface at any given time. Methods that use thermal image data for identification and condition assessment suffer from the broad temperature variations caused by internal and external influences, as well as from the imprecision inherent in landmark selection from temperature, color, and range data. The use of pixel and sub-pixel landmarks defined by anatomical structures derived from thermal imagery is the hallmark of Prokoski's methods for precise identification and assessment, as further advanced by the methods of the present invention.

Realtime ID against Very Large Databases Requires Classification plus Encoding. Identifying a person in real time against a very large database of 100 million or more people requires developing effective methods for partitioning the database and encoding characteristic features into compact templates. Reasonable approaches to classification reduce the search space to 1% or less of the total database. Template or code comparisons against the selected partition can then be divided among multiple processors to meet required throughput times. Current fingerprint and visual face ID systems perform classification followed by comparisons between an unknown person's template and those of similarly classified database entries. The closest match in the database, if it is considered close enough, is the identification. Human review of the top-sorted candidates is often used, which limits the scalability of those systems. In the case of iris scanning, wavelet decomposition is used to derive a 244-bit code from the iris pattern. The technique used in deployed Iriscan systems for matching iris codes is proprietary and therefore does not provide a comparison for scalability and speed.

Visual face images can be classified but encoding via a compact template is difficult due to the large amount of variability in the visual facial image. To differently encode two identical twins, the analysis must consider micro-features. Fingerprints are routinely classified but encoding is complicated by problems in repeatably defining centers in arched prints and specifying axes in latent prints. The encoding of 3D infrared features offers a compact representation and rapid generation of a unique ID such as is provided by iris scanning—without its wavelet analysis. Furthermore, an identifying IR code can be covertly obtained from long and uncontrolled distances, as the subject moves, from any area of the face or other body part.

The present invention optionally includes external metrics such as the distance between pupils, distance between eyeline and mouthline, and angle between eyeline and symmetry axis. Also internal metrics such as the length of specific vascular segments, and their angles relative to the face axes. The present invention expands into three-dimensional models and generalizes the technique to provide a system for standardizing and encoding whole-body imagery from any imaging sensor, to enable automated search of medical image databases and condition assessment, as well as identification. Curvilinear features are extracted from the range data, representing edges of the topographic map as well as external features such as eyebrows, eyelids, nose contours and lips. Both range-derived and IR-derived curvilinear features, as well as direct and derived minutiae from those features, are used to establish identification through matching or encoding.

Identification from Partial Faces at Unknown Distances

Current visual and infrared identification methods rely upon symmetrical features to establish face axes. Identification from profile images at unknown distances is done based on a 1D profile outline signature and can be easily defeated by facial expression or facial hair changes, or by use of cotton balls or other "plumper" material under the upper or lower lip. 2D Visual frontal face images must be processed into a canonical format representing images without tilt or tip, centered about eyeline midpoint, and scaled to a standard size. 3D Visual images can be automatically rotated into a standard pose based on range symmetry, but are vulnerable to changes in the symmetry plane caused by facial expression changes, hair style changes, portion of face imaged and different initial poses. In addition to symmetry analysis, visual image standardization can be based on visual or range landmarks. However, landmarks derived from current visual and range imaging methods are not precise and are easily fooled by cosmetic or worn disguises; resulting in poor accuracy of ID.

3D/IR imagery provides positive identification from partial faces due to the density of thermal features, consistent extraction of features at the pixel or subpixel level, and their link to anatomical landmarks whose existence is universal for all persons. Whereas 2D/IR curvilinear features in the present inventor's prior art utilized the eyeline-mouthline distance as a reference scale, 3D/IR curvilinear thermal and range features utilize true metrics and therefore contain greater information content and precision. A smaller area may be therefore sufficient for unique identification if enough curvilinear feature segments are contained. The present invention provides a more automated method for determining what portion of the face is contained in an image, and for aggregating portions seen in each frame of an image sequence in order to form a more complete and 3D model of the unknown face. The novel use of range-derived curvilinear features and minutiae is added to IR-derived features to support higher recognition accuracy.

Selectable Non-Facial Areas for Secure Identification

Infrared imaging can be used to locate curvilinear features and minutiae points over the entire body surface that correspond to specific anatomical locations such as intersection points and branch points of the underlying blood vessels. The thermal minutiae technique and apparatus produce a set of whole-body registration points on the face and body surface. The registration points can then be used to align and compare infrared images taken with different equipment at different times of different people and under different conditions to facilitate comparison of those images. More than 2500 thermal minutiae may be identified over the whole body surface with current commercial infrared imagers. Future use of more sensitive infrared cameras with higher spatial resolution will yield additional features from deeper or finer vascular structures that may be incorporated into the methods of the present invention.

Unique positive identification of a person does not require imaging the entire face or other large area. Passive infrared imaging of curvilinear segment features of the anatomy over small areas of the human body can provide sufficient information to uniquely identify the subject.

As biometric techniques become more widely used, there is growing concern about the potential for stealing a person's biometric identity. The danger there is that, for most types of biometrics, a person has only a limited number of biometric signatures. Currently, the most secure and most used forms of biometrics are: fingerprints, iris scans, and visual face recognition. Each of these biometric techniques is vulnerable to theft.

In the case of fingerprints, people leave a trail of fingerprints behind them everywhere they go. Simple techniques enable a determined adversary to produce a synthetic finger covering which produces a replica fingerprint. There is concern that brutal adversaries may sever the fingers of persons and use them instead of fabricating synthetic prints. A person has only ten fingerprints, so it is easily possible to capture every bit of a person's fingerprint identity. There is not sufficient information density in the visual fingerprint image to select a subdivision of one finger, for example, at different times in order to increase the variance, and therefore the security, of fingerprint identification. Therefore, a person cannot generate a new fingerprint identity if his is stolen.

In the case of iris scans, it is a simple matter to record a person's iris pattern without his knowledge. The pattern can then be printed on a contact lens to defeat systems using iris patterns for identification. The person may be unaware his biometric identity has been stolen. If he does become aware, he may be able to re-enroll by using a new patterned contact lens. All contact lens wearers will be inconvenienced, or unable to unroll in iris recognition systems, if forged iris patterns become common.

In the case of visual face recognition, stealing a person's biometric identity may be as easy as taking his photograph. Many face recognition systems cannot distinguish between a photograph and a live person. Systems which include tests for "liveness" can be fooled by using makeup and other disguises designed to allow normal facial movements. Although persons have only one face, they can alter their appearance surgically, or through applied disguises. Therefore, a person can generate a new facial identity for himself; however an identity thief can continuously steal the new identity each time one is created.

Other biometric techniques that use a specific area of the body for identification have the same vulnerability to biometric identity theft. Use of vein patterns on the wrist or back of the hand, hand geometry patterns, or ear shape analysis rely on low-density information that has not been proven unique to each person. Therefore, these methods are not considered highly secure. In addition, if an identity thief steals these biometric signatures, the person would require surgical intervention to create a new signature.

What is desired is a biometric technique that can be applied to many different parts of the body, to enable the use of a new biometric identity signature in response to any actual identity theft, or to help protect against one occurring. The system of the present invention provides for identification based on imaging an area of skin anywhere on the human body. Since the imaging sensor is nearly in contact with the body, use of a range sensor is not necessary; optics of the IR sensor are typically 1:1 and true metrics are obtained from the 2D imagery. Two different implementations of the "selectable biometric" are described, both of which share the capability of allowing the same biometric sensor system to be used on selectable areas of the body.

Case I, the Biometric System Selects the Identifying Area.

3D/IR/Visual imagery is collected of a broad area, such as a face, but only a sub-area is used for identification. The sub-area is selected by reference to landmarks that can be determined from one or more layers of the imagery. For example, a full facial profile image can be obtained. The selected sub-area can encompass a narrow swath extending from the mouth corner to the lower ear lobe, which is used to produce a thermal biometric signature. The curvilinear thermal features within that swath are determined along with their elevation contours. All or some of the features may be used for identification by matching against a database of previously extracted swath patterns. Anatomical structure information observable in the infrared swath images, such as blood vessels, moles, scars, lymph nodes, sweat glands, and wrinkles, can be used to precisely align enrollment and identification swaths. Standard pattern recognition techniques are then employed to match the derived pattern against a database of patterns, and assign a confidence measure to any proposed match. The actual swath area used by the biometric system can be unknown to the users of the system, and can be changed from time to time to increase the difficulty of identity theft.

Case II the Biometric Subject Selects Identifying Area

The subject can select any area of his body of appropriate size, and use it to produce his identifying biometric. No one else, and no component of the system, need be aware of what area of his body he selects. The total skin surface for an average size adult is on the order of 9 square meters. The portion that could be conveniently used for biometric identification using a handheld sensor in privacy includes the face, neck, hands, lower arms, legs and upper chest. There are different feature densities in the various areas. The required size of the sensor array is determined by the spatial resolution of the sensor detectors, their sensitivity, and the size population to be uniquely identified. For a small area of the skin, elevation can be assumed constant and the sensor can employ means to maintain a constant distance between sensor and skin. Therefore, a 2D/IR sensor array can be used for static imaging or a 1D array can be moved across the skin surface. The recognition system will determine the degree of correlation between the current feature map and previously enrolled (larger area) maps using FlashCorrelation or other pattern to subpattern matching technique. This implementation can be incorporated into the Personal Biometric Key of Prokoski U.S. Pat. No. 6,850,147.

The present invention includes the use of 3D and 2D curvilinear line segment feature maps derived from 3D/IR imaging for unique identification of an individual. Once the feature map has been generated, prior art associated with minutiae extraction, graph matching, pattern recognition, and encoding may be applied to compare the results against databases of images, templates, maps, or codes. The imaged area can be any portion of the body; in particular it can be a face image that is less than or other than a full frontal view.

Medical Thermal Imaging

Standards in Medical Diagnostic Use of Infrared Imaging:

Historically, medical research involving IR imaging used IR cameras sensitive in the long wavelength infrared spectrum (7.5-14 μm). Typical protocols required tight control of ambient temperature at 22° C., air convection directly over the test subjects averted and speed of air incidence should not exceed 0.2 m/s. The subject must be kept away from electrical equipment that generates heat. The oscillation of room temperature should not exceed 1° C. in a 20-minute period. If possible, the imaging should be carried out in a room with no windows; otherwise, the windows must be double-glazed and have external screens or shields to shut out sunlight. Fluorescent lamps (cold light) are preferred to tungsten lamps. A digital thermometer, with a display that can be read from at least three meters away, should be available in order to monitor the location of the subject.

Current research involving diagnostic procedures often specifies use of IR cameras with sensitivity on the order of 0.02° C. with FPA (focal plane array) cameras using QWIP (quantum well infrared photodetector) or HgCdTe (mercury-cadmium-telluride) type detectors and 14-bit radiometric digital video output with a minimum 60 frames per second. Imaging is usually performed under controlled conditions designed to avoid creating artifacts in the imagery.

Subjects should avoid taking hot baths or showers, using topical agents, creams, talcum powder, and doing vigorous exercises or physical therapy at least two hours before the exam. They should preferably have fasted for three hours and not have taken stimulants including caffeine and not used nasal decongestants. The area to be imaged should be exposed for at least 15 minutes so that the skin and room temperatures reach equilibrium.

Protocols to date have focused on avoiding anomalies in thermal imaging. No standards have been established to facilitate automated comparison between medical IR images of the same or different persons. No standards have been established for fusion of medical IR imagery with other modalities.

Realtime Condition Monitoring:

Thermal sensitivity and spatial resolution of the IR camera limits what structures can be extracted from the imagery. Even with the highest performance cameras currently available, some branches of the superficial vascular system are too deep to be discernable from IR imagery of the skin surface. The particular vascular segments that can be extracted from IR imagery varies with the subject and his condition. Influences such as alcohol, drugs, exercise, and psychological changes can make smaller vessels discernable for a period of time as the heat distribution of the body changes temporarily and then reverts. The time-varying changes can be used to detect, track, and assess condition changes.

Imagery from high performance IR cameras is influenced by ambient, metabolic, medication, psychological and physiological states. Determinations derived from thermal images must take those variables into account. Ingestion of alcohol, for example, produces significant changes in the thermal pattern of the face. Measurable changes begin while the subject is drinking and continue for one or more hours depending on the amount consumed. The thermal pattern then slowly reverts to the original baseline pattern, assuming no further alcohol is ingested, over the next few hours. Analysis based on the imagery could be faulty if the alcohol effect were not considered. Thermal changes resulting from alcohol, and from vasoactive medications follow predictable trends. In theory, analyzing frame to frame changes in a sequence of frames provides evidence that the subject has taken alcohol or some other vasoactive substance, and helps estimate the recentcy of use and time until the effect has diminished by a certain percentage. Prokoski U.S. Pat. No. 6,173,068 presented that approach to condition assessment and monitoring. However, detailed timeline analysis requires pinpoint comparisons of many corresponding points in each image.

Precise landmark selection and consistent alignment is generally not possible from 2D images due to respiration and other movements. The extension to 3D/IR imaging of the present invention allows for greater precision in monitoring changing thermal conditions and also permits monitoring of changes to skin topography, which at finer detail is called texture. Apparent skin temperature at a given point is actually a function of true temperature plus emissivity. Emissivity is a measure of the efficiency of thermal energy radiated in a particular direction, and is a function of several variables including skin texture, level of hydration, and intervening substances such as hair, sweat and skin lotions. Use of precise range data to identify skin roughness and the presence of hair, and use of visual measurement of skin color to determine oxygenation and hydration, can better establish skin emissivity and therefore precise true skin temperature at imaged locations.

Localized comparisons with either baseline images of the same subject, or a set of normalized reference images was presented in Prokoski U.S. Pat. No. 6,173,068. In the present inventor's prior art, images were gridded into cells to aid analysis. Because a healthy person has a bilaterally symmetrical thermogram, asymmetries were used as indicators of possible wellness issues. In addition to the imprecision caused by tracking minutiae locations on a moving (living) subject, the imprecision caused by comparing images in different poses reduced the sensitivity of condition assessment performed in 2D/IR. By performing 3D/IR imaging, images can be transformed into standard poses to facilitate more direct and precise comparison.

Thermal Infrared Imaging of Human Anatomy

Blood regulates body temperature and constitutes 8% of body weight. A body contains 4-6 liters of blood. Arterial blood moves away from the heart; venous blood towards. All blood moves and essentially all movement is within blood vessels. There are 90,000 km of blood vessels in the body, counting all capillaries, with a surface area as high as 6300 square meter. Two major pathways of circulation exist in the body: pulmonary and systemic. Pulmonary starts at the right ventricle and systemic begins at the left ventricle. Blood pressure as blood enters the capillaries from the arterioles is 30-35 mm Hg. Pressure of the surrounding tissue fluid is much lower; about 2 mm.

Three layers of tissues form the arteries; with the outer and middle quite thick. Smaller arteries are called arterioles and have only one muscle layer. Arteries can constrict or dilate, regulated by the medulla and autonomic nervous system. Veins carry blood from capillaries back to the heart; they have the same 3-layer structure as arteries, but include valves to prevent backflow of blood, particularly in the leg. Blood pressure in veins is very low. Smaller veins are called Venules.

An anastomosis is a connection or joining of vessels, artery-to-artery or vein-to-vein to provide alternate pathways for the flow of blood if one vessel becomes obstructed or is insufficient. Aside from the epidermis, cartilage and the lens and cornea of the eye, most tissues have extensive capillary networks; capillaries carry blood from arterioles to venules. Some organs have another type of capillary called sinusoids, which are larger and more permeable than other capillaries. This permits proteins and blood cells to enter or leave the blood.

Core body temperature is normally 96.5 to 99.5° F. (36 to 38° C.) with an average of 98.6. Within a 24-hour period, there is a 2 degree F. fluctuation, with the lowest temperature occurring during sleep. Skin temperature is lower than core temperature. The amount of heat loss through the skin is determined by blood flow through the skin and by sweat gland activity; skin normally is at 88° F.

Depending on the optics used, and the sensitivity, gain, and contrast settings of the IR camera, the resulting imagery can distinguish the surface effects of superficial large veins and arteries only, or may also see the influence of individual smaller veins and arteries. Current commercial infrared cameras cannot distinguish deeper or finer anatomical structures directly, but future cameras will have that capability within the span of the present invention.

In addition to being used for visualization by a physician to aid diagnosis, resulting feature maps uniquely ID the subject. Some of the anatomical issues involved in visualization, such as loss of information when a blood vessel is hidden behind other anatomical structure, bear on the technique for encoding the characterizing features for each person. Existing methods for vascular modeling can be used to "fill in" the missing information in the 3D/IR feature maps, or the location of the apparent "breaks" can be considered to be additional characterizing information.

The human body is grossly bilaterally symmetrical when imaged using thermal, visual, or topographic sensors, although the symmetry is not perfect for any person in any sensor mode. When the portion of the body being imaged includes corresponding areas from both sides, symmetry axes can be derived and used to standardize the orientation and position of the body in the image. Adding range imaging to visual and thermal image collection allows standardization to occur in three dimensional space.

Upon locating a gross regional symmetry axis, bilateral sub-region pairs act as self calibrating sources for determining local asymmetries that characterize and identify the subject. Portions of the body, such as the face, that encompass bilaterally symmetric sub-regions are generally processed in a similar fashion starting with locating the gross symmetry axis.

When the goal is to standardize an image for comparison to a standard reference, matching against a database of similar images, classification or identification, precise and repeatable determination of symmetry axes is essential to current methods. Problems include the fact that no person is perfectly symmetrical and many influences such as changes in facial expression or posture may increase local asymmetry. The use of various grade sensors with differing spatial and sensitivity specifications changes the precision and reliability of procedures for determining symmetry axes and standardized images. Different methods for standardization create incompatible database search engines and increased mis-identifications.

When the goal is face identification, the visual face is grossly symmetrical, as are the thermal infrared face and the range image face. Symmetry waveforms and local deviations from bilateral symmetry can be used to classify the visual, range, and thermal images of the face, but are not sufficient for identification due to the effects of facial expression, physical condition, aging, and speech-related changes that may alter bilateral symmetry.

Because the thermal infrared image is bilaterally symmetrical to within a fraction of a degree, it might be supposed that the vascular structure is likewise bilaterally symmetrical. However, that is not the case. Major differences exist between the structures of the two sides of the face in every case seen. This lends further credence to the embryo angiogenesis and tissue repair angiogenesis models, which allow for random positions of branchings and sub-branchings—as long as the blood pressure and flow throughout the resulting networks achieves the required balance. Balance must be achieved bilaterally, through the four chambers of the heart, and with each heart cycle. Given parameters as to the min and max blood vessel diameters, the maximum blood flow possible through a vessel, the total blood volume, the ratios of capillary length relative to vessel length, and arterial to venous vessel lengths required to achieve blood purification and maintain healthy blood pressure, a Monte Carlo approach to modeling possible branching patterns would likely result in a number of possible patterns many orders of magnitude greater than the total population of humans who will ever live.

Identification or assessment of a region of the body without symmetry requires alternative methods for assigning axes. 3D/IR with curvilinear feature extraction provides for pinpoint selection of anatomical landmarks in each area and subarea of the body. A selection of three landmarks defines the standard 3D pose and orientation for any portion of the body, and also provides the mechanism for aggregating separate images into a more complete body model in standardized pose.

Relationship of the Present Invention to Prior Art

Prior art used infrared imaging for identification and condition assessment through: 1. Thermal contour analysis. 2. Thermal minutiae. 3. IR-Visual matching using anatomical rules. 4. Patient position stabilization. 5. Personal Biometric Key. 6. 2D curvilinear features. This invention differs from prior art in the sensors used, anatomical features derived, feature map derivation methods, primary embodiment being medical image standardization, secondary embodiment being realtime projected and displayed medical 3D visualization tool, and tertiary embodiments being improvements to prior art for biometric identification and medical image registration. The current invention utilizes binary patterns of lines segments in three-dimensional space derived from 3D/IR images through processing that destroys temperature information in the image in order to enhance visualization of curvilinear features representing internal anatomical features.

The present invention offers improvements to several significant aspects of the prior art including:

1. The current method yields an encoding technique that significantly reduces storage requirements and computational load when used with large databases and/or high throughput systems.

2. Identification from thermal contours is prone to contour edge changes caused by head pose and temperature variations. Changes in temperature resulting from ambient, physiological, and emotional conditions, and movements caused by facial expressions cause contour changes.

3. ID from minutiae requires precise determination of apparent endpoints and branchpoints. The current method using curvilinear feature maps does not require either extensive computation to produce a standard template, nor precise estimation of several apparent internal locations.

4. The current method for positive identification based on a single frame of partial face imagery requires a smaller portion of the face and allows for greater variation from frontal pose.

5. The current method automatically standardizes in three dimensions the pose of the face or other body part being processed.

6. The current method translates the original pose of a face or body part to match that of persons on a Watch List for more accurate comparison, and provides sufficient information content to facilitate accurate matches against databases of visual images (2D or 3D).

7. Range imagery of certain body areas, such as the face, has greater inherent symmetry than IR imagery and offers improved symmetry axis definition for fast standardization.

8. Range data aids in defining the separation of chin from neck in frontal images, separation of hair/skin/background areas, and separation of individual faces from crowds.

The methodology of the present invention differs from the prior art by:

1. Using jointly calibrated infrared and range [alternately called elevation] data to obtain true metrics and rotate the 3D/IR image into a standard pose.

2. Using adaptive equalization followed by thresholding and skeletonization to find curvilinear line segment features in both infrared and elevation standardized images.

3. Using horizontal vs. vertical filters, and infrared features vs. range features to distinguish external and internal features.

4. Using curvilinear features together with minutiae rather than minutiae alone for identification and assessment, thereby providing many more candidate matching pixels for higher confidence matches.

5. Allowing compact templates without the processing required for minutiae extraction and characterization. Interconnections among branch and apparent end minutiae are maintained in the line segments map which can be compressed through simple techniques such as run length encoding. Minutiae characteristics can optionally be stored as separate layers and used when needed for assessment and change detection.

6. Locking-on to anatomical landmarks defined by thermal minutiae in order to track respiration and cardiac cycles from elevation changes. Comparing images at the same point in their cycles results in less movement artifacts and more accurate comparison.

7. Use of full feature map permits use of lower performance IR cameras than when precise minutiae positions are required for ID. Resulting method has greater scalability.

8. Combination of IR, range, and (optional) visual imaging sensors provides more intuitive, direct and immediate comparison between IR and elevation or visual images, due to commonality of some features and ability to match poses.

9. Incorporation of calibrated range data supports standardization of imagery whether or not area imaged has bilateral symmetry.

10. Establishes a systematic method for standardizing imagery of any area or subarea of the body to enable searchable databases of 3D/IR imagery for ID or assessment.

11. Provides a universal standardization technique for other medical image modalities as well.

12. Provides a mechanism for aggregation of separate images, including images taken at different resolution, to produce a more complete model and code.

13. Expansion to 3D curvilinear features and minutiae provides pose standardization with sufficient precision and computational efficiency to enable realtime encoding, standardization, assessment, and monitoring.

Scope of 3D/IR as an Enabling Technology

Automated Library Search for Diagnosis and Prognosis

The system of the present invention acquires, processes, records, and archives medical imagery in standardized formats to enable searches for similar image content as well as images from patients with similar medical histories or other specific characteristics of interest. Image searches utilize the standardized poses and regional divisions of the body established for the feature mapping technique. Image comparisons utilize the anatomical landmarks derived from the feature maps to automatically register same landmarks in different images. Different images over time of the same person can be automatically compared, with changes highlighted, quantified, and compared against medical literature and against medical histories included with the image library. Sequences of images from one person can be compared against sequences from other persons to locate the progressions of prior patients whose outcomes may provide prognosis for the current patient. Statistical analyses of quantitative imagery data such as wound area, perimeter, and volume, can be automatically derived according to patient profiles and used to compare the results of different treatments. Similarly, patients who have undergone a particular treatment can be clustered by outcome and imagery from the current patient compared with the image histories from each cluster to predict treatment results.

3D/IR Systems for Medical Use

3D/IR imaging with feature map extraction is the common core around which dedicated medical system are configured, as in the following embodiments:

System for Image Standardization and Documentation

Systems dedicated to standardizing medical images from 3D/IR and other calibrated modalities output thermal, texture, color, and topographic data in the form of multilayered 3D and 2D images in which the original image is standardized and overlaid with additional registered layers including IR feature maps, skeletonized IR feature maps, X-ray, MRI, ultrasound images, and designated landmarks for the body area imaged. Each image is standardized based on landmarks specified for that body segment. Aggregated images from multiple body areas can be assembled into larger images, and portions of an image can be partitioned into smaller images.

Image frame sequences provide vital sign information through encoded timestamping in the header of each digital image; minute cyclic changes in temperature, elevation, and position of minutiae indicate temperature, pulse, and respiration rate during the collection period. Additional header information includes the designated subject name or ID code, date, time, location, 3D/IR system version and serial number, reference to the body region, subregion, or segment imaged, and coordinates of the three landmark minutiae used to standardize the image.

System for Automated Change Detection

The system processor determines difference between two standardized images from the same sensor modality of the same subject, including differences between any layer of the images. They can be images collected at the same session or different sessions, and can be from the same point in cardiac and/or respiration cycle when the effects of those rhythms are to be minimized, or images selected to determine maximum variance during a cycle.

The combination of range and infrared image sequences offers the capability to image lymphatic system behavior including periodicity, speed, and strength of undulations. 3D change detection provides monitoring of lymphedema to determine effectiveness of compression garments and massage techniques designed to reduce swelling. It enables standardized quantitative techniques for measuring and mapping lymphedema at time intervals, before and after radiation treatments, and before and after compression or other methods of treatment.

Similarly, the system monitors thermal and topographic changes in areas prone to pressure ulcers. Resulting comparison imagery is well suited for telemedicine communications with service bureaus having specialty expertise in these prevalent conditions.

System for Annotating and Standardizing Other Imagery

3D/IR system used in conjunction with another medical imager such as X-ray requires calibration of 3D/IR and X-ray sensors using calibration targets especially designed to produce sharply defined fiducials in each image modality; IR, visual, range, and X-ray in the example. 3D/IR imaging is performed simultaneously with the other sensor. Calibrated feature map, skeleton map, and/or minutiae landmarks from 3D/IR imagery are superimposed on the x-ray as a separate layer or merged. The X-ray is standardized automatically upon standardization of the underlying 3D/IR image.

A composite digital 3D model is constructed combining the IR and radiographic data. The IR data can be filtered to extract features and categorize them such as: vein, artery, vessiole, skin fold, hair, sweat pore, capillary, nerve, lymph node, mole, scar, wound. Features can be further processed to produce skeletonized features representing the centerline of curvilinear feature elements, and the skeletons can be further processed to yield minutiae representing apparent intersections, branchings, and end points. User of the model can select which IR feature categories to display, in which colors, as annotation on the radiograph.

System for Searchable Library of Medical Images

3D/IR imaging system incorporates a Bodymap directory that assigns a code to body part designations at macro to micro levels reflecting the fields of view of available imaging systems. For each body part at each level of resolution, three anatomical landmarks are specified that define the transform into standardized position for that body part. The landmarks are pixel or sub-pixel locations that can be located automatically or manually in the skeletonized 3D/IR feature map for that body part at that level of resolution.

Other image modalities are included in the library but the common factor is that all images have overlaid IR image layers and all are standardized using anatomical landmarks derived from the IR image. Each image stored in the library is transformed into its standardized position with an overlaid image layer designating the standardization landmarks, the standardization transform parameters applied, and possibly additional reference points.

The Bodymap directory also designates aggregation reference points used to combine images of body parts imaged at high magnification (micro levels). These points are likely to be seen in two neighboring images that are to be aggregated. The standardization transforms for the two images are used to construct an aggregated composite image representing what the original image would have been if the sensor had the combined field of view of the two images. The constructed composite image is then standardized using designated anatomical landmarks for the composite, which are three of the six anatomical landmarks used to standardize the two component images. It is given an annotation layer including the composite transform and landmarks used. Choice of which three landmarks are to be used for each aggregation is specified in the Bodymap directory.

Image sequences are processed similarly to single frames; their annotation may specify the sequence length, and frame number, or rely upon the date/time designation on each frame to indicate the sequence.

Each library image includes annotation of the body part, resolution, imaging system description, date and time, and such description of the subject and his medical history as is permitted given privacy regulations for the particular library. Libraries generated specifically for a clinical trial or to track military or other particular groups of workers may include additional subject information under written agreement with the subject. Libraries that are accessible under subscription by medical personnel or the general public are stripped of certain information depending on privacy regulations and the subscription agreement.

System to Assist Diagnosis and Prognosis

Medical image libraries standardized using 3D/IR feature mapping technology are accessed by search engines through services offering diagnostic and prognostic assistance. User interface is an interactive display of checkboxes through which the user designates a body part, scale resolution, imaging modality [which may include the make and model of the imager as well as the settings for that equipment], current medical issue or reason for current imaging, and query.

Additional choices can limit the search by age of subject, gender, general health status including specified chronic conditions, ethnicity, residence, specific current health issue, recent treatment regimen with dates, other medical and family histories.

System selects library imagery meeting the search criteria and compares each image to a current image entered by the user into the library by using the IR-derived anatomical landmarks to morph library images to the current image. If system determines that the degree of morphing is too great, user is directed to manually specify additional landmarks or to work at greater magnification. Visualization aids for the comparison include colorized and/or flashing areas that differ more than a selected percentage in a selected value (temperature, elevation, texture, motility, pulse, respiration, hydration) measured at a point or area specified by the user with a stylus on the display. Sequences can be similarly compared and visualized with the frame rate of the display representing true or other timing.

User-selectable functions extracts, compiles and analyzes comparison data from frames and sequences in the database partition selected. Results are presented in statistical form and used to generate an "average" subject image or image sequence for visualization.

Although the general progression of a medical condition may be indicated by imagery taken of various persons at different stages, the system is most effective when the library contains routine periodic imagery taken of the same subjects before, during and following diagnosis and treatment for a particular medical condition. The fast, harmless, and inexpensive nature of 3D/IR imaging supports such frequent imaging.

Data from pre-condition imagery of subjects who later developed a specific medical condition is then contrasted with data from imagery of control subjects who did not develop the condition. Differences are potential indicators for early detection of incipient medical conditions.

Data from pre-treatment imagery of subjects with a specific medical condition is compared with data from post-treatment imagery of the same subjects at various stages in treatment. Subjects are classified as to how successful their treatment was, and that classification is correlated with image data to yield statistical rankings for various treatment regimens and to associate a prognosis with each interim image.

A particular embodiment of the 3D/IR system for wound care management incorporates measurement of local skin hydration to produce a system for early detection of incipient pressure ulcers prior to Stage 1 which is defined as a local area of thermal or color change relative to the surrounding skin. Pressure ulcers most commonly occur over bony areas and where chronic pressure is applied to the skin. Elbows, buttocks, heels, calves, and shoulders are especially prone. Bedridden persons and those whose mobility is limited are at greatest risk. Pressure ulcers can advance from Stage 1 to Stage 4 in a few days if not detected and treated in time. Risk of death from septic infection is associated with Stage 4. Risk of spreading infection within a medical facility is also a serious concern.

Routine whole-body 3D/IR imaging is performed of each at-risk patient, on a daily or more frequent basis. Automated image analysis performs three functions and outputs a written report for the patients' files. First, areas showing local anomalous thermal, elevation, texture, color or hydration characteristics are highlighted. Second, areas showing bilateral asymmetry in those values are separately highlighted. Third, areas showing day-to-day or cumulative changes in the size and values for those characteristics are indicated. If any of the three types of anomalies is found, another 3D/IR image is taken of the area involved—this time after a period of time where no pressure is applied. If the anomaly disappears, the patient is repositioned and wet bedclothing changed but no further treatment is indicated. If the anomaly is reduced substantially but does not disappear, the patient is repositioned and changed and additional imagery is scheduled after a further period of time. If the anomaly is only somewhat or not at all reduced, further treatment is performed such as by applying negative pressure or utilizing an air mattress.

Pressure ulcers are an extremely painful but largely preventable condition with early detection. Dark skinned persons are less likely to be diagnosed at Stage One by the current method of visual observation by health care aides, resulting in racially skewed survival outcomes. 3D/IR imagery eliminates the racial disparity.

Progression of pressure ulcers, burns, and other wounds is monitored through automated analysis of standardized 3D/IR images to track changes in wound area and volume, thermal distribution and texture across the wound area and edges, development of apparent inflammation in areas surrounding the wound, changes in pulse, respiration, and blood flow in surrounding areas.

Systems for Imaging Large Populations

3D/IR imaging assists objective health assessment of unknown individuals and crowds. High-sensitivity infrared skin thermometry does not require physical contact with the subject, is noninvasive and requires no contrast medium, since the circulating warm blood itself produces sufficient contrast for high-resolution images. Analysis of IR imagery allows the identification of vascular disorders, neuronal and musculoskeletal problems, inflammatory processes, dermatological, endocrine and oncological conditions.

Portable 3D/IR imaging systems are used to capture and process epidemiological data on large populations. Crowd screening for infectious disease indicators, and quarantine management linking ID to status provide essential public health benefits. The non-contact nature of 3D/IR imaging and the capability for remote analysis reduces hazardous waste and potential for spreading infection to health care workers.

Large-population inoculation programs in rural areas often suffer from their inability to uniquely identify participants and keep track of treatment dates. The embedded identification capability of 3D/IR images is used to automatically match same-person imagery collected at public gathering locations, such as water supply areas, and compile on-going test results.

Effects on local populations caused by atmospheric events such as aerial spraying of pesticides, volcanic eruptions, or radiation releases can be statistically determined through analysis of 3D/IR imaging taken before and after the event without attribution. Personal identities need not be determined in order to assess the effects. However, the ability to automatically link images of the same person at different times enhances the utility of the system for tracking effects over time.

Within wellness clinics, individuals obtain automated reports on their general health, changes from their last report, and comparison against other people whose records are accessible to the clinic. Historical imagery from relatives, or from all persons with the same gender, age, ethnicity, and other demographic characteristics are compared to the individual. Quantitative measures of wellness are provided to the individual, and linked automatically with suggestions for improved wellness that are tailored to the medical history of the individual.

Infrared cameras are used to screen crowds at airports and other public sites to detect persons who have a fever and may be carrying SARS. Those cameras do not provide automated detection; they merely highlight on a display monitor all temperatures hotter than a set threshold within the field of view. Human observers look at the monitor to select which individuals they will approach for closer observation. 3D/IR provides automated assessment of the subject's condition based on quantitative measurements of skin temperature, texture, and topography from individual frames, measurement of vital signs (pulse, respiration, temperature, and heart signature) from frame sequences, and detection of other observables correlated with medical condition such as watery eyes, fixed gaze, tremours, cough, and dehydration.

Condition assessment (CA) performed with attribution, meaning that the subject's identity is determined and linked to his condition, reduces false alarms caused by subjects who have a known medical condition that triggers a system response but has no public health impact. A nationwide network of installed CA devices could provide disease surveillance with or without attribution for tuberculosis, and other emerging infections such as West Nile Virus, E. coli, Hepatitis C, Lyme Disease and Ehrlichiosis. Continual data streams could provide statistical wellness evaluations for subpopulations monitored by each of the 3,000 local health departments. Devices would be placed in public areas frequented by large numbers of people, and could also be installed in nursing homes and schools to help protect our most vulnerable citizens. The network could provide early warning of public health emergencies in advance of emergency room admissions reports, and would assist in determining their scope and tracking their progression regardless of cause. Rapid epidemiologic surveillance of an epidemic of swine flu, accidental HazMat release from a train derailment, polluted drinking water from a sewage plant malfunction, or terrorist release of a biological agent would all be supported by the same network.

Rapid, risk-free assessment of thermal, volumetric, and textural characteristics are correlated against observables associated with specific contagious diseases such as avian flu to yield a confidence measure that a person has contracted that disease. 3D/IR has unique benefits when large numbers of people must be quarantined. Because it can monitor each person's condition from a safe distance and link it to his identity without needing a health care worker or medical instrument to be in actual contact with the person each time, 3D/IR reduces the risk to health care workers, reduces contamination of medical instruments, and reduces the volume of hazardous waste such as examining gloves. Other related uses include documenting the identity of persons who receive a vaccine, and providing very early detection of adverse reactions.

An individual carrier of a highly infectious disease could infect thousands of other people by a single trip on a large commercial aircraft, or cruise ship. Infected individuals would spread the disease further before it was detected. This approach to suicide bombing may be especially appealing because it targets wealthier individuals, and would have an even greater impact on the airline and travel industries than 9/11.

More than 50 indicators of infectious disease can be automatically determined from a short sequence of 3D/IR facial imagery. These include: skin temperature, respiration rate, blink rate, lip tremours and body shivering, sweating, skin rash and other surface eruptions, hydration level, drooling, watery eyes, and fixed gaze. In place of IR cameras used for manual detection of SARS. 3D/IR performs identification against a Watch List plus screening for infectious disease.

Time-consuming speech and physical therapy are more efficient when 3D/IR sequences are used to provide quantitative 3D measurement of range of motion of head, hands, arms, and legs and to automatically track movements of specific muscles and resulting thermal changes without applying markers. Image sequences showing proper gait of a person walking are overlaid with corresponding imagery of a patient. Selected minutiae in each sequence are highlighted to provide visualization to the patient of changes he should make in his gait. Image sequences showing proper facial movements associated with speech or exercise are similarly processed and displayed to direct patient therapy.

Non-medical applications of the same systems include training actors (including digital actors) to mimic facial movements of persons they will portray and training sports enthusiasts to mimic the body movements of winning athletes.

3D Technologies

Structured light and laser radar range sensors provide 2D range images of objects at close (0.5 to 2.5 meter) and further (5-40 m) distances with depth accuracy on the order of 1 mm. Both approaches involve scanning. Movement of the human subject during the scan interval, including respiration and cardiac cycles, causes blur in the resultant feature map. Reduction in blur can be accomplished through modeling of the extracted anatomical features from each scan component. These range imaging techniques are well suited for medical imaging and long range security applications respectively.

Medical 3D imaging technologies such as CT scanning offer an alternate approach to implementing Body Mapping. The IR sensor, in the form of a single detector, linear (1D) detector, or focal plane (2D) array, can be coupled with the x-ray sensor inside the CT scanner. The constructed 3D/IR image then utilizes the range measurements created by the mechanism of the CT scanner. IR feature maps are continuously and automatically registered with CT images.

Various techniques can be incorporated to enhance the visualization of features or anomalies. For example, introduction of air currents or modulated heat source can increase visualization of anomalous areas.

Detailed Description of System with Reference to the Drawings

Principal Embodiment for Medical Image Standardization and Comparison

The primary embodiment of the present invention is a system that collects infrared, topographic, and optionally other modalities of two-dimensional medical imagery of a human subject, standardizes all images based on featuremaps extracted from the infrared image, and creates a library comprised of standardized medical images from many subjects. taken with various imaging sensors. The standardized image library is organized to facilitate automated search and compare to assist in diagnosis and prognosis of patients.

Essential novel aspects of the invention include method and apparatus for generating three-dimensional infrared images of any region of the human body, combined with methods for: extracting curvilinear line and spot features related to anatomical elements, applying IR-generated features to images from other sensors, standardizing the pose and position of images and features based on library reference rules, creating templates or encodings of the standardized features. Image header contents include encodings of: date, time, location, sensor, patient ID, condition, medical billing codes, system operator, prescribing physician and other characterizing data. Methods for assessing physiological changes and psychological profiles especially suited to the use of standardized images are also described with the primary embodiment, although other known image processing, database mining and search methods may be applied to the standardized imagery produced by this invention.

System Operation Flow

Without loss of generality, the system is described as having a specific orientation to the patient. The patient (FIG. 1) 100 lies on table 101 on his back with arms to the sides. Installed into the table are optional fiducials 111 in the form of rigid elements of varying heights, emissivities, and colors that are used to validate the calibration of topographic, IR, visual, and other sensors. The fiducials have sharply defined edges that can be clearly seen in all images generated by all imaging modalities used. The distribution of fiducials, is chosen such that a sufficient number will be seen in any imagery regardless of the size and positioning of the patient. Sensors already have had intrinsic and extrinsic calibrations. Fiducials provide continuous verification that all imagery is registered.

Figure 2:
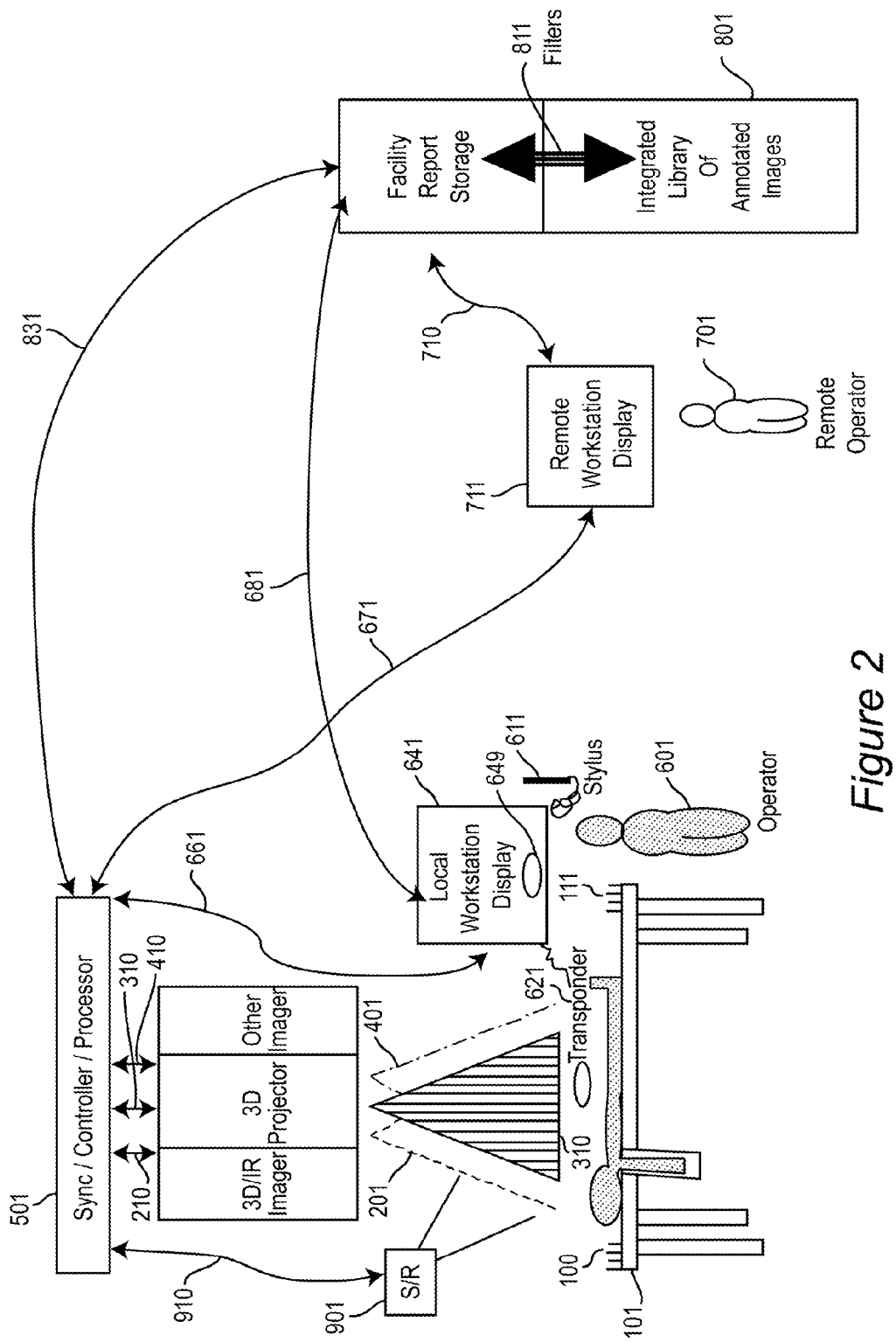
FIG. 2 is a schematic diagram of a side view of a patient being imaged on a 3D/IR imaging system.

Looking from the side of the patient (FIG. 2) a 3D/IR imager 201 is positioned such that its field of view encompasses the portion of the body to be imaged. Additional other imagers 401 may also be positioned to view the same portion of the body. These may be X-ray, NIR (near infrared), visual, and other imagers calibrated to the IR and topographic imagers, and collecting images simultaneously with those sensors. Integrated processing device 501 establishes system clock for synchronizing all image collection, processing, projection, and display. Bidirectional communications 210 provide trigger and synchronization to the 3D/IR imager and receives imagery from that imager. Bidirectional communications 410 provides trigger and synchronization to the other imagers and receives imagery from them.

Size, shape, and position of fiducials 111 in current IR and Topographic images is compared against the Master fiducial calibration images. Any deviation produces a change to the calibration transform. Synch/Controller/Processor 501 processes the common area 310 in the current IR and Topographic image fields of view, using the corrected calibration transforms to generate specific displays requested by operator 601 from the list of: IR featuremap, skeletonized IR featuremap, internal featuremap, vein map, artery map for the common area.

Operator 601 uses stylus 611 and virtual keyboard on Local Workstation Display 641 to enter and review patient's information and prescribing physician's request for specific imaging, entry of make/model/serial#/operating mode for each sensor, date/time/location/protocol/ambient conditions, subject ID code and link to background information (date of birth, gender, ethnicity, chronic diseases, pertinent medical history, previous imaging). Operator next uses stylus 611 to select imaging sensor options and image display options from pull-down menus on workstation 641.

Selections are conveyed 661 to sync/controller/processor 501 which triggers 201 and 401 to begin imaging and projector 310 to turn on and ready. SCP 501 performs the processing selected by the operator, corrects transform according to fiducial calibration, and sends the resulting image stream to high intensity color Projector 310 which projects the processed image onto the skin surface. 501 constructs specified derivative images of the common area in the current IR and Topographic images, using the corrected calibration transforms: It performs additional processing to produce: IR featuremaps, skeletonized IR featuremaps, range image isolines, horizontal-filtered range images, separated internal and external featuremaps, and separate vein/artery/external featuremaps for the common area. Each map is color-coded as per Setup selection when projected.

Figure 3:
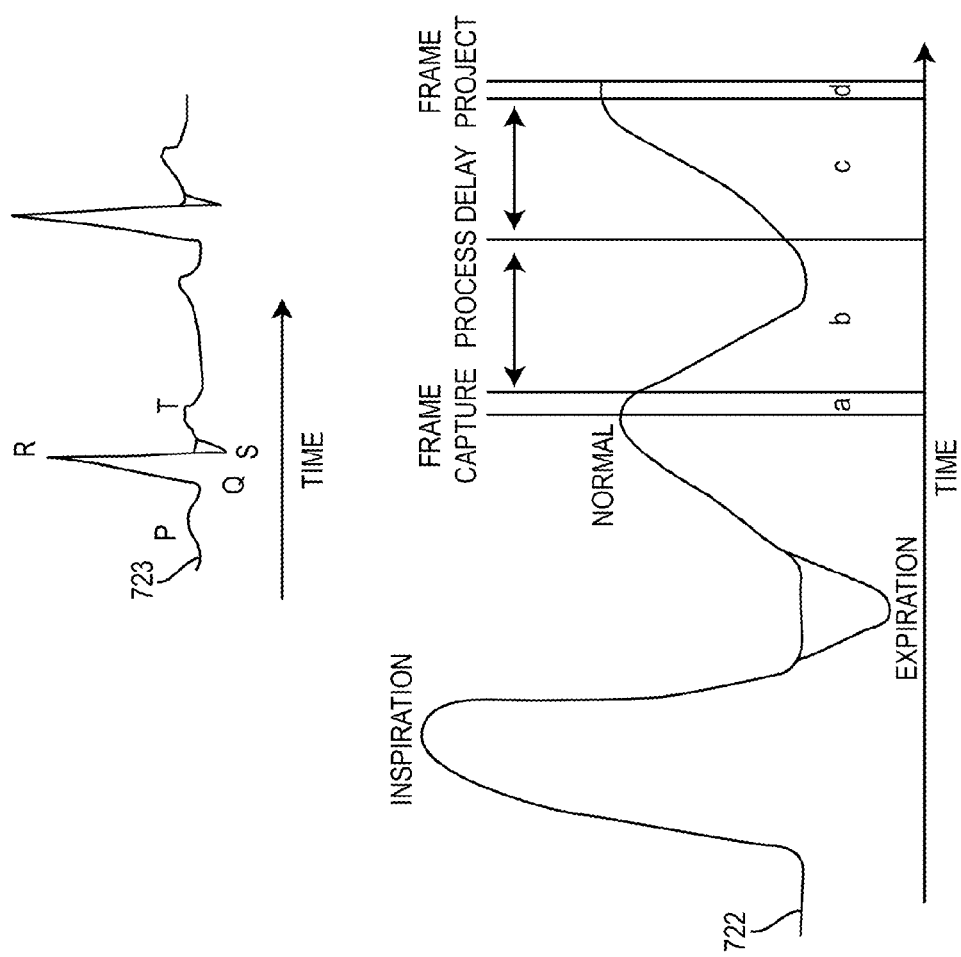
FIG. 3 is a graph of patient cardiac and respiratory cycles.

Operator 601 observes the projection on the body surface to guide a transducer 621 to position over the carotid artery. Transducer is a digital stethoscope, microphone, or ultrasound device that provides respiration and cardiac time signature through the LWD 641 to the SCP 501 via 661. To achieve best visualization and most accurate position of the projected image on the body surface, SCP 501 imposes a delay in the projection sequence (FIG. 3) to insure that the frame projected at time T represents the same point in the respiratory and cardiac signatures as the current patient state. The projected image is delayed one respiration cycle from its collection time 722a plus processing time 722b plus an imposed delay 722c such that the projection time 722d is precisely one cycle later than the collection time 722a. If processing requires additional time, then 722b can be greater than one cycle and 722c is calculated to register with the next cycle. Similar process can be used with cardiac cycle. If both cardiac and respiratory cycles are to be synchronized with projection, patient is instructed to take and hold deep breaths. The increased inspiration and expiration slows the respiration rate; allowing for better match between cardiac cycles.

Local Workstation 641 includes a display monitor, communications with SCP, and two peripheral devices; the stylus 611 and transponder 621. Stylus is used on the display and transponder is used on the patient. Both are wired or wireless devices. Either or both can be replaced by the finger or hand of Operator 601. LWS 641 has seven selectable 646 display modes which drive the collection of imagery, projection of imagery, and display of imagery and data. The seven modes are always shown as options for Operator 601. Display area 642 always displays patient and operator information in addition to list of areas to be imaged and list of imagers and transponders to be used.

Figure 4:
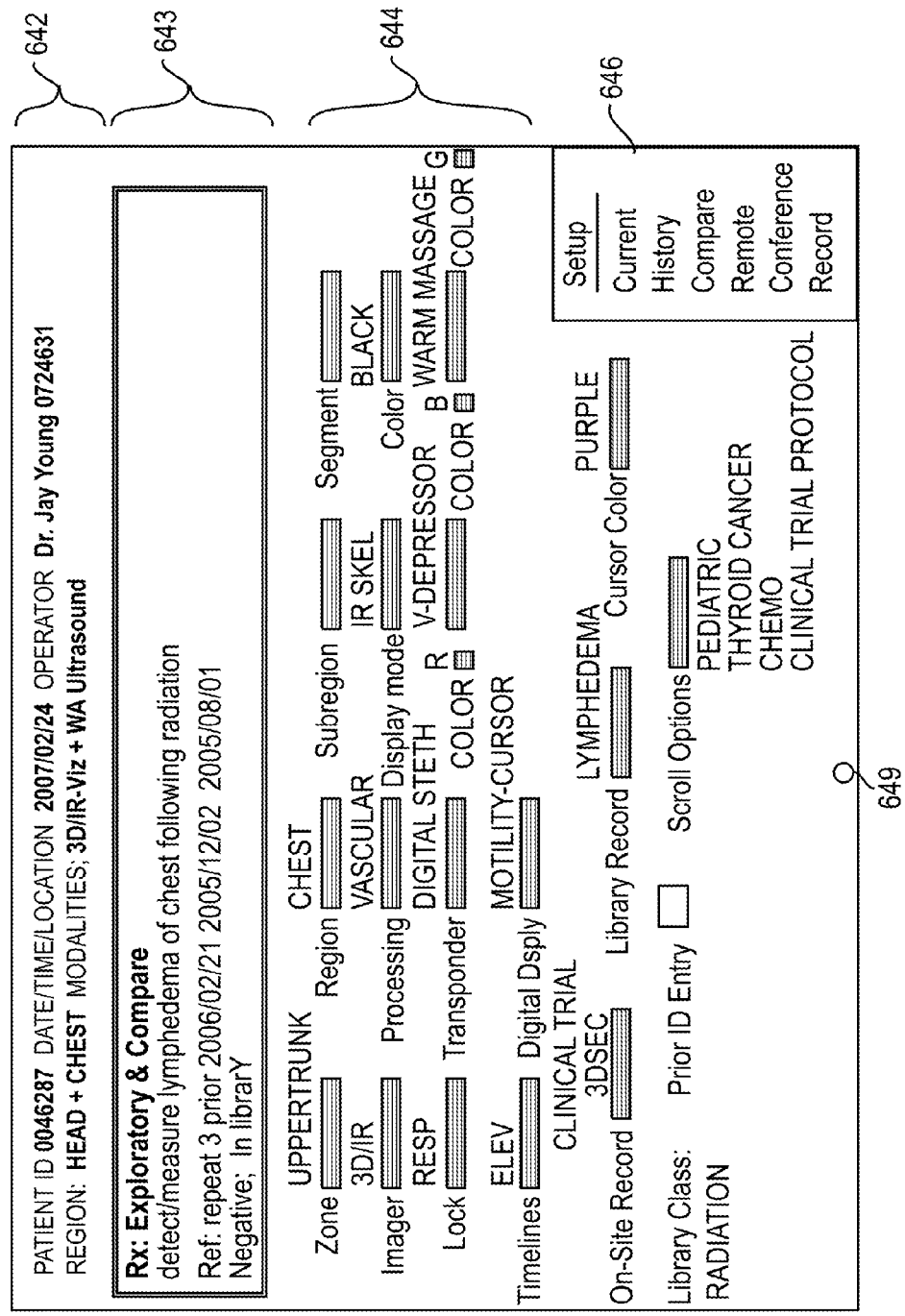
FIG. 4 is an exemplar setup display showing information for a 3D/IR imaging scan.

(FIG. 4) Setup Mode displays 642 patient information, date/time/location of the current imaging, identification of current Operator, designation of area to be imaged and imaging technologies to be used. Also displayed 643 are the prescription for imaging and references to prior imaging that is available to the system. Operator 601 enters instructions to SCP 501 via pulldown menus in 644 to select image collection and projection. In this example, he selects the Chest region, requests 3D/IR imaging with processing to enhance Vascular features, and display of IR Skeleton projected in Black. Projection is to be locked to Respiration cycle as determined from a Digital Stethoscope. Timeline displays will be Elevation, Temperature, and Motility at the location selected by stylus 611. Transponders used will be the digital stethoscope, calibrated weight for vertical depression of skin, and warm massaging skin buff to accelerate lymph movement. Disposition of imagery is selected, including: classification for on-site storage 831, in this case a Clinical Trial, and for the Integrated Library 801, in this case Lymphedema and Radiation. Confirmation of ID and prior entries in the Facility and Library Storages is checked. Additional keyword descriptions are selected, in this case pediatric, thyroid cancer, chemo treatment, and clinical trial protocol. Multiple pulldown menu entries can be selected in each instance.

Figure 5:
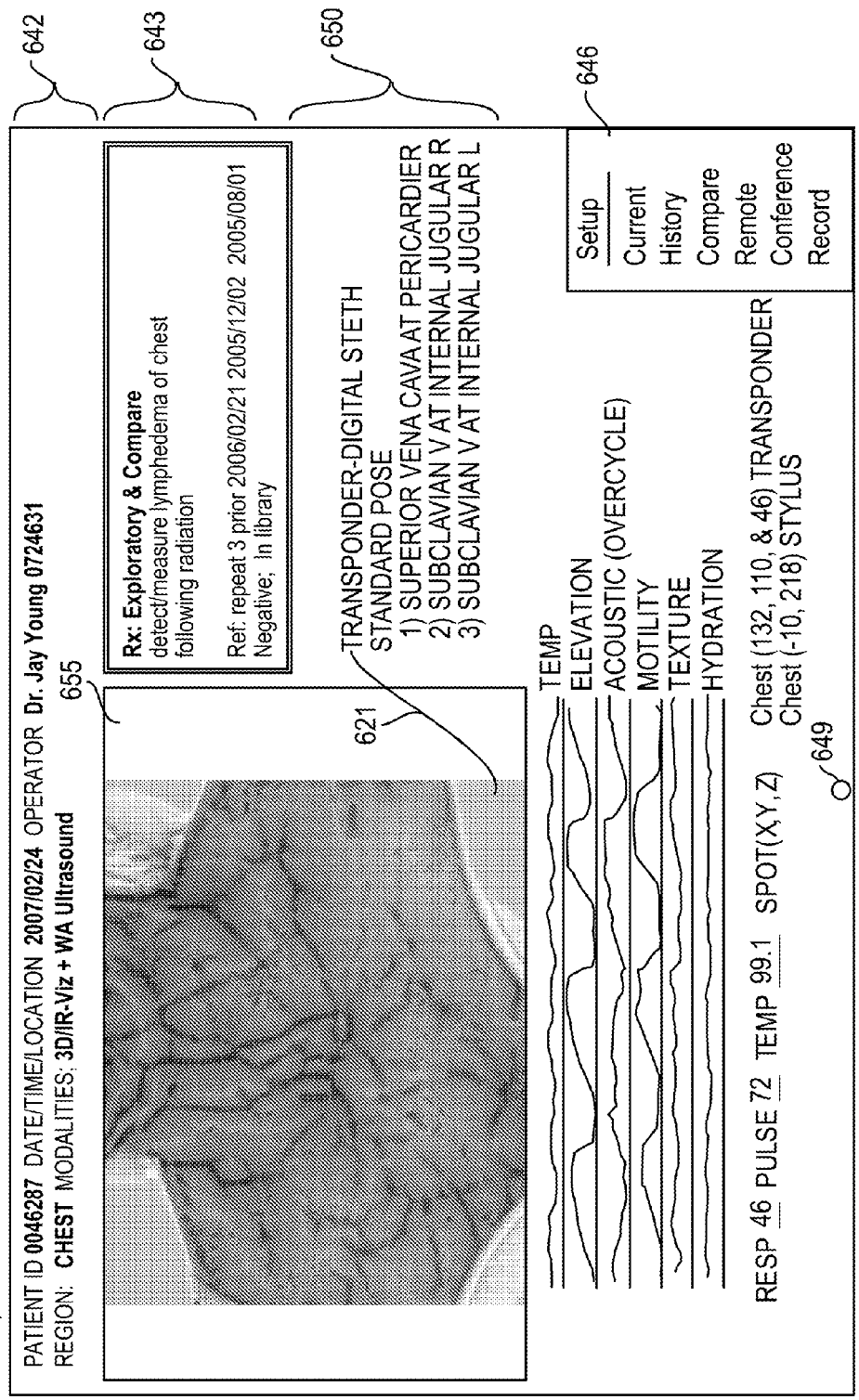
FIG. 5 is an exemplar current display showing a feature map projected onto the chest region of a patient showing an enhanced vascular overlay.
Figure 6:
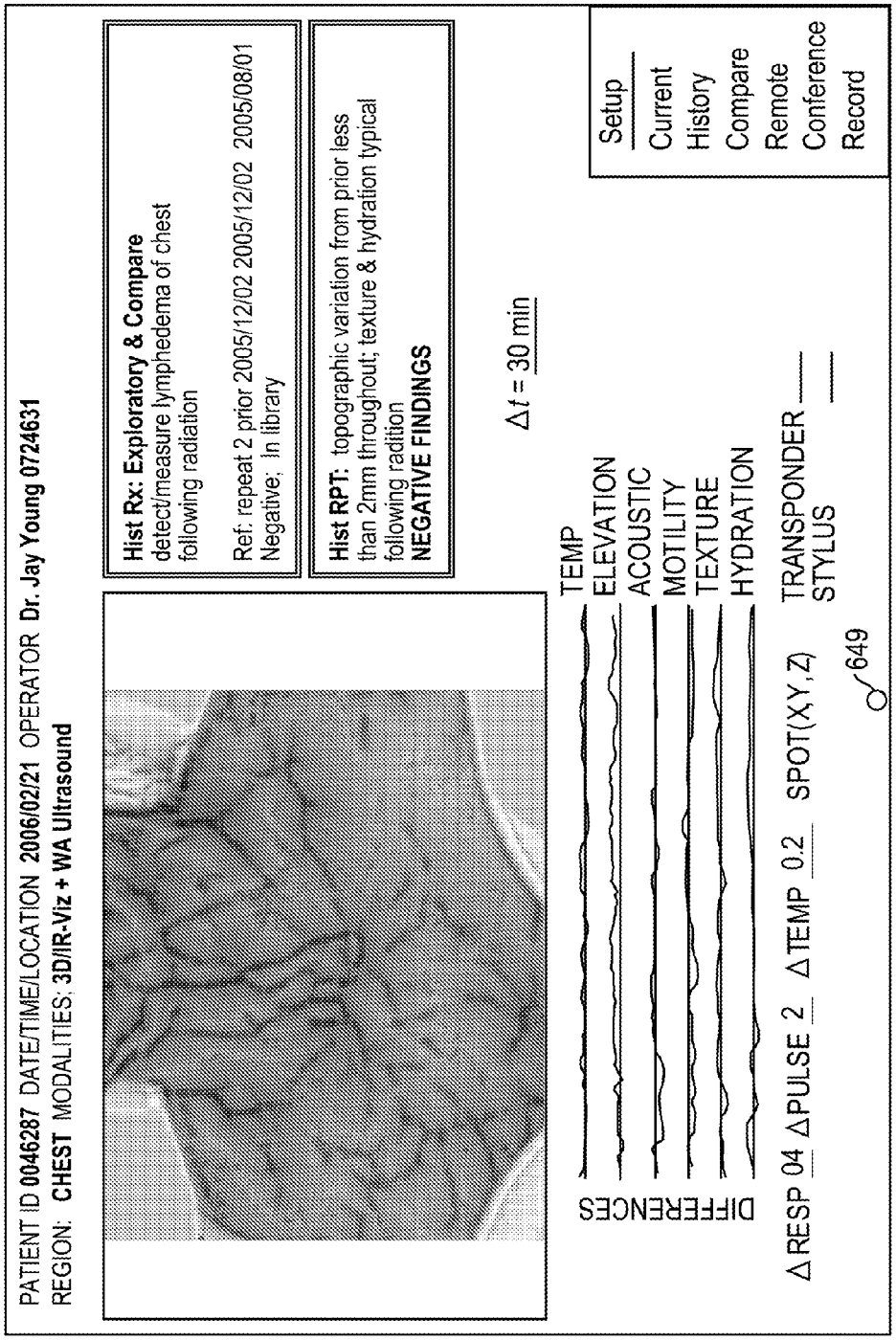
FIG. 6 is an exemplar history display listing prior tests and replaying a selected test.

To initiate imaging, Operator selects the Current Mode 646 which changes the display screen to FIG. 5. Setup information blocks 642 and 643 are shown. An image window 655 displays realtime imagery as selected under Setup. Here it is 3D/IR with enhanced vascular overlay. Position of transponder 621 digital stethoscope can be seen in the image as silhouette. Display block 650 lists current Transponder in use, here the digital stethoscope, and the designated three anatomical locations that define the standard plane for this area of the body. Here they are (1) superior vena cava at pericardium (2) subclavian vein at internal jugular on the right and (3) on the left. Operator uses stylus to select the three standard reference points; first touching the name of the reference point to be located and then touching the corresponding point on the image display 655. Here the three points are shown with rings. Cursor color was selected during setup to be purple. When stylus is held on a display location, the temperature, elevation, and acoustic curves in block 650 have purple timelines for the cursor location overlaid on the black timelines for the transponder. This feedback assists the Operator in determining that he has selected the correct standard reference points for the Chest region. Operator may change reference points by selecting number 1, 2, or 3 and then selecting a point on the display. Locations of the transponder and stylus are both reported in standard mode coordinates, although the image display is shown as seen visually.

Operator uses stylus to direct rotation of the displayed image in three dimensional space to enhance visualization of thermal, visual, and topographic image features. Rotating the image blanks the projection onto the skin surface.

Operator may select History Mode 646 and designate the time interval for comparison. In the example, the interval is selected to be 30 minutes. If setup is not changed, display continues to be vascular overlay on IR image. But now in the History Mode, display is the difference between vascular-overlaid IR currently and from 30 minutes previously, synchronized to respiration. The timelines displayed also represent differences, as do digital values of respiration, pulse, and temp at specific cursor and transponder locations. Operator enters his History Report via voice, keyboard, or virtual keyboard. In this example, elevation did not increase more than 2 mm during the 30 minute interval, and no other anomalous data was seen. Therefore, results of this test are negative.

Figure 7:
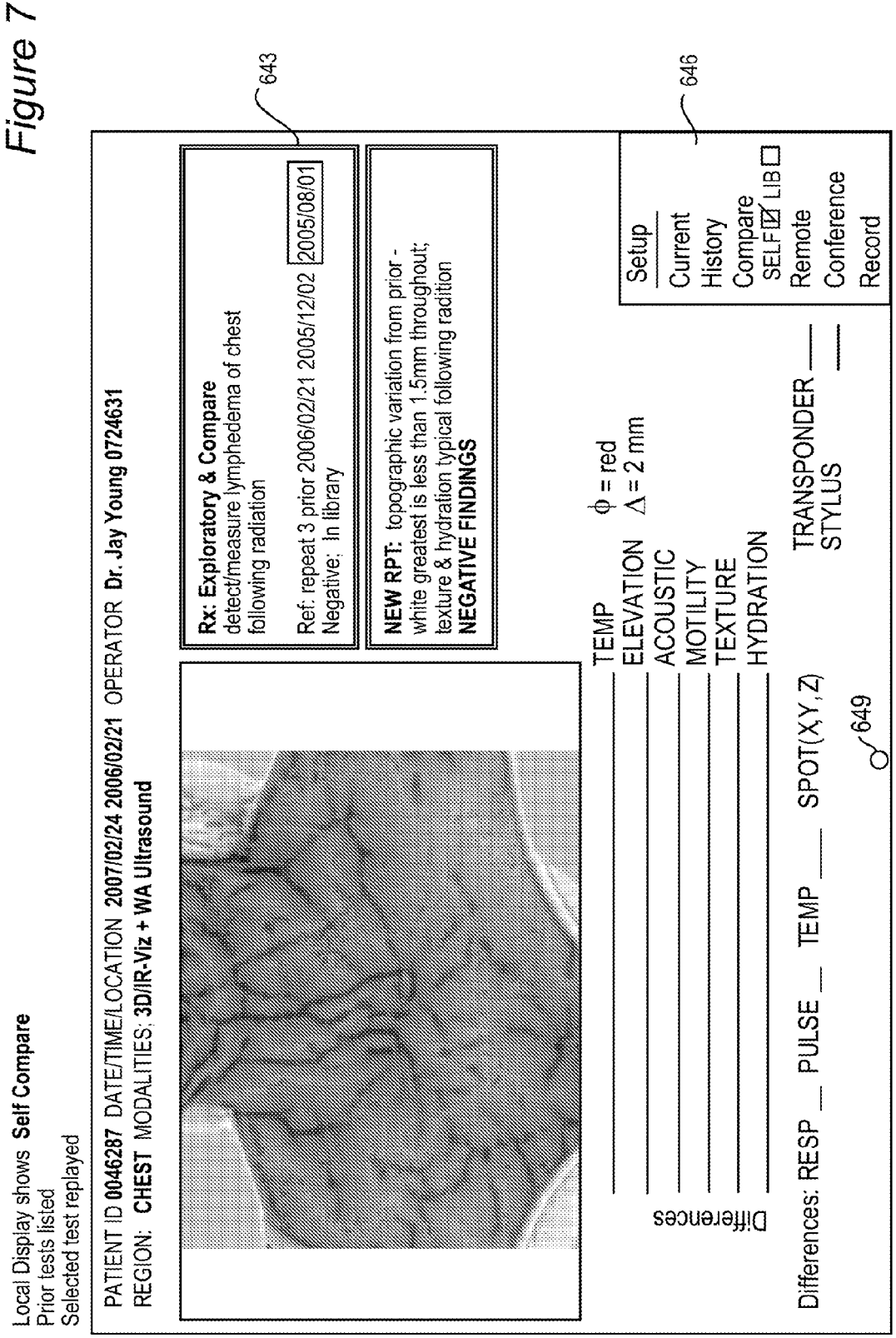
FIG. 7 is an exemplar self compare display listing prior tests and replaying a selected test showing vascular variations between the current image and a prior image.
Figure 8:
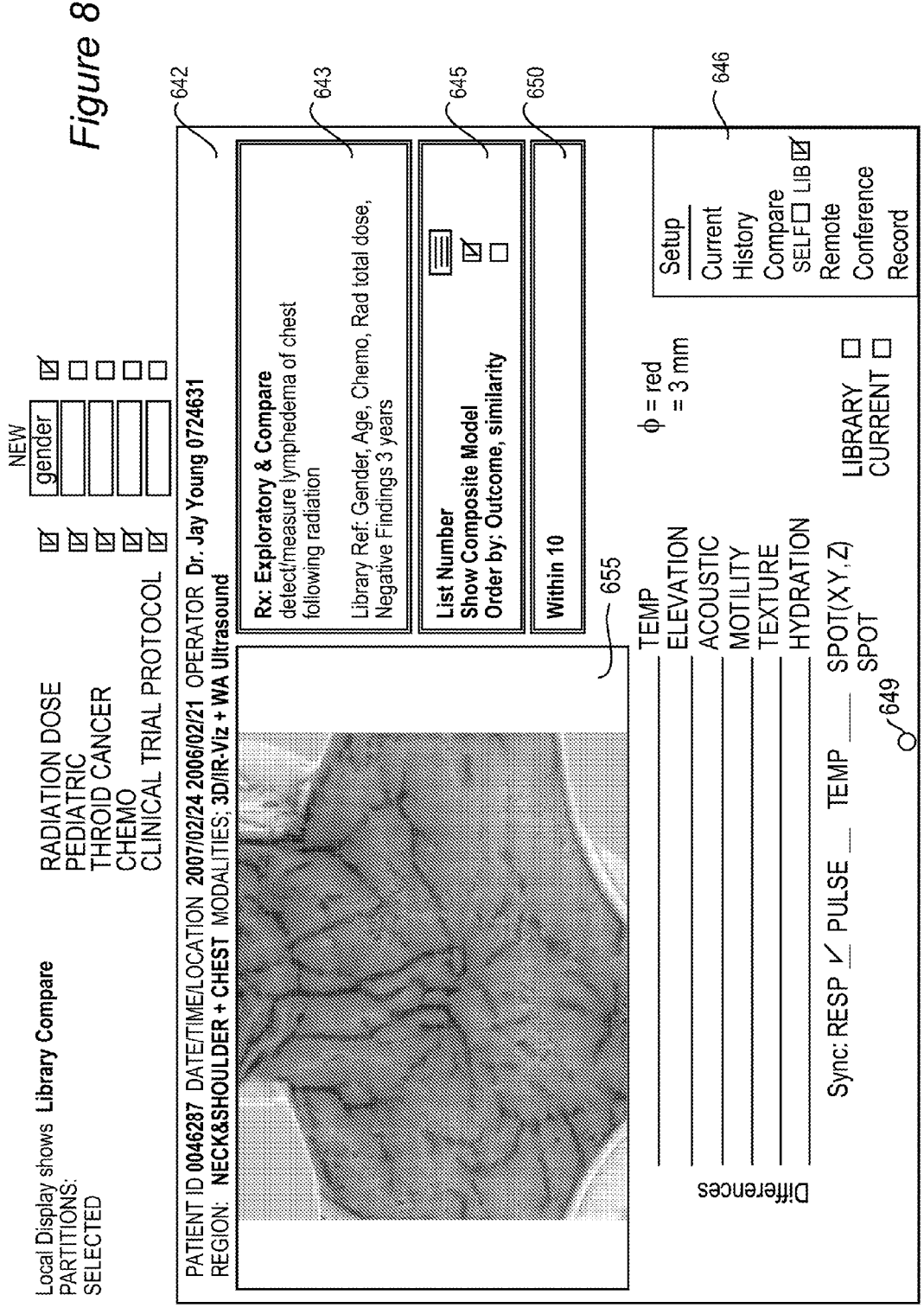
FIG. 8 is an exemplar library compare display listing partitions and showing differences between the current topographic image and a composite of all library images within the selected partitions.

If Operator returns to Setup and selects Compare, the imagery changes as shown in FIG. 7 where vascular variations between the current image and prior date imagery of the same person is displayed. The prior date image is selected from block 643 in this example 2005/08/01. The prior imagery is transformed to match the current pose, position, and orientation of the patient through use of the three-point standardization transform created for the prior date imagery and the current three-points for standardization. The display encodes topographic variation into grayscale with white the greatest variation. Operator sets a threshold here selected to be 2 mm, which results in vascular structure showing as red in locations having elevation difference equal or greater than 2 mm between current and prior tests. No red is showing, meaning no variation exceeds 2 mm;

Operator returns to Setup and selects Topographic display mode and then Compare Library. If he has not previously selected library partitions to be used, he does so now using the Library Class and Options listings and selecting those to be used. He then selects Compare Library and the Local Display updates to FIG. 8 where Display Image 655 is the difference between the current Topographic image and the composite library image formed from all persons within the selected library partitions. The standardized composite library image is transformed to overlay on the current image using the three defined image standardization points, so that the difference image displayed is in the same pose and position as the current image. Static image frame may be displayed, or sequences; in either case, the images are corrected for respiration effects. When no stylus position is selected, the difference data 650 is blank. Due to extent of variation in anatomical structures of different people, library compares are generally done at sub-region level.

Figure 9A:
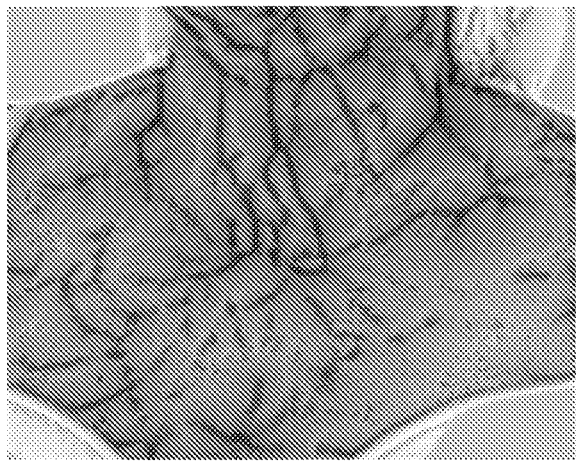
FIGS. 9a and 9b, respectively, show the current typographic image and the effect on the displayed image of removing a comparison filter limiting the library images to those patients who had undergone chemotherapy.
Figure 9B:
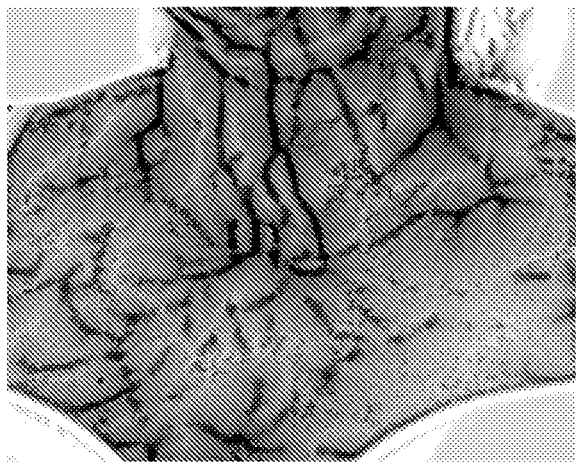
Figure 10A:
FIGS. 10a and 10b, respectively, show a current image with a changed image mode, designed to the effects of estrogen, and a prior image with the same selection of optics.
Figure 10B:
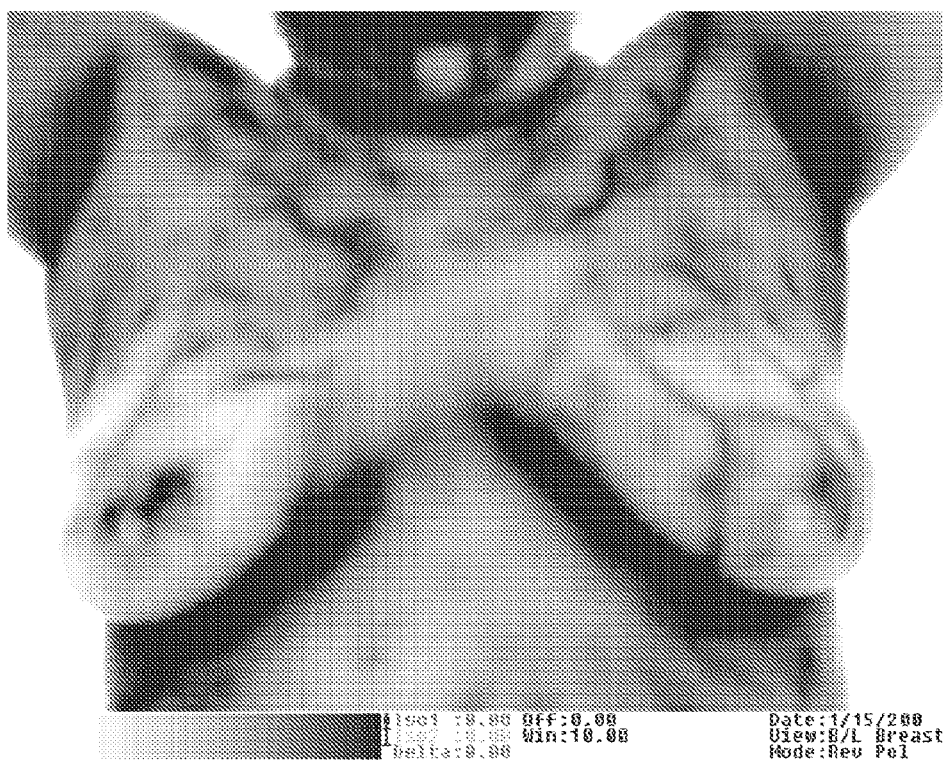

Operator selects Current to display the current Topographic image as in FIG. 9a in display area 655, or selects Compare Library and deselects Chemo which changes the library images used to form the composite that is differenced with the current image. FIG. 9b illustrates the effect on the displayed image caused by removing the requirement that library images used in the comparison be from persons who had undergone chemotherapy. In this example, maximum elevation differences are 50% greater when chemotherapy is not performed. Operator would update the reporting area 650 to state that conclusion.

Another Operator 701 is at a Remote Workstation Display 741 with stylus 711. He performs the same workstation functions as On-Site Operator 601 but cannot apply the transponder to the patient nor establish the initial patient pose and position relative to the imagers. When a Remote Workstation is in operation, the Remote Mode indicator 646 is lighted on the Local Workstation Display 641.

Conference Mode is selected at the Local Workstation Display 646 which enables Audio Link 649 among Local Workstation and one or more Remote Workstations. Remote Operators provide comment on the Setup selections to choose imagers, synchronization, and other options. Remote Operators can independently each use their own stylus to observe data during the imaging. Reporting area 643 of the Local Workstation Display and at each Remote Workstation Display 743 includes all reports from all workstations collaborating in Conference Mode.

Operator in individual or conference mode returns to Setup to select Current image mode of IR and displayed region of Chest+Abdomen which causes change in optics and results in displayed image 10a. Change to History mode and selection of a prior date results in displayed image 10b. In the example, estrogen use or contrast material during the earlier period provides greater visualization of vascular structure than is available in the current image. Historical skeletonized featuremap is transformed from standardized pose to match the current patient pose, and is projected onto the patient. This approach removes the requirement to inject contrast agent for current assessment in certain situations where earlier use of contrast agent produced standardized featuremaps.

Record Mode is selected to save imagery, data, and reports in Facility Report Storage 831 via communications 681 with LWS 641. Privacy filters and access filters 811 are applied to information recorded in Facility Report Storage 831 before filtered information is available through the Integrated Library of Annotated Images 801. Filters strip or encode identification and other text information in compliance with privacy laws. Filters also establish access requirements for annotated images entered into the Library 801; for example, results associated with clinical trials are restricted to authorized collaborators in those trials. All library imagery is standardized with appropriate header information to enable its use in future library search: make/model/serial#/operating mode for each sensor, date/time/location/protocol/ambient conditions, body zone/region/subregion, subject ID code and link to enrollment information (date of birth, gender, ethnicity, chronic diseases, pertinent medical history, reason for current imaging)

Secondary Embodiment for Patient and Staff Identification

3D/IR is used to produce unique identifying featuremaps and encodings when no other means of identification is available for a patient, when other means of identification is suspect, and to control access to patient records and physical areas. Identification is performed using the same featuremaps developed in the primary embodiment. The identification process can be added to the system (FIG. 2) of the primary embodiment. However, privacy of patient identification information must generally be maintained, and identification of medical workers is not part of patient image library. Separation of patient identification and patient medical records can be assured through a combination of security procedures and hardware within the same system. For the purpose of clearly presenting details of the identification function, it is presented as a stand-alone system.

The 3D/IR system collects infrared, topographic, and visual two-dimensional imagery of a human subject, standardizes all images based on featuremaps extracted from the infrared image, and creates a library comprised of standardized images and featuremaps from all subjects. taken with various imaging sensors. The library is organized to facilitate automated search and compare to assist in identification of individuals who may be patients or health care workers.

Essential novel aspects of the invention include method and apparatus for generating three-dimensional infrared images of any region of the human body, combined with methods for: extracting curvilinear line and spot features related to anatomical elements, standardizing the pose and position of images and featuremaps based on library reference rules that specify three anatomical points in skeletonized 3D/IR featuremaps, and creating templates or encodings of the standardized features to speed matching and reduce storage requirements. Image header contents include for patients: encodings of date, time, location, sensor, assigned code for ID, medical billing information, address, next of kin, and other personal information. For health care workers: ID number, social security number or work permit, name, department, certifications, authorized entry areas, authorized systems use, current shift schedule.

Image Capture and 3D/IR Image Generation

Figure 11:
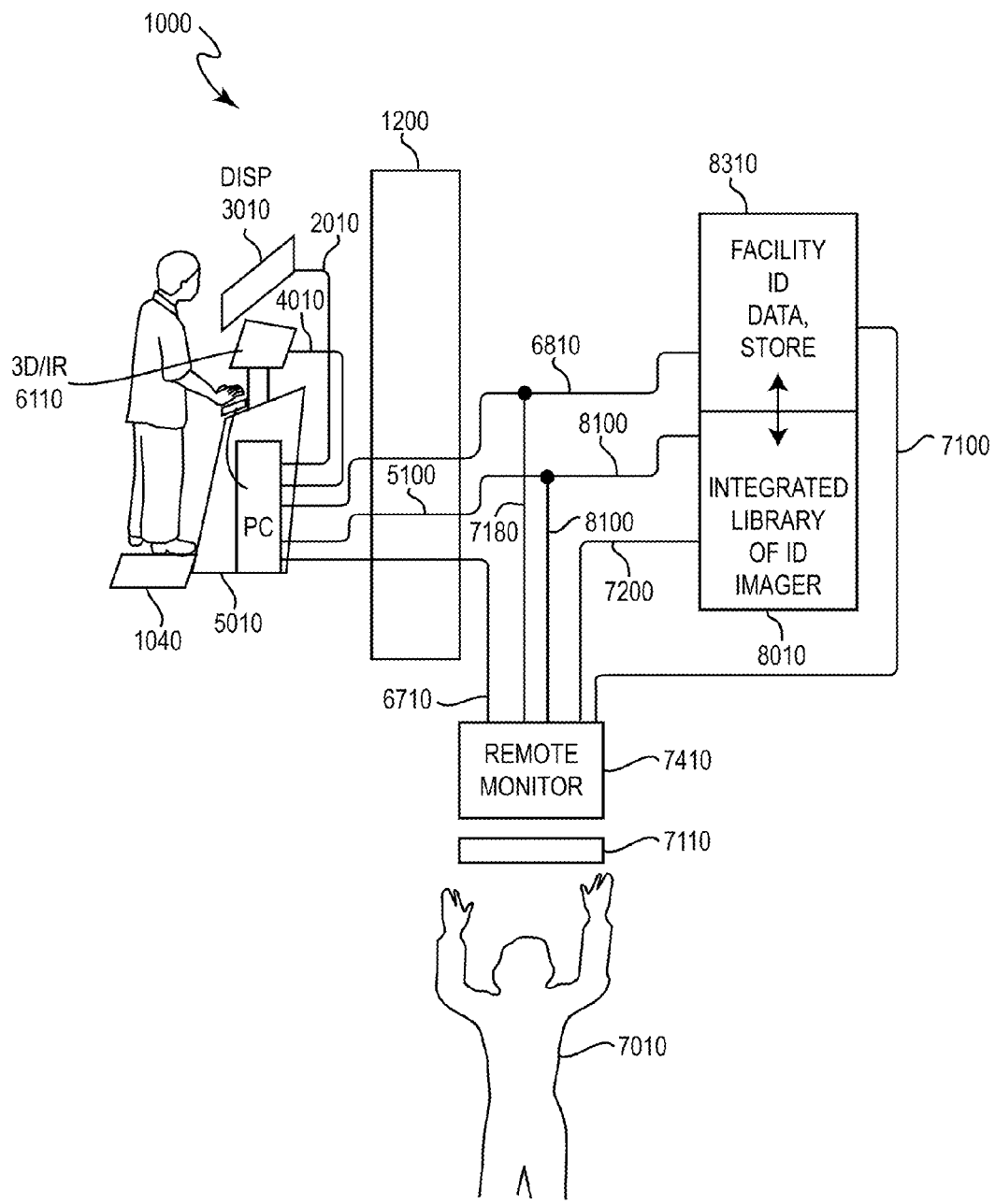
FIG. 11 is a schematic diagram of an image capture and identification system that does not require an operator.

Without loss of generality, the identification system of FIG. 11 is described as having a specific orientation to the person being identified and imaging a specific Region of the body. The person being identified is a patient or a person seeking access to a physical area or to medical records. Without loss of generality, FIG. 11 illustrates 3D/IR identification of a person within the field of view of the imaging sensor without requiring a Local Operator.

Person 1000 activates proximity sensor 1040 which activates the system. (Optional) Instruction display 3010 induces Person to assume a desired general pose and position relative to the composite imager comprised of 2010 3D/IR and 4110 Visual imagers. Person uses (optional) control 6110 to request access to a selected area, data file, or system. Imagers 2010 and 3010 collect synchronized and calibrated imagery of Person's body region. Imagery is transmitted to processor 5010 which automatically extracts background from body imagery, estimates pose using range contours and edges, determines presence of symmetry plane for horizontal and rotational axes, extracts 3D/IR featuremap and skeletonized featuremap, locates specified anatomical locations on the skeletonized featuremap defined for standardization of that body region or subregion, standardizes the featuremaps such that the three anatomical locations define the standard plane, the centerpoint is the centroid, vertical orientation of vascular structures is maximized and pitch variance is minimized.

Resulting standardized featuremap and skeletonized featuremap are annotated with overlaid annotation indicating location of anatomical standardization reference points. (Optional) additional overlaid annotation includes local anomalies extracted from visual, IR, and range images. Processor 5010 produces identifying 3D/IR standardized featuremap template, standardized feature node template, encoding from standardized featuremap or node templates, matching identification files from Facility DataBase 8310 accessed via facility network 6810 via link 7180, and matching identification files from Integrated Library of ID Images 8010 accessed via wide area network 8100 via link 8100. Processor 5010 makes access/no access decision for Person 1000 to access area/equipment/information 1200 and enables lock or unlock condition. Optional) Remote Operator 7010 observes realtime imagery on Remote Monitor 7410 and can override the decision via communication channel 6710 with the Processor. Remote Operator 7010 can access ID imagery from Facility DataBase 8310 and Integrated Library 8010 for side-by-side comparison on Remote Monitor 7410 with imagery of current entrant 1000.

Figure 12:
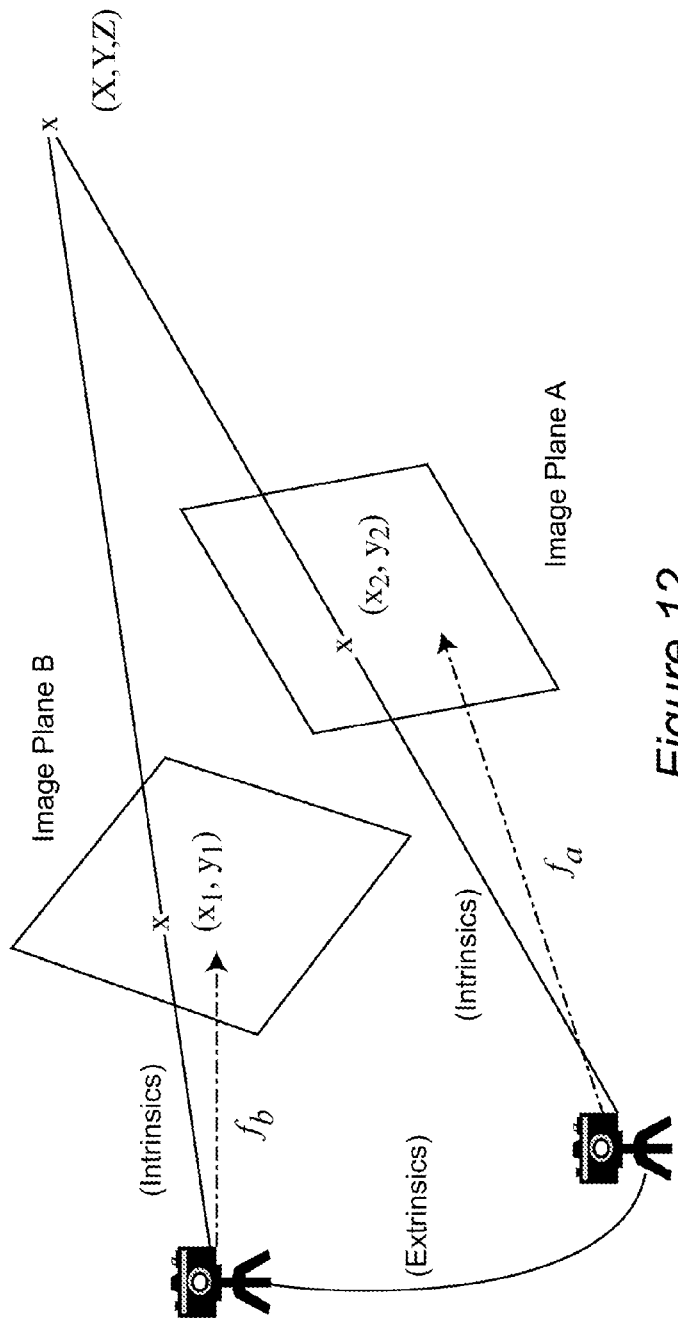
FIG. 12 is a chart and diagram showing calibration of system imaging sensors.

Without loss of generality consider the body region to be the face in an uncontrolled pose. System imaging sensors for IR, elevation, and visual imagery are calibrated as per FIG. 12 for the distance to subject person. Calibration target is positioned at a distance f (focal length) from each imager. Reflection or emission off a 3D point (X,Y,Z) toward the imager impinges this plane at a point (x,y). The point (x', y') on the sensor array at which this ray is collected is distorted by several factors, including lens aberrations, radial distortion, detector array nonregularities, and other biases that deflect the ray and cause an overall distortion of the image. Corrections needed to reverse the effects of these distortions are computed and referred to as the intrinsic parameters for that imager. Registration of images from multiple imagers requires extrinsic calibrations to obtain each imager's extrinsic overlay transform to compensate for different locations, fields of view, and aspect angles of the different imagers and enable translation of image coordinates from one imager's coordinate frame to another's coordinate frame. Parameters are computed and referred to as the extrinsic parameters.

Intrinsic parameters:
Focal Length (fx, fy)
Image Center (principle point) (ox, oy)
Pixel Size (sx, sy)
Radial Distortion Coefficients (k1, k2, ... )
Tangential Distortion (p1, p2, ... )
Extrinsic parameters:
Translation Vector (tx, ty, tz)
Rotation Matrix $$\begin{pmatrix} r11 & r12 & r13 \\ r21 & r22 & r23 \\ r31 & r32 & r33 \end{pmatrix}$$

Combined calibration parameters:
(from PhotoModeler)

| | |
|---|---|
| # Control Points | 8 |
| Center X (mm) | 320.247 |
| Center Y (mm) | 515.2615 |
| Center Z (mm) | 1087.192 |
| Focal Length (mm) | 67.79046 |
| Format Height (mm) | 16.777654 |
| Format Width (mm) | 20.2074 |
| FOV H (deg.) | 16.954305 |
| FOV W (deg.) | 4.108571 |
| Image Height (pixels) | 512 |
| Image Width (pixels) | 640 |
| Kappa (deg.) | 91.16814 |
| Omega (deg.) | 20.1560 |
| Phi (deg.) | 6.555032 |

| | |
|---|---|
| Principal Point X (mm) | 8.294885 |
| Principal Point Y (mm) | 9.247519 |
| K1 | 0.000029 |
| K2 | 0.000000 |
| P1 | −0.000080 |
| P2 | −0.000077 |

Figure 13:
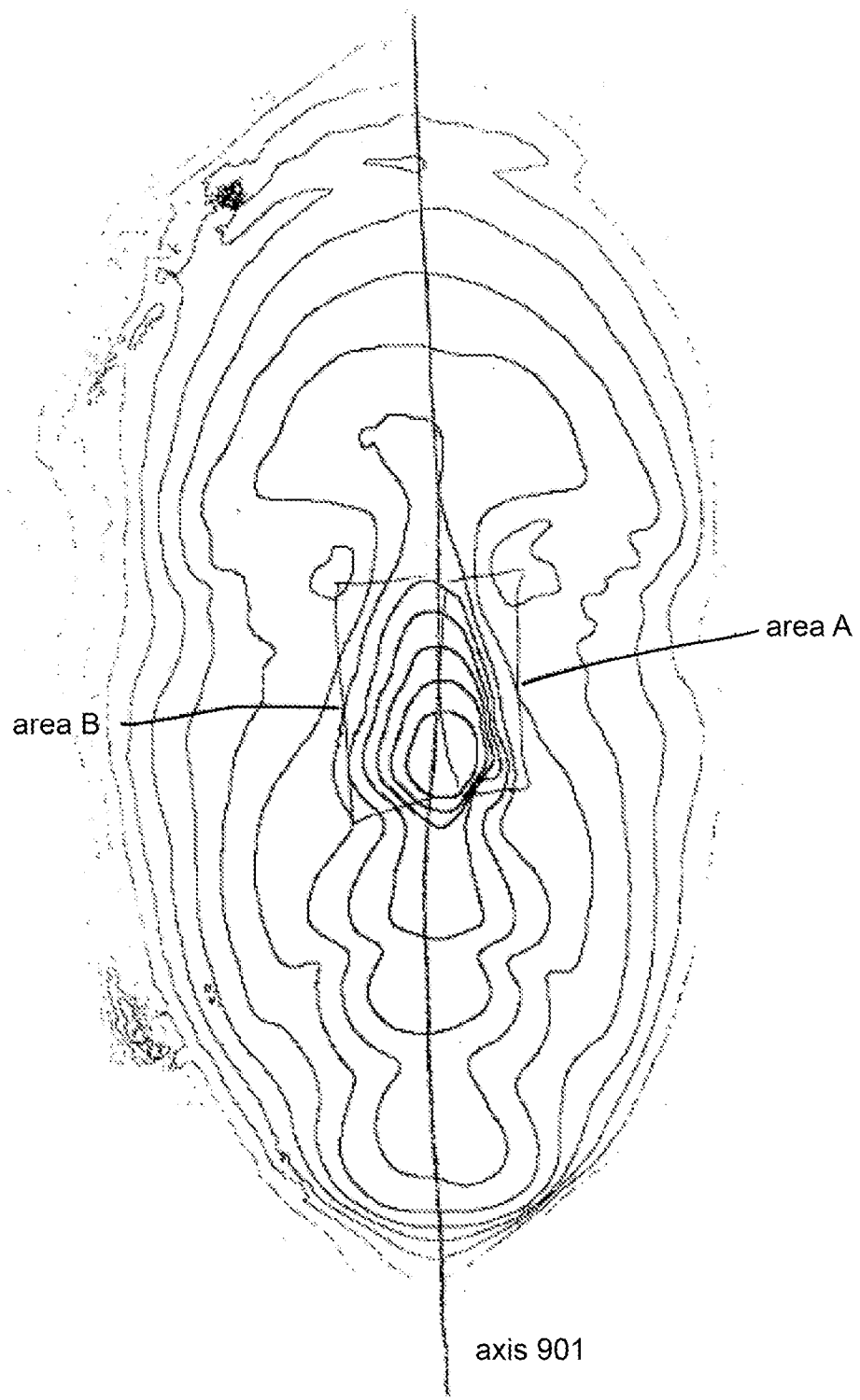
FIG. 13 is a display of nested conformal isolines having intervals sufficient to distinguish external features and skin creases, enabling use of symmetrical disparities to determine relative orientation.
Figure 14A:
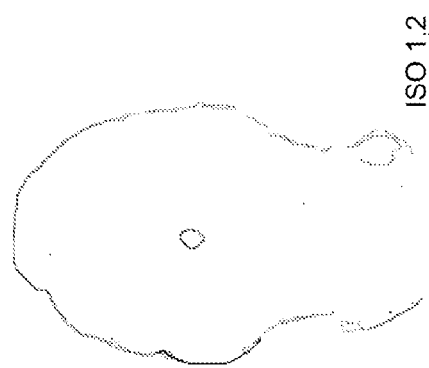
FIG. 14 compares isoline diagrams (as in FIG. 13) with corresponding images to show orientation.
Figure 14D:
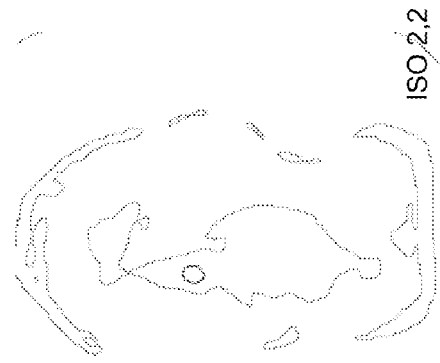
Figure 14B:
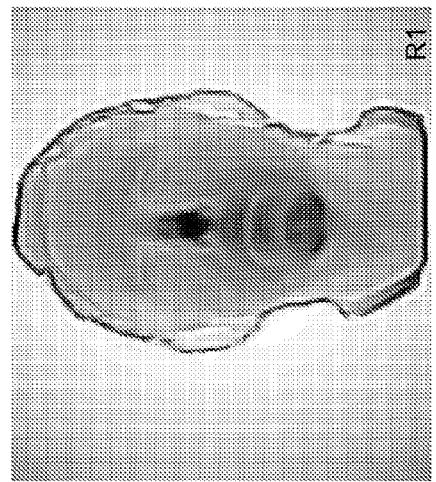
Figure 14E:
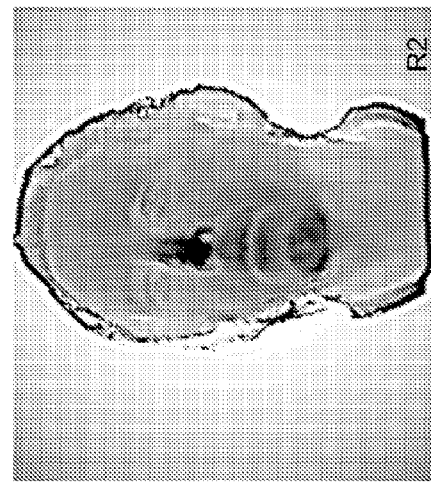
Figure 14C:
Figure 14F:
Figure 15:
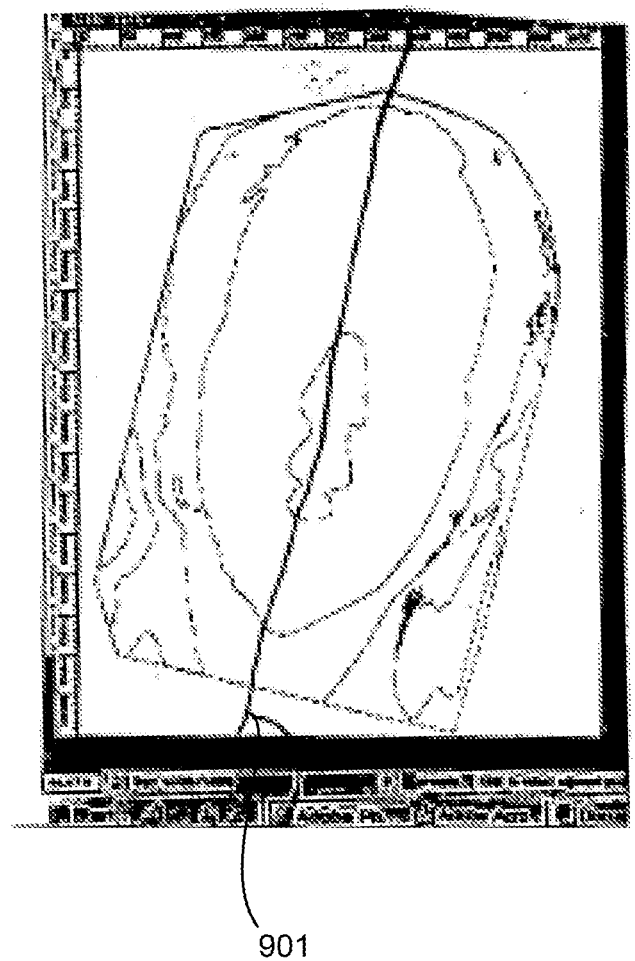
FIG. 15 shows an isoline diagram having an axis of symmetry indicating a skewed facial orientation.
Figure 17D:
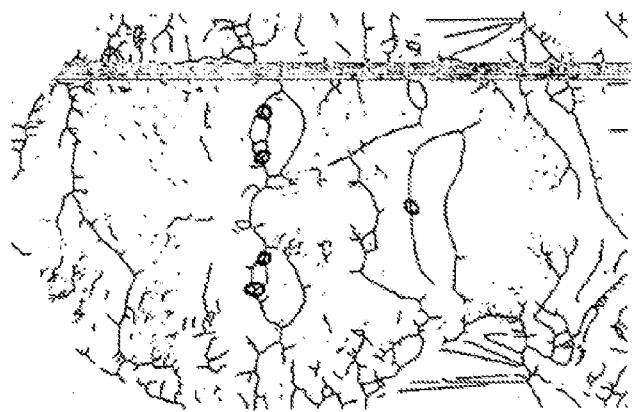
FIG. 17a shows a range image, which is filtered in FIG. 17b to extract edges, thresholded in FIG. 17c, and skeletonized in FIG. 17d to produce pixel-level designations of inner and outer eye corners and upper lip center represented by dots.
Figure 17C:
Figure 17B:
Figure 17A:
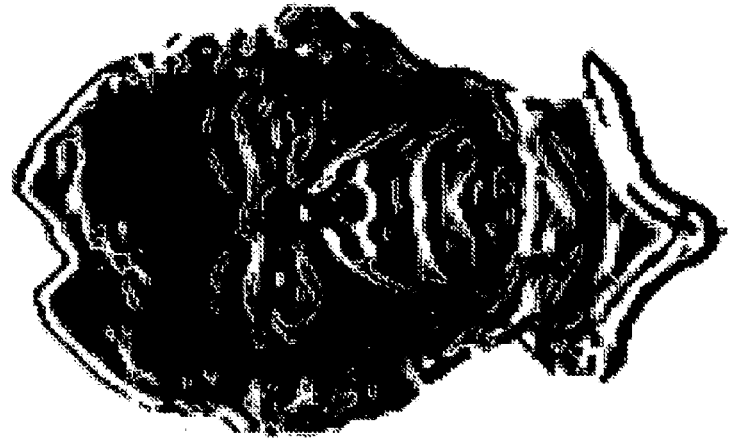

System is triggered, captures one frame each of topographic, infrared, and visual imagery and constructs 3D/IR-Visual model of the face using calibration parameters. Result is three overlaid and registered layers of imagery. Range image layer is processed to find isolines FIG. 13 with sufficient nested intervals to distinguish external features and skin creases; on the order of 3 mm for face regions, 5 mm for neck region, 1 mm for hands. Regularity of spacing between isolines indicates degree of topological symmetry of the region, which correlates with rotation and tilt angles of the head. Spacing in area A is less than spacing in area B indicating body area represented by A+B is turned towards A slightly. FIG. 14 Iso1,1 indicates approximate frontal rotation for range image R1. Iso1,2 indicates nose is closer to imager than is chin, providing assessment that face plane tilt is approximately perpendicular to imager. Iso2,1 indicates face rotation to the right of frontal. Iso2,2 indicates tilt still approximately perpendicular. Axis of symmetry for 901 in FIG. 13 is approximately vertical, indicating that face is not significantly skewed (ear to shoulder rotation). FIG. 15 indicates axis 901 position in skewed face.

Featuremap and Skeletonized Featuremap

The method of the present invention uses skeletonized vascular features derived from thermal infrared images to define subpixel landmarks located at specific major anastamoses of blood vessels. Although blood vessels may subtend several pixels in width, and their diameters may vary with drugs, medical condition, exercise and other influences, the skeletonized representation is significantly more constant. By defining specific blood vessel branchings common to every person, vascular-centric standardization of any area of the body may be performed. Prior patents of the same inventor deal with the use of minutiae defined in this way for standard positioning and registration of patient images, and for sensor fusion.

IR and range images are collected simultaneously. Filtering steps are performed in combination and sequentially to produce a set of curvilinear and spot features, together with characteristics that describe each such feature and its relation to other features. Filtering steps include: edge-preserving noise reduction, contrast enhancement, edge detection, locally adaptive histogram equalization, horizontal and vertical edge detection, centerline determination, branch point determination, and anomaly removal. Specific filters used, and parameters for each, are dependent upon the IR imaging system. In particular: detector array size, pixel pitch, fill factor, thermal sensitivity, instantaneous field of view, optics quality, focus precision, depth of field, bad pixels, non-uniformity, and noise. Resultant IR featuremaps are considered unique to the individual and essentially persistent in spite of ambient, physiological, emotional, and other variations that occur on a daily basis.

Figure 19C:
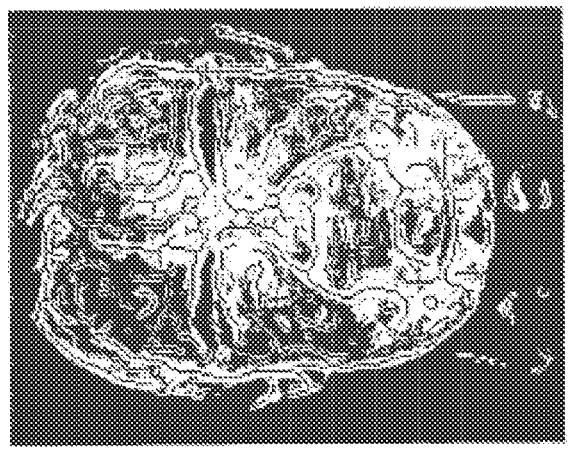
FIG. 19 shows an IR image that has been variance equalized followed by local adaptive equalization and skeletonization to produce an IR skeleton image.
Figure 19B:
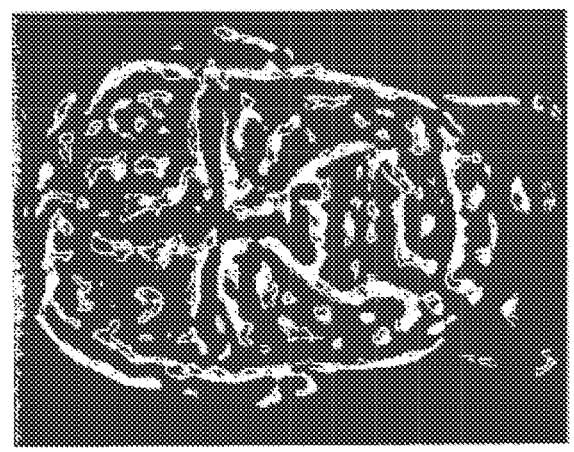
Figure 19A:
Figure 20A:
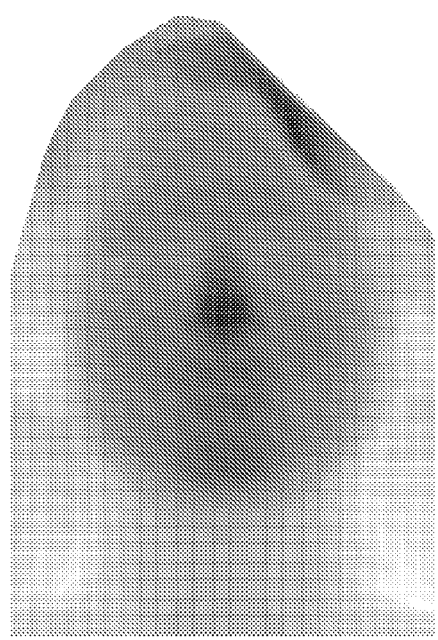
FIG. 20 is shows a range image that has been variance equalized followed by local adaptive equalization and skeletonization to produce a range skeleton image.
Figure 20B:
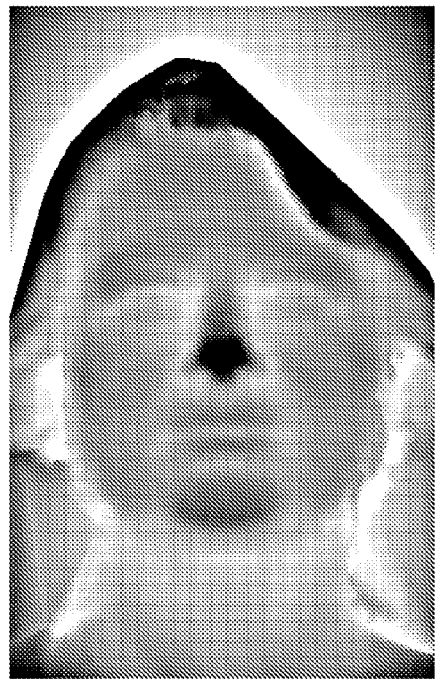
Figure 20C:
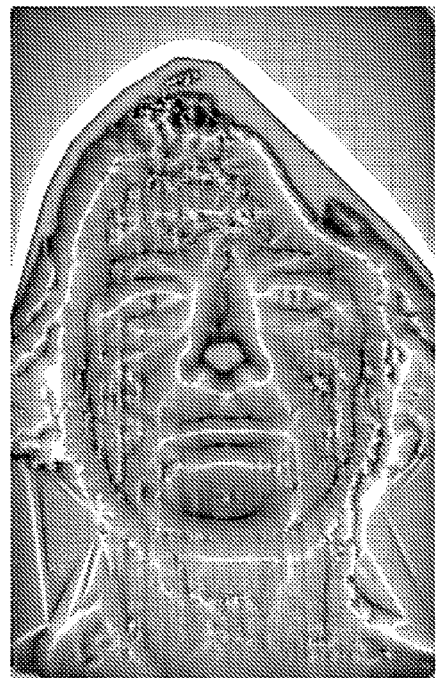
Figure 20D:
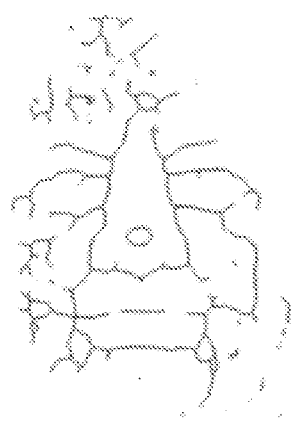

IR image is variance equalized followed by local adaptive equalization and skeletonization to produce IR skeleton in FIG. 19. Range image is similarly processed to produce range skeleton of FIG. 20. The same IR processing applies for all poses as in FIG. 16. The key processing step is adaptive local equalization which emphasizes the structure of the vascular features as well as other linear and spot areas that are locally significantly different from the surrounding skin. Equalization compensates for the thermal nonlinearity of the body, meaning that not all parts of the body heat and cool equally in response to external or internal stimuli. In particular, the nose, cheeks, and ears tend to remain cold longer after the rest of the face warms. Adaptive equalization preserves continuity of blood vessels under varying tissues/bone/etc. Resulting curvilinear features are treated as surface features, where their elevation values are derived from the skin surface elevation rather than the depth of the feature below the skin surface. Discontinuities in the curvilinear features may be connected if less than a selected extent.

A healthy human body may evince a range of skin temperatures on the order of 15° C. Skin immediately over a blood vessel may be only 0.05° C. warmer than adjacent skin. Thermal infrared cameras having 1° C. sensitivity will likely not be useful in distinguishing the location of blood vessels unless the cameras have high spatial resolution and extensive processing is done, including multi-frame integration. Extraction of highly-defined vascular structure in general requires high thermal sensitivity and high spatial resolution. Cameras are commercially available with sensitivity of 0.015° C., meaning 1000 colors or grey levels, or ten bits, would be required to represent one person's thermal pattern at a particular instant. The skin temperature of a live human can vary from −10° F. to 120° F., or a 70° C. variation, meaning 5000 colors or grey levels are required to represent the full range of human thermal characteristics—twelve bits per pixel. That bandwidth cannot be presented effectively in printed or displayed imagery.

The method of the present invention extracts a binary representation of curvilinear features, both internal and external, extracted from 3D infrared images. This requires processing methods that consider localized temperatures in order to minimize the impact of the 15° C. variation across the body, and which consider only the temperatures of a particular body, in order to minimize the impact of the 70° C. spread on the file size and bandwidth requirements. Internal features, including the vasculature, therefore, are located based upon their temperature along a curvilinear path on the skin created by underlying blood vessels. External features, such as the eyelids, mouth, and nose outline, are located based upon edge effects where the abrupt geometrical changes create apparent temperature breaks in the IR image corresponding in location to abrupt elevation changes in the range image.

Prior to skeletonization, the thermal infrared image is processed to remove bad pixels and spurious noise. Adaptive local equalization is performed to emphasize areas of the skin overlaying blood vessels. Because blood vessels vary in depth, sometimes going beneath muscle, bone, or other vessels, simple edge detection or contrast enhancement does not provide continuous features. Adaptive local equalization improves the continuity of features while enhancing their visualization. Thresholding the results creates a binarized network of features that are then skeletonized to produce the one pixel wide features used to establish landmarks for standardization and used to construct an identifying code based on 3D minutiae Two-dimensional filtering operations can be implemented as digital convolution with kernels of limited numbers of pixels. High pass filtering emphasizes details small compared to the size of the convolution kernel, but the technique has limited effectiveness when constrained to small kernels, for which noise may be the primary component enhanced. Larger convolution kernels—on the order of several percent of the image width—have less noise-enhancing results, but require intensive computation time and bandwidth.

Wallis and Peli/Lim enhancement algorithms are summarized as;

$$Y=c(X-X\sim(d))+(1-b)X\sim(d)+bM$$

Where the output image Y is obtained from the original input image S, the 2D low-pass filtered version of the input image X~(d), and the uniform desired mean brightness M which is usually chosen to represent a mid level intensity. In its simplest form, d, c, and b are user controlled constants, d (detail) specifies the 2D low-pass frequency cutoff, and c (contrast) and b (background) are numeric factors in the equation. Considered as a convolution operation, d is the effective kernel size.

The low-pass kernel should be gaussian and radially symmetrical to avoid visible artifacts. Convolving the original image with the low-pass kernel produces an unsharp version. Subtracting it from the original produces a difference image which can be amplified without saturation, with the contrast factor c and the offset M added. The result contains an amplified version of only the high spatial frequency information as determined by detail.

Figure 21A:
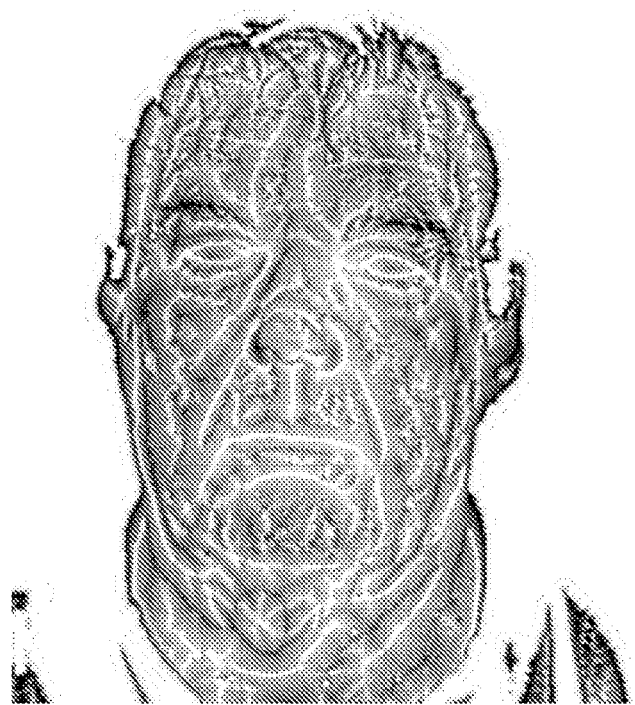
FIGS. 21a and 21b, respectively, show an image with longer and more numerous features collected by a camera (FIG. 21a), as compared to an image collected by a camera (FIG. 21b) having 25% as many detector elements.
Figure 21B:
Figure 22A:
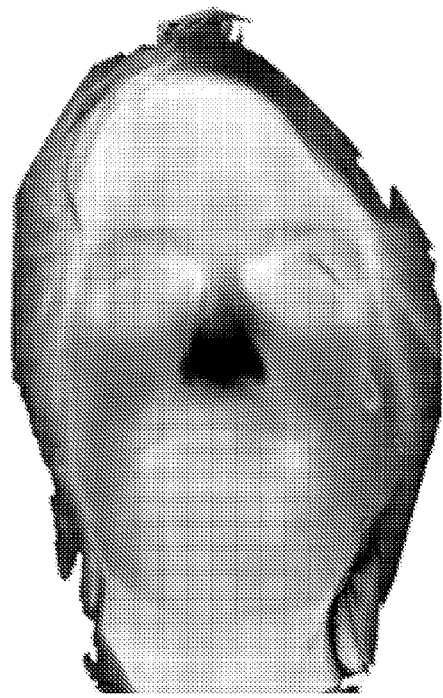
FIG. 22a shows an IR image processed to generate a skeletonized featuremap (FIG. 22b)
Figure 22B:
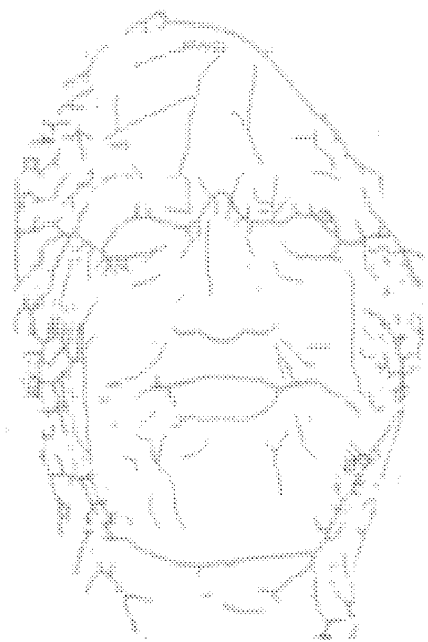
FIG. 22d shows a range image processed to generate a range featuremap (FIG. 22c).
Figure 22D:
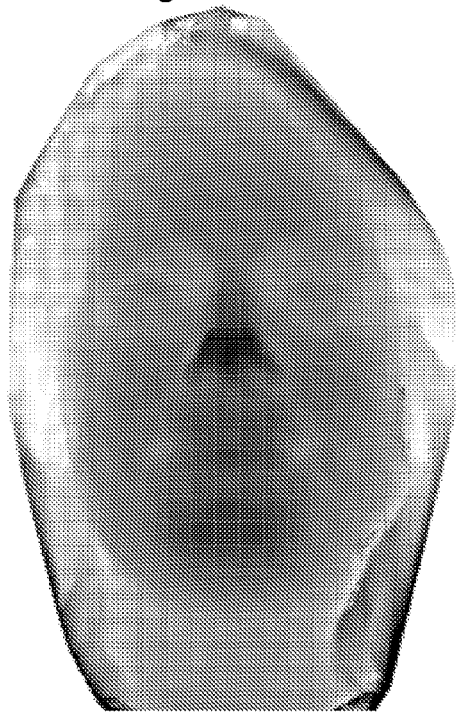
Figure 22C:
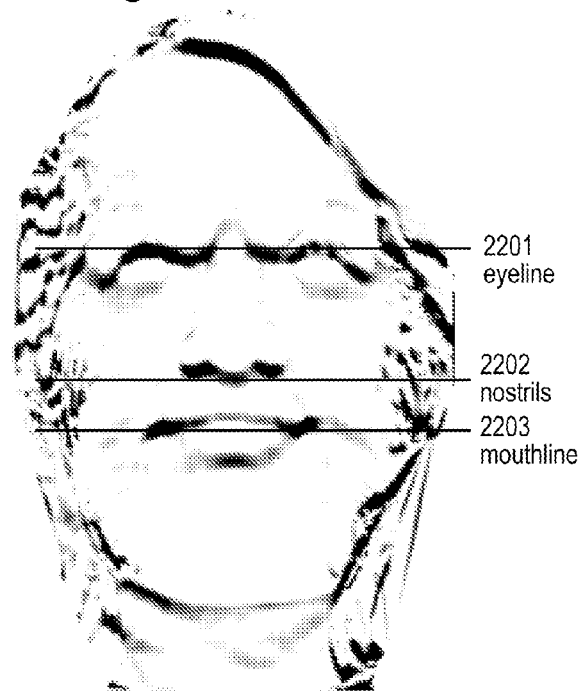

For ease in interpretation, the resulting amplified image can be combined with the original image by adding a weighted percentage of the value from each at each pixel. In the current application, this gives the appearance of curvilinear features being superimposed on the original image. IR cameras with higher thermal sensitivity and greater spatial resolution produce a higher density of IR features, and longer feature lengths. Features produced by cameras with lower sensitivity or resolution are a subset of the features from higher performance cameras. FIG. 21(a) shows longer and more numerous features (white) than (b) which was collected with an imager having only 25% as many detector elements. Many small features seen in (a) are missing from (b). However, feature pixels in b are all a subset of feature pixels in (a).

Classify Nodes and Structures
Distinguish Internal and External Features

FIG. 22 (a) IR image is processed to generate skeletonized featuremap (b). Range image (d) is processed to generate range featuremap (c). Those elements of (b) that are overlaid by features of (c) are colored/labeled external features and the remainder are colored/labeled internal features in (b). Determine features that are coincident in both IR and range images. These are external features which include edges of the eyes, eyebrows, mouth, wrinkles and skin creases on the sides of the nose and outer eye corners, as well as indentation below the nose, vertical lines above the bridge of the nose, moles and scars. Range features without corresponding IR features are also external features. IR features without coincident range features are internal.

Distinguish Vein, Artery, Skin Crease Features

Figure 23:
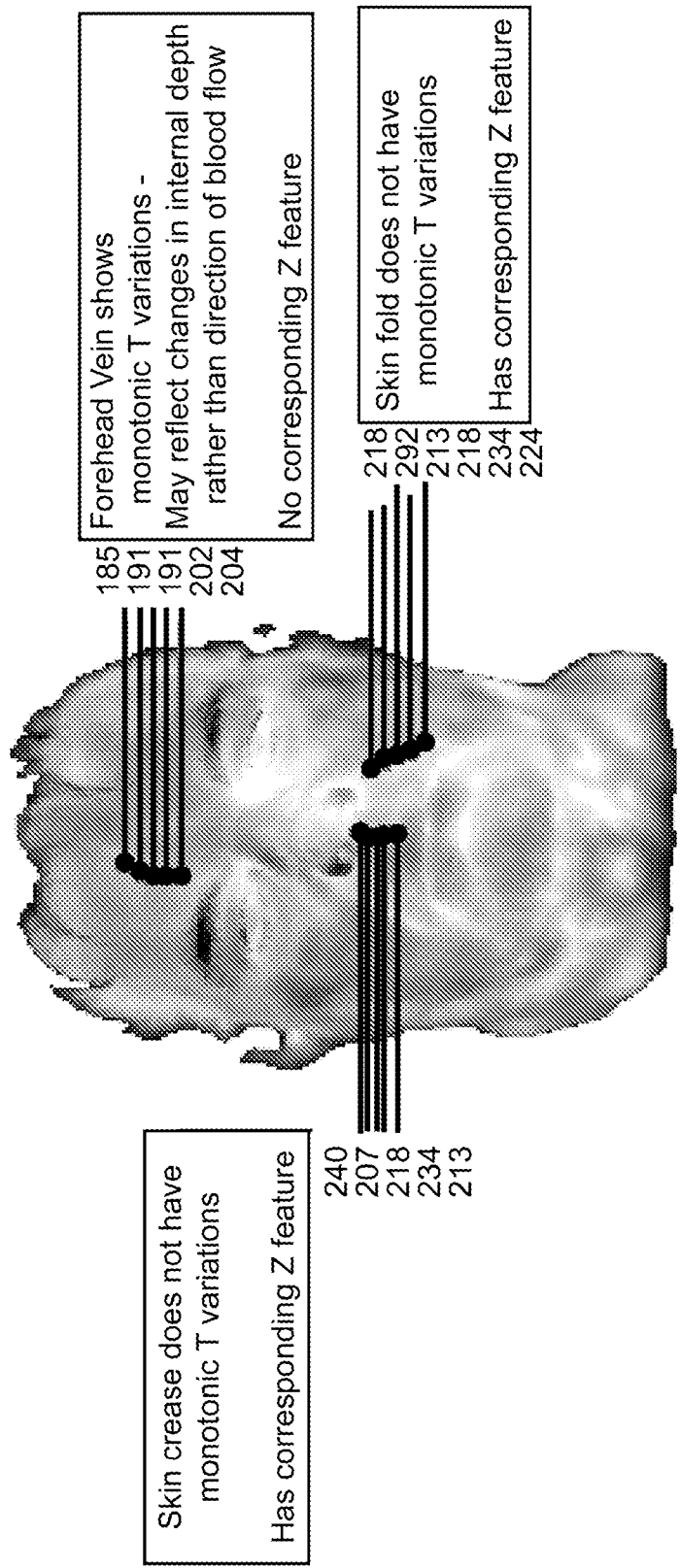
FIG. 23 shows testing of a frame of IR imagery to determine the classification of each feature in the resulting featuremap.

FIG. 23 tests frame of IR imagery to determine classification of each feature in the resulting featuremap. After skeletonization, each pixel location in each skeleton feature is listed. Referring back to the original IR image, the absolute temperature of each listed location is used to determine whether or not temperature is monotonically varying along each feature. Skin creases (a) and skin fold (b) do not have monotonic variation. They do have corresponding range features and therefore are classified as skin creases. Apparent forehead vein (c) has monotonically increasing temperature (decreasing grayscale value) in the direction away from the heart and is therefore labeled a vein. Approximately 80% of blood vessel features extracted from 3D/IR imagery are veins. Arteries will be characterized by decreasing temperatures in the direction away from the heart. Also by the fact that arteries evince the pulse frequency in temperature variations at any point along the feature.

Temperature trends may be illustrative of changes in internal depth rather than the direction of blood flow. Analysis of the rates of changes in feature width and temperature are compared against standard vascular models for an area of the body to make the determination. Also, prior classification from any prior imaging of the patient with CT or MRI that produced designation of veins, arteries, and nerves is transferred to the current image.

Labeling Features

Each curvilinear 3D/IR feature and segment is characterized by type, length, orientation, shape, width variation, range variation, start and end points, number of branches, number of (filled) holes, and similar parameters. Measurements are made in 3D space, where each pixel of IR imagery is assigned the elevation of the registered range pixel. Feature segments are defined as the sub-feature element between two nodes; two branch nodes, one branch and one end node, or two end nodes. Features are comprised of one or more segments that are interconnected or that have disconnects (holes) smaller than a selected distance that are filled-in during processing.

Labeling Nodes

Nodes are extracted from skeletonized IR featuremaps, being the pixel or sub-pixel location where two features intersect or branch, or appear to end. Apparent end point nodes are not reliable landmarks because their position shifts with body temperature, change in sensitivity of the IR imager, change in body position, vasoactive substances, and other influences. Intersection nodes may represent overlaying blood vessels whose apparent intersection point moves with changes in body position. Branch nodes are the most stable landmarks and so are used for standardization.

Nodes are labeled by the region, subregion, and segment from which they are extracted, and by their locations in the coordinate system of the IR imager. Additional label contents can include: orientation of defining vessels, type of vessels, width or vessels, temperature at the node. A layered composite image of the infrared, range, and visual images, plus their featuremaps, plus their skeletonized featuremaps, plus their node maps is then transformed into standard pose.

Pose Standardization

Combining the collection of elevation and infrared images provides true metrics for a 3D/IR image model, allowing volumetric and distance measurements to be made directly and compared over time. The precision with which measurements can be made depends on the precision with which reference points can be specified. Landmarks referenced in elevation, visual, or thermal images of the human body commonly are multi-pixel clusters associated with easily defined locations such as the outer corner of the eye, or the nostril. The range measurement associated with eyes or nostrils may be indeterminate when the range sensor is structured light or a laser radar; absorption of the range illuminator provides no return of elevation measurement within those landmark areas. Interpolating an elevation value from surrounding pixels creates a synthetic value that varies with aspect angle.

True metrics and standization of pose based on anatomical structures results in facilitated ability to perform change detection in IR imagery as well as other modalities of imagery taken simultaneously to the IR with sensors calibrated to the 3D-IR. In addition, the microfeatures that can be extracted from 3D/IR provide precise and repeatable landmarks for registration and repositioning. To obtain landmarks on the skin surface, either a lower sensitivity thermal imager is used, or the thermal image is thresholded as to size, location and intensity of features such that those resulting from deep features are eliminated. To obtain landmarks below the skin surface, triangulation is used by taking multiple 3D/IR images from different aspect angles. The shift in position of a thermal feature pixel relative to points on the skin surface indicates the apparent depth of that pixel.

In the most general case, analyzing images from a portion of the body will not involve areas having natural symmetry. In order to standardize such images, 3 landmark points in an image are selected to define the standard plane for the portion of the body imaged. That plane is then transformed through three-dimensional space into the two-dimensional image plane of the standardized image to be displayed, recorded, or printed. Definitions for the center position and angular rotation are also established for each portion of the body. Unless otherwise detailed, the centroid of the symmetry plane definition trianguloid will be the center of the standardized image. Angular orientation of the standardized image will mimic the orientation of that body portion when the subject is standing upright with arms above his head palms facing forward. An alternative standard will have arms extended to either side with elbows straight and palms facing forward. Other conventions may be used if established to form composite whole body models such as orienting major arteries to be vertical. The process of orienting images of part of the body to fit either of those whole body positions will be called body-centric standardization in this document. If the size of areas imaged is small relative to the whole body model, images can be rearranged to fit other conventions than the primary one described.

Determination that the region imaged is a face approximately frontal with minimal rotation, skew, and tip, is used to reference standardization rules that specify the standardization points for that region of the body in that approximate pose. Nine veins may be extracted from IR images of each side of the face. Specific branch points extractable depend on the sensitivity of the IR imager. When the designated standardization landmarks cannot be extracted, either their position is estimated by extrapolation of the defining veins, or alternate vein nodes are used and that fact annotated in the imagery header. The designated IR landmarks for a face as shown in FIG. 16*b* in red are: L and R Supraochlear-Supraorbital Vein, and L and R Angular-Superficial Labial Veins. Four landmarks are designated for selection in the frontal face shown in FIG. 16; Only three of them can be seen in either profile. Calculations of the standard plane uses three points; for frontal face images, the midpoint of the left and right side Angular-Superficial Labial Veins junction is used as the third point. The resulting standard plane of the face is inside the nose, which provides greater persistence of standardized images in spite of changes to nose anatomy due to ageing, illness, surgery, or trauma.

Figure 18C:
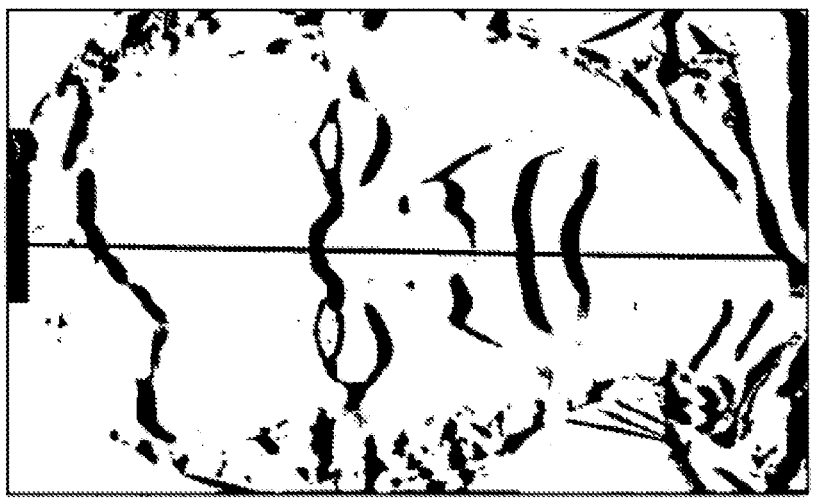
FIG. 18 shows pose standardization illustrating the degree of variation among three subjects.
Figure 18B:
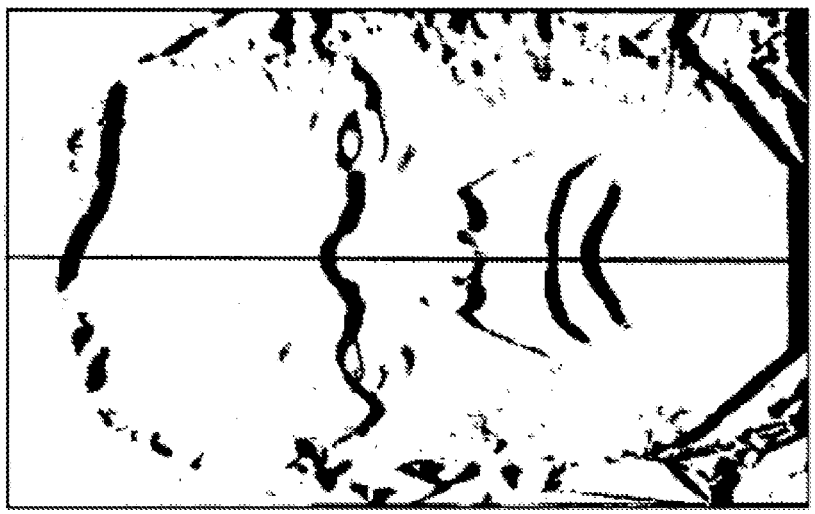
Figure 18A:
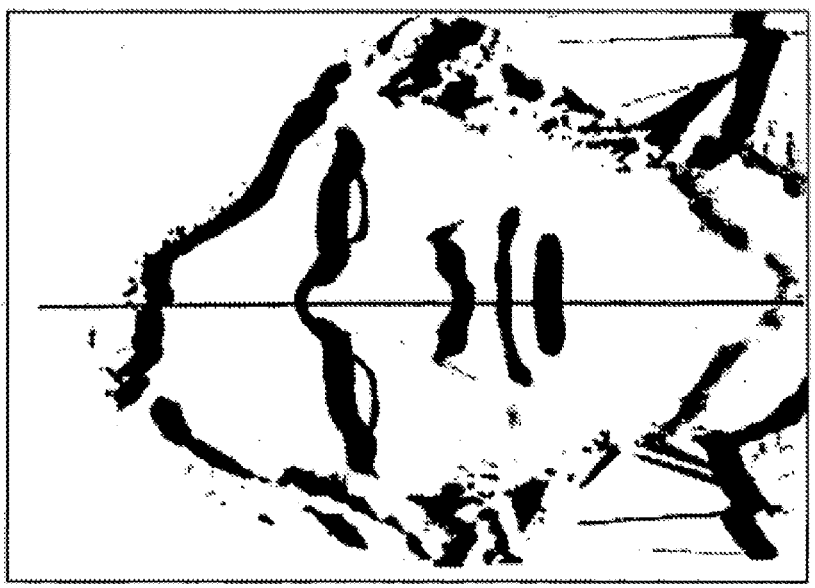

Rather than using three-point standardization from the 3D/IR image, topographic symmetry can be used to establish standard pose. To reduce processing time, isolines are used to correct for skew as in FIG. 15. Filter is applied to the range image to determine Horizontal Edges. Resultant image is processed to locate vertical symmetry plane and image is rotated in frontal pose as FIG. 18 illustrates for three persons. Iterated closest point (ICP) or other technique is used to locate symmetry axis within the imaged region by mirror imaging and best matching original to mirrored images. Tilt standardization is performed by minimizing the variance in distance over the entire face or a selected portion. While this standardization approach is more traditional and does not require determination of specific anatomical branch points in the 3D/IR image, it is prone to variations due to what portion of the face is imaged, and to changes in asymmetries caused by bloating, facial expressions, fatigue, and dentalwork.

Inherent Non-symmetry refers to imagery of a region of the body that has no bilaterally symmetrical component. Inherent Thermal Non-symmetry applies to the heart, upper chest, lower neck, and testes regions. Inherent Topographic Non-symmetry applies to the testes region. Tighter requirements for symmetry expand the regions considered inherently non-symmetrical.

Induced Non-symmetry refers to imagery of a region of the body such as an arm where the field of view does not encompass its bilaterally symmetrical component, or where symmetry has been disturbed by permanent trauma or temporary condition such as the thermal changes and swelling resulting from injury.

The three-point approach to standardization is effective for both symmetrical and non-symmetrical regions of the body, and for all levels of magnification.

Identification Against IR Image Library

Figure 24:
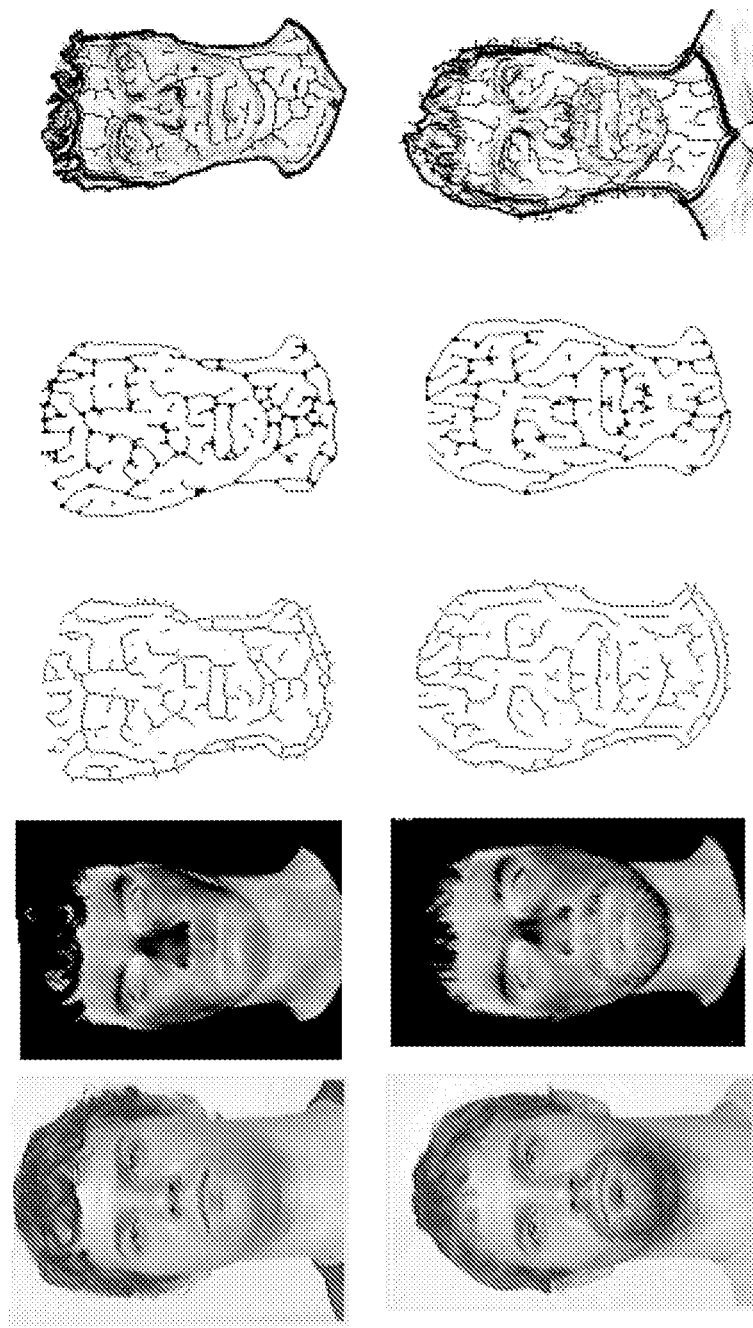
FIG. 24 is a series of images showing post-standardized visual and IR images of identical twins, with featuremaps, nodes, and the composite of IR image+featuremap+nodes for each twin.

FIG. 24 presents post-standardized visual and IR images of identical twins, featuremaps, nodes, and the composite of IR image+featuremap+nodes for each twin. Comparison can be performed using any set of features as a template or after encoding. Featuremap comparison is the most stable and best relates to changes in cameras, temperatures, and facial expressions.

Figure 25A:
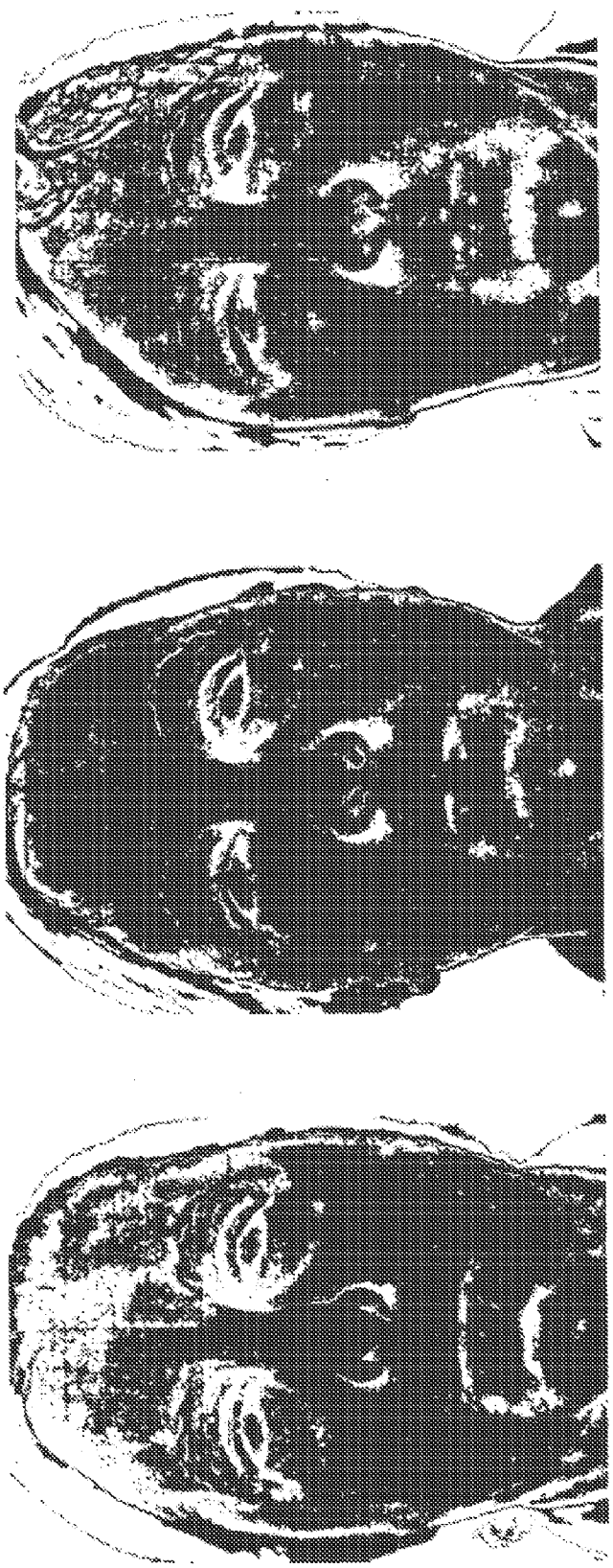
FIG. 25a shows facial images of the same person on different days.

Featuremap structures are persistent for a given person in spite of variations in rotation angle and ambient temperature. More significantly, the same structures are extracted regardless of IR camera's spectral band. The percent of standardized featuremap pixels in one image that are overlaid by featuremap pixels in a second image is a measure of the correlation between the two images and therefore an indicator of the likelihood that both images are of the same person. Images of the same person on different days in FIG. 25(*a*) have different skin temperature and changes in facial hair. FIG. 25(*b*) overlays the extracted skeletonized featuremaps in pairs for comparison. To allow for imprecision in the line processing algorithms, movement of the subject due to respiration and other physiological functioning, effects of aging, drugs, etc. on vasculature, imperfect measurement of head distance, thresholding effects in standardization, and variations between cameras, featuremaps are blurred such as by Gaussian blue with a 1.0 pixel radius, before template matching.

Figure 26:
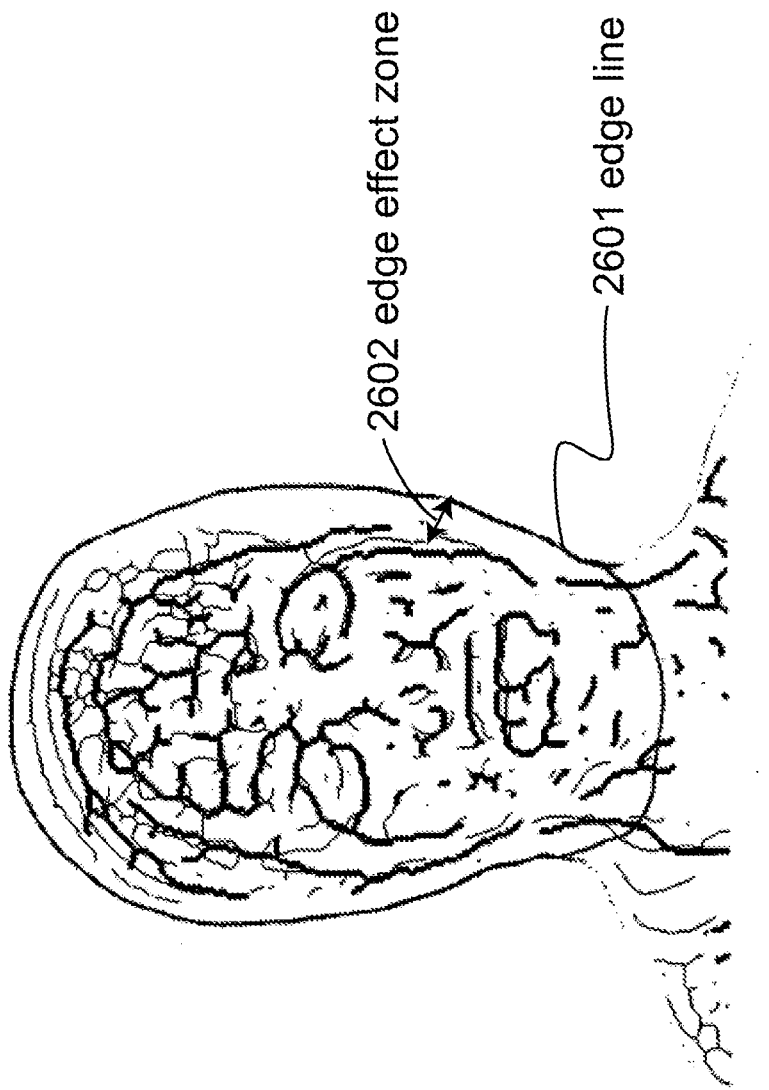
FIG. 26 shows overlaid featuremaps from high performance and lower performance imaging systems.

Same-person comparisons of standardized images taken with identical imaging systems produce overlay percentages of 70% or higher in the common area seen in both images. Twins have higher overlay percentages than unrelated persons on the order of 30% and 15% respectively. When the imaging system is different for the two images being compared, percentages each drop to reflect differences in the total length of features from the two systems. FIG. 26 shows overlaid featuremaps from high performance and lower performance imaging systems. Range image is used to find edgeline 2601. Edge effect zone 2602 is established to cut all feature pixels within a set distance from edgeline in each image. Blurring is performed on featuremap from the higher performance imaging system. Percent of featuremap pixels from lower performance system that are covered by the blurred featuremap, and total number of such pixels are computed. Each computed value must exceed preset thresholds for the two images to be declared the same person.

Identification Against Large Library

Comparison of two standardized images is performed by classification followed by image match or code comparisons. Classification of each image uses distance between eyeline

2201 (FIG. 22) and noseline 2202, and between noseline and mouthline 2203 in the horizontal filtered range image. Total distance between eyeline and mouthline partitions the database into ten or more categories. Ratio of the two distances divides each partition into ten subcategories for a total of 100 subcategories. Alternate or additional classifications are based on distribution of total feature length between each pair of the lines within area of symmetry, distribution of feature orientation within those areas, distribution of nodes within those areas, or other characteristics of the features.

Figure 27:
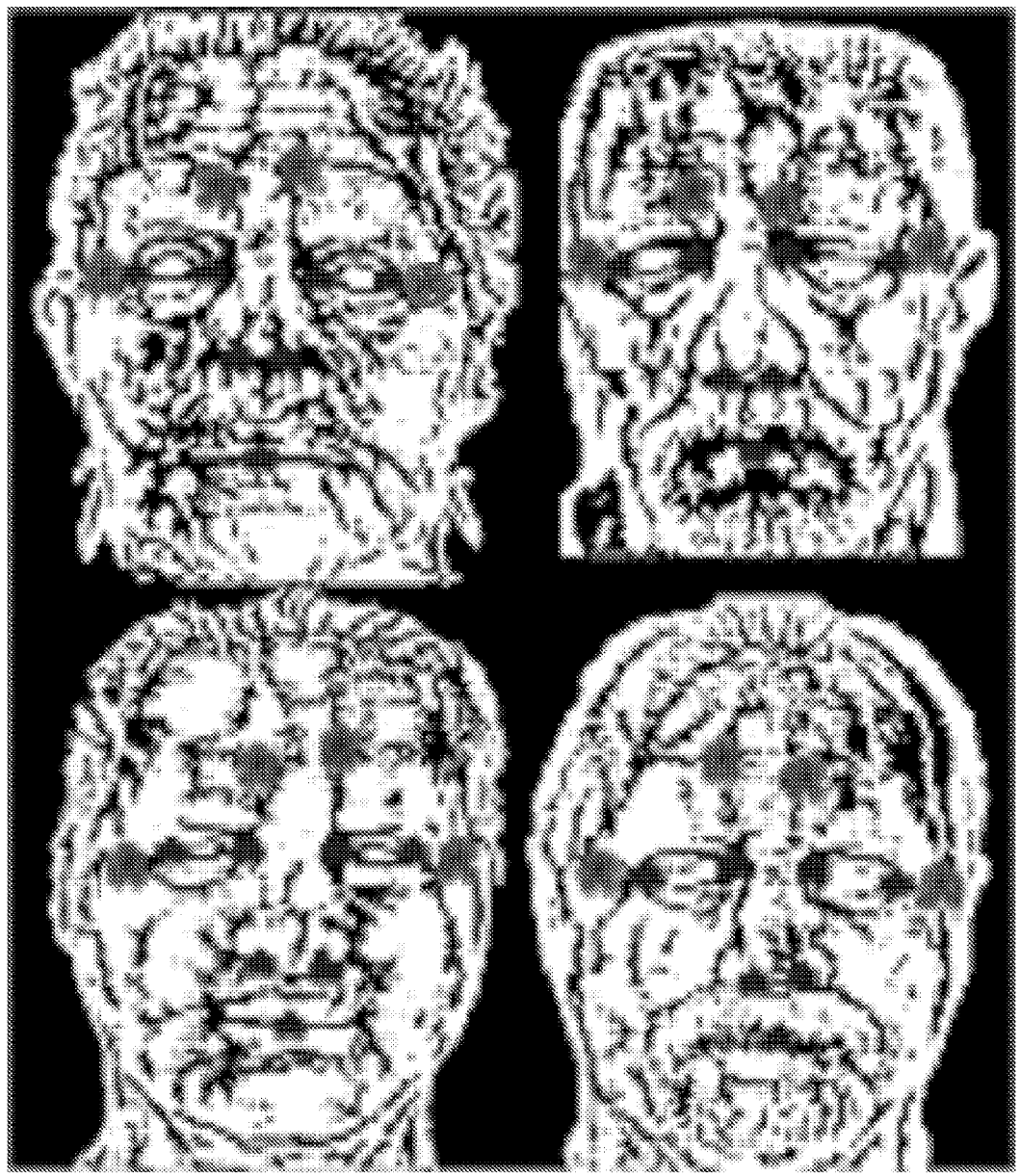
FIG. 27 shows a featuremap code for each of four persons of a reduced size (64×64) standardized frontal skeletonized featuremap with four overlaid vascular (internal) landmarks derived from the 3D/IR image and seven overlaid visual (external) landmarks derived from the range image for each person.
Figure 28:
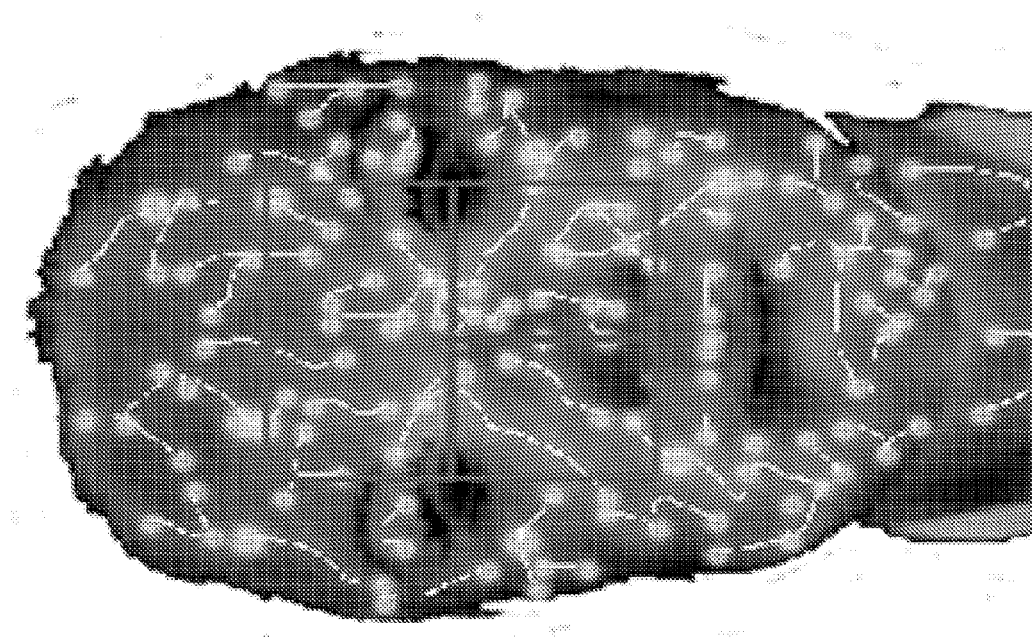
FIG. 28 shows an image and a corresponding matrix of cells reflecting whether or not a featuremap node is located within the corresponding image cell.
Figures 29A, 29B:
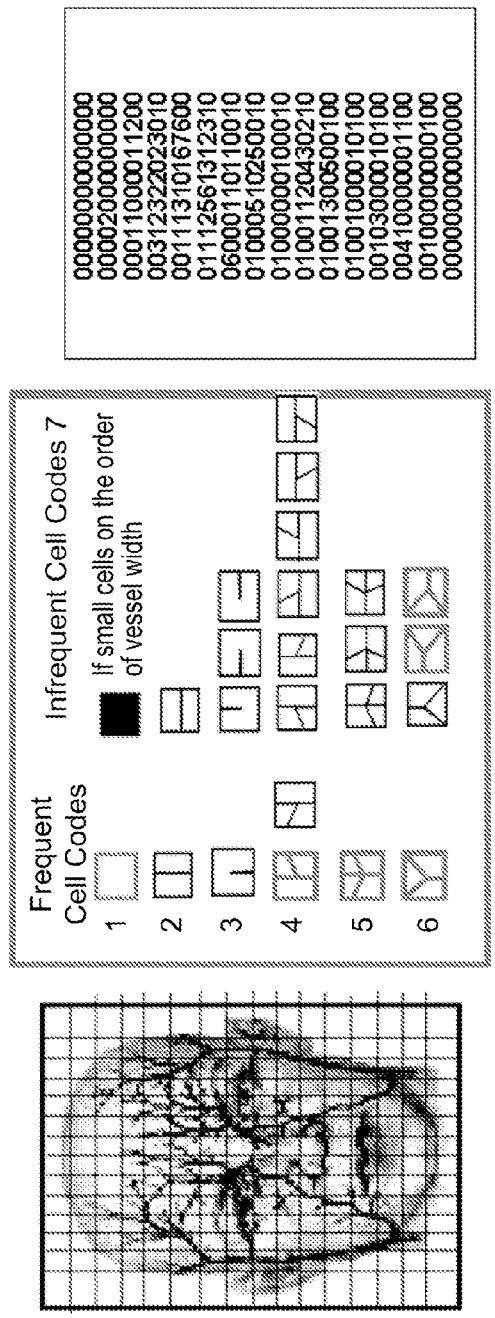
FIG. 29a shows an image divided into cells by a grid, with cell codes and a cell matrix applying the codes to the image.
FIG. 29b is a listing of codes representing seven classes of vascular branchings and seven typographic gradients within each cell.

Unknown images are then matched against library images similarly classified. Overlapping partitions are included. Matching can utilize graph matching of nodes, template matching of featuremaps or skeletonized featuremaps, and Code Comparison. The featuremap code of FIG. 27 is a reduced size (64×64) standardized frontal skeletonized featuremap with four overlaid vascular (internal) landmarks derived from the 3D/IR image and seven overlaid visual (external) landmarks derived from the range image for each person. Encoded images are matched via overlay. The minutiae code of FIG. 28 is a matrix of cells each containing one bit reflecting whether or not a featuremap node is located within the cell. A 10×10 array divides the central face area with width equal to pupil spacing and height equal to twice the eyeline-noseline distance. Code readout is ordered to form a binary string for faster processing. Encoding of FIG. 29 uses 49 symbols (alphabet+numerals+characters! @ # $ % ^ & * : " < > ? ~ /) to represent seven classes of vascular branchings and seven topographic gradient within each cell.

Matching codes must allow for dropouts and local variations associated with injuries, obstructions, and localized changes in either topographic or infrared cell content.

Identification Against Visual Images

If visual images in the reference database are standardized to frontal, ¾, or profile views, ratios of distances between inner and outer eye corners and upper lip center, as well as selected points within nostrils, nose tip, and chin, are computed and used for classification. The unknown 3D/IR image is rotated into a matching pose. Corresponding locations are selected from the range layer and/or from the infrared layer of the 3D/IR image and it is classified using the same decision algorithm as the visual images. In FIG. 17 the range image (a) is filtered to extract edges (b), thresholded (c) and skeletonized (d) to produce pixel-level designations of inner and outer eye corners and upper lip center represented by dots. These are annotated on FIG. 16*b* as blue dots.

Unlike infrared skeletonized featuremaps, which represent actual sharply defined blood vessels, skeletonized range featuremaps represent groove and ridge extremes whose locations shift with viewing aspect. Location of range features varies with muscle tension; fatigue, ageing, cosmetic surgery, and disguise. Landmarks derived from range images are therefore specified by a probability distribution rather than single pixel.

Figure 30A:
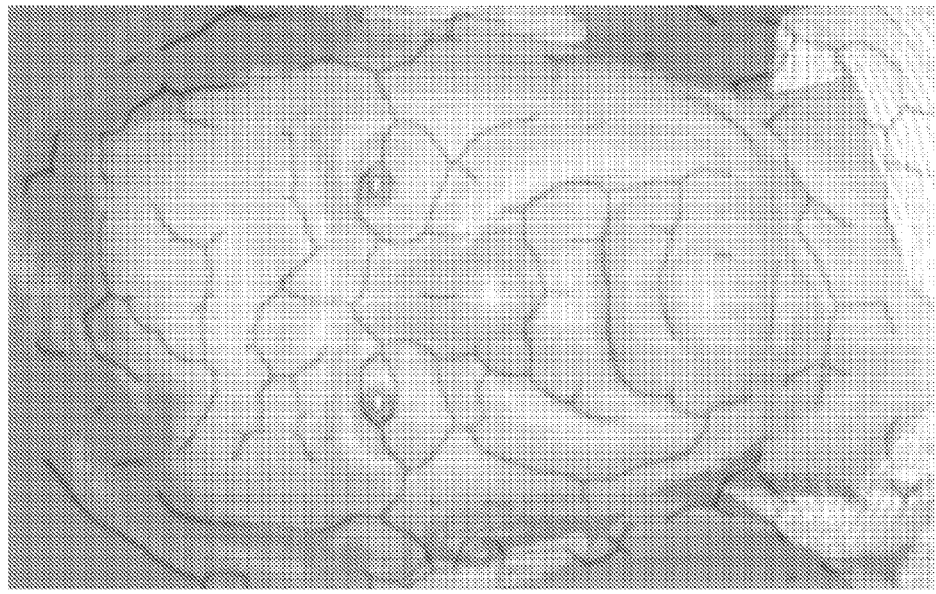
FIG. 30a is an image with range features from an unknown person's best fit onto a visual image of a known person, showing areas of good and poor fit.
Figure 30B:
FIG. 30b is an image with different range features having a better fit and showing a possible match.

FIG. 30(*a*) has range features from an unknown person's 3D/IR image best fit onto visual image of a known person. Fit is best at nose base, but eye and mouth fit is poor. Different range features are good fit for (b) and are considered a possible match.

Figure 31C:
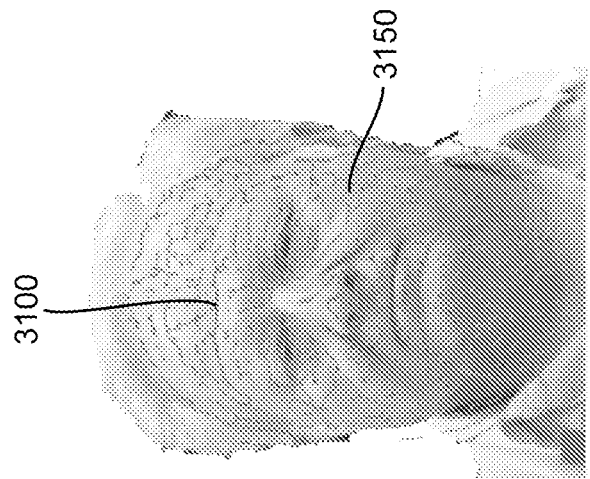
FIG. 31C shows a comparison having a high percentage of overlap, and therefore a probable match.
Figure 31B:
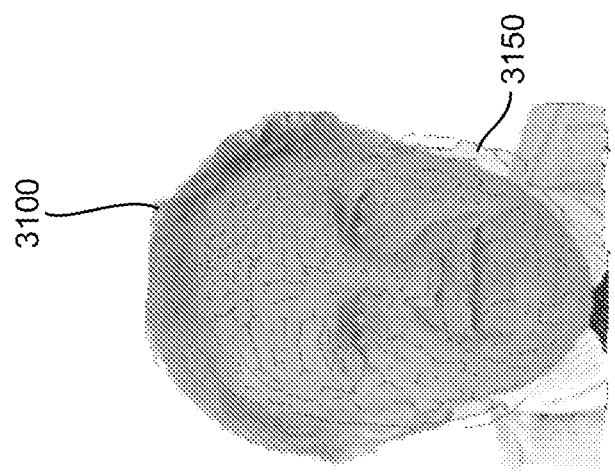
FIG. 31B shows a comparison with a small percentage of overlap, and therefore not a match.
Figure 31A:
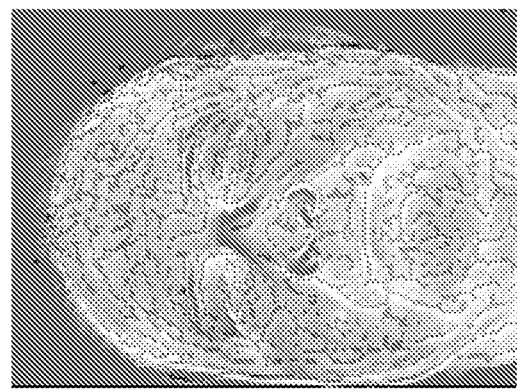
FIG. 31A shows coincidence between IR and range features of an unknown darkened for emphasis.

Having used 3D/IR imagery analysis to transform the unknown IR image into a pose matching the known visual image, external IR features can be matched to visual features in the manner of Prokoski U.S. Pat. No. 6,920,236 and Prokoski U.S. Pat. No. 6,751,340. 3D/IR imagery standardized to frontal pose produces IR and range featuremaps overlaid with coincident features darkened for emphasis. FIG. 31B coincident external IR and range features 3100 (darker) have small percentage overlap with visual features of the unknown in FIG. 31A. Therefore, FIG. 31B cannot be a match. FIG. 31C coincident external IR and range features 3100 have very high percentage overlap with these visual features. Therefore, FIG. 31C can be a match.

Internal IR features are all within the face of FIG. 31C and none violate anatomical rules as defined in the earlier Prokoski patents. Therefore FIG. 31C is designated a match. The present invention adds the additional calculations of total feature length, total number of features, total number of nodes in the unknown IR and range feature maps. Confidence in the match is established as a function of those calculations based on conducting analysis of cross-correlation between a database of 3D/IR and visual images from known persons.

Recognition from Partial Face Images

Analogous to the identification of partial latent fingerprints, analysis of facial vasculature can provide positive identification even when only a portion of the face is seen. IR images of a partial face may be sufficient for unique identification if enough area is seen that is also included in known images. The unknown image is searched for symmetry in range and IR. The range image is best fit to a standard head model to establish the approximate position represented.

Feature map characteristics used to classify the 3D/IR image are used to classify the subregion or segment of the whole body standardization model represented. Corresponding area classification is performed for database images to select candidate matches. Matching is performed by comparison of featuremaps, node patterns, or codes as with larger images. Confidence values are established by analysis of cross-correlation between known images in the database, for the area represented.

Feature and node tracking through sequences of images provides automatic detection of facial expression changes, which can be instrumental in identification, analysis of speech and language, detection of pain and other emotional changes.

Enhancement of System Performance

Modulated thermal sources enhance feature extraction and classification by increasing contrast between external and internal features. Other stimuli cause perceptible physiological changes by certain groups of individuals.

System design issues include the requirement to synchronize imaging from thermal imagers that can collect thousands of frames per second and range imagers that are significantly slower. Both imager types currently produce data arrays on the order of 640×480 with larger arrays being developed. Array sizes are a limiting factor in achieving precise metrics and standardization, and in the potential scalability of a given identification methodology. Range sensors have utility only within certain distance bands determined by the ranging technology. For example, when the target is the size of a human face, structured light is limited to about 0.5 to 2.5 meters; coherent laser radar is effective from about 4 to 50 meters.

Range sensors may be adversely affected by dust, fog, smoke while the thermal sensor is less affected. Uncooled thermal sensor have poor depth of focus, requiring use at fixed distances or use of an autofocus capability. However, changing focal length changes the calibration of the thermal sensor, resulting in mis-registration of the thermal and range images, and incorrect standardization of the layered composite image unless calibrations are performed at a sufficient number of focal lengths so that a calibration exists for a focal length very nearly equal to the focal distance produced by the autofocus.

Other system considerations include the use of very bright visible light or lasers for many structured light systems, and the use of high intensity lasers for coherent laser radar at long distances. Eye safety can be assured by the selection of the laser used, and quality visual images can be obtained by using very short duration flash illumination to minimize obnoxious visual after effects for the subject. When the identification is to be performed without the subject's cooperation, visible illumination is to be avoided.

Currently a sequence of thermal images can be obtained in the time taken to produce a single range image. In the future, range imaging techniques will produce faster frames, offering the possibility of multiple range images within a time interval during which the subject makes negligible movement. In all three sensor types thermal, range, and visual, image sequences can be used to reduce image noise, select the best frames for further processing, classify the subject, provide multiple sample images to enhance the probability of a database match, and to pinpoint landmark areas in the image such as blinking eyes in thermal sequences.

Display of IR surface features such as skin pores, scars and moles assists in relating internal anatomical structures displayed on a monitor to surface locations on the subject's skin surface, and to repeatedly relocating the same fine points. Display of arteries assists in guiding minimally invasive surgical procedures. Minutiae display and encoding provides references for determining changes over time within specific voxels. Minutiae can also be used to evaluate and/or remove effects of respiration, cardiac cycle, and other movements during scanning, as well as aligning imagery from different sessions in which the patient's position is different, the scanner has different performance parameters, the patient's size or condition has changed.

While the invention has been described in terms of preferred embodiments, those skilled in the art will recognize that the invention can be practiced with modification within the spirit and scope of the appended claims.

Having thus described my invention, what I claim as new and desire to secure by Letters Patent is as follows:

1. A method for establishing a searchable library of human images using a computerized system, comprising:
generating with a primary mode of medical imaging a three dimensional (3D) mesh of a whole body model linked to anatomical landmarks that can be seen in imagery produced by a plurality of medical imaging modes, each mode having a different type of imaging sensor, the 3D segment mesh serving as a reference and causing minimal interference with said plurality of imaging modes performed simultaneously, said 3D reference mesh enabling comparison of images of different 3D orientation;
calibrating by the computerized system a geometry of a primary mode sensor in order to standardize images for automated comparison, including images generated by said plurality of imaging modes, said imaging modes comprising different types of sensors, ranges of sensitivity, and resolution;
applying by the computerized system standards for acceptable image quality from said plurality of imagers;
applying by the computerized system standards for metadata accompanying transmission or storage of said images;
providing access control provisions for transmission and storage of the images;
applying by the computerized system procedures for detecting and correcting errors in the images; and
storing standardized images in the library.

2. A method as in claim 1, wherein the calibrating step further comprises:
specifying a body-centric coordinate system;
identifying a defined axis for each anatomical division of the body, the anatomical divisions including regions, sub-regions, and body segments within a region;
determining three specified landmark points in each division used for standardization, the three landmark points for each segment defining a facet;
combining facets to form a faceted 3D model; and
replacing facet edges by transition curves to form a three dimensional (3D) model.

3. A method as in claim 1, wherein storing standardized images in the library further comprises processing the images in accordance with the standards for acceptable quality and for metadata.

4. A method as in claim 2, further comprising automatic standardization through contemporaneous use of three dimensional infrared imaging (3D/IR).

5. A method as in claim 4, further comprising:
extracting feature maps from the 3D/IR images;
establishing a directory of reference points for each division of the body;
using three designated reference points to standardize a pose for each image; and
storing standardized images in a database along with the metadata for each.

6. A method for standardizing medical images such that the subject appears in a standard pose, comprising:
simultaneously capturing images of the subject from thermal infrared, range, and a medical imaging sensor;
producing a 3D/IR image through intrinsic and extrinsic calibration of the range and infrared sensors;
extracting anatomical curvilinear line segment features from the three dimensional thermal images by performing locally adaptive filtering to enhance visualization of internal and external anatomical structures including blood vessels and skin folds;
selecting three or more landmark points either manually or automatically where the anatomical landmark points to be selected are specified for the body part being imaged;
transforming the 3D/IR image into a standard pose specified for the area of the body imaged by transforming the plane determined by the three selected points into an orientation and position specified for that standard pose; and
transforming the medical sensor image into standard pose by overlaying the medical sensor image on the 3D/IR image through intrinsic and extrinsic calibration of the IR and medical sensors.

7. The method of claim 6, wherein the medical image sensor is an IR sensor.

8. The method of claim 6, further comprising differentiating internal and external features in infrared images by the further steps of:
extracting curvilinear line segment features from range and thermal image layers in a body map;
determining which features appear in both layers;
designating features that appear in both thermal and range images as external features; and
designating features that appear in the thermal but not in the range images as internal features.

9. The method of claim 6, further comprising differentiating veins from arteries in infrared images by the further steps of:
determining whether temperature is monotonically varying along the feature;
determining direction of apparent thermal flow in accordance with said monotonic temperature variation;

determining temporal rate of temperature variation at any point along the feature;

determining pulse rate; and estimating changes in internal depth from changes in detected feature width and temperature using standard vascular model for the area of the body, or from any prior designation of veins, arteries, and nerves in images of a specified patient.

\* \* \* \* \*